(12) United States Patent
Voelker et al.

(10) Patent No.: US 8,969,053 B2
(45) Date of Patent: Mar. 3, 2015

(54) MUTANT YQHD ENZYME FOR THE PRODUCTION OF A BIOCHEMICAL BY FERMENTATION

(75) Inventors: François Voelker, Montrond les Bains (FR); Laurence Dumon-Seignovert, Pont du Chateau (FR); Philippe Soucaille, Deyme (FR)

(73) Assignee: Metabolic Explorer, Saint Beauzire (FR)

( * ) Notice: Subject to any disclaimer, the term of this patent is extended or adjusted under 35 U.S.C. 154(b) by 78 days.

(21) Appl. No.: 13/387,347

(22) PCT Filed: Jul. 30, 2010

(86) PCT No.: PCT/EP2010/061106
§ 371 (c)(1),
(2), (4) Date: Jan. 26, 2012

(87) PCT Pub. No.: WO2011/012697
PCT Pub. Date: Feb. 3, 2011

(65) Prior Publication Data
US 2012/0122169 A1    May 17, 2012

Related U.S. Application Data

(60) Provisional application No. 61/229,866, filed on Jul. 30, 2009.

(30) Foreign Application Priority Data

Jul. 30, 2009  (EP) .................................... 09166856

(51) Int. Cl.
| | | |
|---|---|---|
| C12P 7/26 | (2006.01) | |
| C12P 1/00 | (2006.01) | |
| C12N 9/04 | (2006.01) | |
| C12N 9/88 | (2006.01) | |
| C12P 7/18 | (2006.01) | |

(52) U.S. Cl.
CPC ................. *C12P 7/26* (2013.01); *C12N 9/0006* (2013.01); *C12N 9/88* (2013.01); *C12P 7/18* (2013.01); *C12Y 101/01002* (2013.01); *C12Y 101/01006* (2013.01); *C12Y 402/03003* (2013.01)
USPC ............................................. 435/148; 435/41

(58) Field of Classification Search
None
See application file for complete search history.

(56) References Cited

U.S. PATENT DOCUMENTS

| | | |
|---|---|---|
| 2010/0261239 A1 | 10/2010 | Soucaille et al. |
| 2011/0201070 A1 | 8/2011 | Soucaille et al. |
| 2012/0135487 A1* | 5/2012 | Voelker et al. ................. 435/158 |

FOREIGN PATENT DOCUMENTS

| | | |
|---|---|---|
| WO | 98/37204 | 8/1998 |
| WO | 2008/116848 | 10/2008 |
| WO | 2008/116853 | 10/2008 |

OTHER PUBLICATIONS

Altaras et al., Enhanced Production of (R)-1,2-Propanediol by Metabolically Engineered *Escherichia coli*, Biotechnol. Prog. (2000), vol. 16, pp. 940-946.*
Q46856 (last viewed on Jul. 8, 2013).*
Ko et al., Conversion of methylglyoxal to Acetol by *Escherichia coli* Aldo-Keto Reductases, Journal of Bacteriology (2005), vol. 187(16), pp. 5782-5789.*
UniProtKB/Swiss-Pro Q468.57.3 YqhE *E. coli*.(last viewed on Jul. 2, 2014).*
Guo et al., Protein tolerance to random amino acid change, 2004, Proc. Natl. Acad. Sci. USA 101: 9205-9210.*
Lazar et al., Transforming Growth Factor α: Mutation of Aspartic Acid 47 and Leucine 48 Results in Different Biological Activity, 1988, Mol. Cell. Biol. 8:1247-1252.*
Hill et al., Functional Analysis of conserved Histidines in ADP-Glucose Pyrophosphorylase from *Escherichia coli*, 1998, Biochem. Biophys. Res. Comm. 244:573-577.*
Wacey et al., Disentangling the perturbational effects of amino acid substitutions in the DNA-binding domain of p53., Hum Genet, 1999, vol. 104, pp. 15-22.*
Branden and Tooze, Introduction to Protein Structure (1999), 2nd edition, Garland Science Publisher, pp. 3-12.*
Partial European Search Report Based on European Search Report EP 09 16 6856 Completed Oct. 19, 2009.
International Search Report Based on PCT/EP2010/061106 Mailed March 29, 2011.
Wang et al.; "Production of 1,3-Propanediol from Glycerol by Recombinant *E. coli* Using Incompatible Plasmids System"; Mol Biotechnol; 2007; vol. 37; pp. 112-119; Humana Press Inc.

(Continued)

*Primary Examiner* — Alexander Kim
(74) *Attorney, Agent, or Firm* — Miles & Stockbridge PC

(57) ABSTRACT

The present invention concerns a method for the production of a biochemical selected among acetol and 1,2-propanediol, 1,3-propanediol, ethylene glycol and 1,4-butanediol comprising culturing a microorganism modified for an improved production of the biochemical selected among acetol and 1,2-propanediol, 1,3-propanediol, ethylene glycol and 1,4-butanediol in an appropriate culture medium and recovery of the desired biochemical which may be further purified wherein the microorganism expresses a YqhD enzyme which catalytic efficiency toward NADPH is increased.

The present invention also relates to a mutant YqhD enzyme comprising at least one amino acid residue in the protein sequence of the parent enzyme replaced by a different amino acid residue at the same position wherein
 the mutant enzyme has retained more than 50% of the YqhD activity of the parent enzyme and
 the catalytic efficiency toward NADPH of the mutant YqhD is increased as compared with the catalytic efficiency toward NADPH of the parent enzyme.

15 Claims, 5 Drawing Sheets

(56) References Cited

OTHER PUBLICATIONS

Rao et al.; "Engineered *Saccharomyces cerevisiae* that Produces 1,3-Propanediol From D-glucose"; Journal of Applied Microbiology; 2008; vol. 105; pp. 1768-1176; The Society for Applied Microbiology.

Tang et al.; "Microbial Conversion of Glycerol to 1,3-Propanediol by an Engineered Strain of *Escherichia coli*"; Applied and Environmental Microbiology; Mar. 2009; vol. 75; No. 6; pp. 1628-1634; American Society for Microbiology.

Nakamura et al.; "Metabolic Engineering for the Microbial Production of 1,3-Propanediol"; Current Opinion in Biotechnology; 2003; vol. 14; pp. 454-459.

Li et al.; "Enhanced Activity of YqhD Oxidoreductase in Synthesis of 1,3-Propanediol by Error-Prone PCR"; Progress in Natural Science 18; 2008; pp. 1519-1524; National Natural Science Foundation of China and Chinese Academy of Sciences; Elsevier Limited.

Perez et al.; "*Escherichia coli* YqhD Exhibits Aldehyde Reductase Activity and Protects From the Harmful Effect of Lipid Peroxidation-Derived Aldehydes"; The Journal of Biological Chemistry; Mar. 21, 2008; vol. 283; No. 12; pp. 7346-7353; The American Society for Biochemistry and Molecular Biology, Inc.

Sulzenbacher et al; "Crystal Structure of *E. coli* Alcohol Dehydrogenase YqhD: Evidence of a Covalently Modified NADP Coenzyme"; J. Mol. Biol.; 2004; vol. 342; pp. 489-502; Elsevier Ltd.

Miller et al.; "Silencing of NADPH-Dependent Oxidoreductase Genes (YqhD and DKGA) in Furfural-Resistant Ethanologenic *Escherichia coli*"; Applied and Environmental Microbiology; Jul. 2009; vol. 75; No. 13; pp. 4315-4323; American Society for Microbiology.

Cameron et al.; "Metabolic Engineering of Propanediol Pathways"; Biotechnol. Prog.; 1998; vol. 14; pp. 116-125; American Chemical Society and American Institute of Chemical Engineers.

Altaras et al.; "Enhanced Production of (R)-1,2-Propanediol by Metabolically Engineered *Escherichia coli*"; Biotechnol. Prog.; 2000; vol. 16; pp. 940-946; American Chemical Society and American Institute of Chemical Engineers.

Bennett et al.; "Microbial Formation, Biotechnological Production and Applications of 1,2-Propanediol"; Appl Microbiol Biotechnol; 2001; vol. 55; pp. 1-9; Springer-Verlag.

Ko et al.; "Conversion of Methylglyoxal to Acetol by *Escherichia coli* Aldo-Keto Reductases"; Journal of Bacteriology; Aug. 2005; vol. 187; No. 16; pp. 5782-5789.

Guldener et al.; "A New Efficient Gene Disruption Cassette for Repeated Use in Budding Yeast"; Nucleic Acids Research; 1996; vol. 24; No. 13; pp. 2519-2524; Oxford University Press.

Schiestl et al.; "High Efficiency Transformation of Intact Yeast Cells Using Single Stranded Nucleic Acids as a Carrier"; Curr Genet; 1989; vol. 16; pp. 339-346; Springer-Verlag.

Shevchuk et al.; "Construction of Long DNA Molecules Using Long PCR-Based Fusion of Several Fragments Simultaneously"; Nucleic Acids Research; 2004; vol. 32; No. 2; pp. 1-12; Oxford University Press.

Farinas et al.; "Directed Enzyme Evolution"; Current Opinion in Biotechnology; 2001; vol. 12; pp. 545-551; Elsevier Science Ltd.

Bohren et al.; "The Structure of APO R268A Human Aldose Reductase: Hinges and Latches that Control the Kinetic Mechanism"; Biochimica et Biophysica Acta 1748; 2005; pp. 201-212; Elsevier B.V.

Atsumi et al.; "Engineering the Isobutanol Biosynthetic Pathway in *Escherichia coli* by Comparison of Three Aldehyde Reductase/Alcohol Dehydrogenase Genes"; Appl Microbiol; 2010; vol. 85; pp. 651-657; Springer.

\* cited by examiner

```
                 1
4HDB_CLOKL       -------MKL LK---LAPDV YKFDTAEEFM KY---FKVGK GDPILTNEFL Y--KP-FLEK FNDGAD----
YQHD_ECOLI       ----MNNFNL RT---PTRIL FGKGAIAGLR EQ-I-PHDAR VLITYGGGSV K--KTGVLDQ VLDALK----
ADH3_ENTHI       --MTMLNFTY YN---PVRLI YGKGSLDEIE KQHLIPEDAR IMKTYGGGSS K--KNGVYEE VLKHIK----
ADHA_BACSU       ----MQNFTY WN---PTKLI FGRGEVERLP EE-LKPYGKN VLLVGGGSI K--RSGLYDQ VIEQLN--KA
ADHB_BACSU       ----MENFTY YN---PTKLI FGKGQLEQLR KE-FKRYGKN VLLVYGGGSI K--RNGLYDQ VTGILK--EE
ADHB_CLOAB       ----MVEFEY SI---PTRIF FGKDKINVLG RE-LKKYGSK VLIVGGGSI K--RNGIYDK AVSILE--KN
ADHA_CLOAB       ----MLSFDY SI---PTKVP FGKGKIDVIG EE-IKKYGSR VLIVGGGSI K--RNGIYDR ATAILK--EN
MACA1_RHOOP      --MAERSSEF VFTGNPARVI FGAGRMRNVR EE-VERLGRG RVLLLGSENL R----EVCDQ VQDLLG----
TFDF2_RALEJ      TGDLNEFVAH FW---PVRVV FGAGSTERIP AE-VKRLGAR RALVLCTPD- ---QRDLAQR VLGDLG----
TFDF1_RALEJ      ---MKKFTLD YL---SPRVV FGAGTASALP DE-IGRLGAR RPLVLSSPE- ---QRELAKD IVRPIG----
CLCE_PSESB       ----MNFIHD YR---SPRVI FGPDSLARLP QE-LERLGID RALVLTTPE- ---QAPLGRQ VAEPVI----
ADH1_CLOSA       ------MMRF TL---PRDIY YGKGSLEQLK N----LKGKK AMLVLGGGSM K--RFGFVDK VLGYLK--EA
ADH2_ENTHI       ADRRRNNLQWF RV---PPKIF FEPHSIRYLA E---LKELS KIFIVSDRMM Y--KLGYVDR VMDVLKRRSN
ADHE_ECO57       AKRAENMLWH KL---PKSIY FRRGSLPIAL DE-VITDGHK RALIVTDRFL P--NNGYADQ ITSVLK--AA
MEDH_RHOER       QIWDFPIKEF HP---PPRAL MGVGAHDIIG VE-AKNLGFK RTLLMTTG-L R--GSGIIEE LVGKIE--YQ
EUTG_SALTY       TLNLQRVKTF SV---PPVTL CGLGALGACG QE-AQARGVS HLFVMVDSFL H--QAGMTAP LARSLA--MK
EUTG_ECOLI       TLNLQRVKTF SV---PPVTL CGPGSVSSCG QQ-AQTRGLK HLFVMADSFL H--QAGMTAG LTRSLT--VK
GBSB_BACSU       VESMQKFHTF EI---PTVIK HGIGAIKHTG EE-VAALGVS KALLVTDPGI Y--KAGVADP VIESLK--EA
FUCO_ECO57       ----MMANRM IL---NETAW FGRGAVGALT DE-VKRRGYQ KALLVTDKTL V--QCGVVAK VTDKMD--AA
MEDH_BACMT       ------MTNF FI---PPASV IGRGAVKEVG TR-LKQIGAK KALIVTDAFL H--STGLSEE VAKNIR--EA
DHAT_CITFR       --MSYRMFDY LV---PNVNF FGPNAISVVG ER-CKLLGGK KALLVTDKGL RAIKDGAVDK TLTHLR--EA
DHAT_KLEPN       --MSYRMFDY LV---PNVNF FGPNAISVVG ER-CQLLGGK KALLVTDKGL RAIKDGAVDK TLHYLR--EA
ADH4_YEAST       IRKMSSVTGF YI---PPISF FGEGALEETA DY-IKNKDYK KALIVTDPGI A--AIGLSGR VQKMLE--ER
ADH4_SCHPO       SSKAMPVSAF YI---PSFNL FGKGCLAEAA KQ-IKMSGFK NTLIVTDPGI I--KVGLYDK VKALLE--EQ
ADH2_ZYMMO       ----MASSTF YI---PFVNE MGEGSLEKAI KD-LNGSGFK NALIVSDAFM N--KSGVVKQ VADLLK--AQ
ADH2_ECOLI       ----MAASTF FI---PSVNV IGADSLTDAM NM-MADYGFT RTLIVTDNML T--KLGMAGD VQKALE--ER 71
4HDB_CLOKL       AVFQEKYG-- LGEPSDEMIN NIIKDIGDKQ YNRIIAVGGG SVIDIAKILS LKYTDD--SL DLFE------
YQHD_ECOLI       GMDVLEFGGI EPNPAYETLM NAVKLVREQK VTFLLAVGGG SVLDGTKFIA AAANYPENI- DPWHIL---Q
ADH3_ENTHI       --PIVEFGGI EPNPSHETCI KAIKIAKENK INFLVAVGGG SIIDATKYIA LGMEHTYSD- DPYDICLKGG
ADHA_BACSU       GATVHELAGV EPNPRVSTVN KGVAICKEQN IDFLLAVGGG SVIDCTKAIA AGAKYD--G- DAWDIV----
ADHB_BACSU       GAVVHELSGV EPNPRLATVE KGIGLCREHD IDFLLAVGGG SVIDCTKAIA AGVKYD--G- DAWDIF----
ADHB_CLOAB       SIKFYELAGV EPNPRVTTVE KGVKICRENG VEVVLAIGGG SAIDCAKVIA AACEYD--G- NPWDIV----
ADHA_CLOAB       NIAFYELSGV EPNPRITTVK KGIEICRENN VDLVLAIGGG SAIDCSKVIA AGVVYD--G- DTWDMV---K
MACA1_RHOOP      ELFVNRYDGA AMHTPVEVTD IALAQLRTSE ADCVVAIGGG STTGLAKALA A--------- ----------
TFDF2_RALEJ      DLGAGFHDGA VMHVPEASVT RAAQAARDAD ADLLVAVGGG STIGLAKALA L--------- ----------
TFDF1_RALEJ      DRVAGYFNDTD TMHVPVDVIQ KAERAFNDTD ADSIIAIGGG STTGLAKILS M--------- ----------
CLCE_PSESB       GHVAAFYDGA TMHVPALVAE EACKIARTSE ANGVIAIGGG STIGLAKIVA L--------- ----------
ADH1_CLOSA       GIEVKLIEGV EPDPSVETVF KGAELMRQFE PDWIIAMGGG SPIDAAKAMW IFYEHP--E- KTFDDI---K
ADH2_ENTHI       EVEIEIFIDV EPDPSIQTVQ KGLAVMNTFG PDNIIAIGGG SAMDAAKIMW LLYEHP--E- ADFFAM---K
ADHE_ECO57       GVETEVFFEV EADPTLSIVR KGAELANSFK PDVIIALGGG SPMDAAKIMW VMYEHP--E- THFEEL---A
MEDH_RHOER       GVEVVLYDKV ESNPKDYNVM EAAALYQKEK CDSIISIGGG SSHDAAKGAR VVIAHD--GR NINEPE---G
EUTG_SALTY       GVAMTVWPCP PGEPCITDVC AAVAQLREAA CDGVVAFGGG SVLDAAKAVA LLVTNP--D- QTLSAM---T
EUTG_ECOLI       GIAMTLWPCP VGEPCITDVC AAVAQLRESG CDGVIAFGGG SVLDAAKAVT LLVTNP--DS TLAEMS----
GBSB_BACSU       GIEVVLFNKV EPNPPVRLVN EGSELYKEN CNGLVAVGGG SSMDTAKAIG VEATHE--G- SVLDYEAADG
FUCO_ECO57       GLAWAIYDGV VPNPTITVVK EGLGVFQNSG ADYLIAIGGG SPQDTCKAIG IISNNPEFA- DVRSLE---G
MEDH_BACMT       GLDVAIFPKA QPDPADTQVH EGVDVFKQEN CDALVSIGGG SSHDTAKAIG LVAANG--G- RINDYQ---G
DHAT_CITFR       GIDVVVFDGV EPNPKDTNVR DGLEVFRKET CDIIVTVGGG SPHDCGKGIG IAATHE--G- DLYSYA---G
DHAT_KLEPN       GIEVAIFDGV EPNPKDTNVR DGLAVFRREQ CDIIVTVGGG SPHDCGKGIG IAATHE--G- DLYQYA---G
ADH4_YEAST       DLNVAIYDKT QPNPNIANVT AGLKVLKEQN SEIVVSIGGG SAHDNAKAIA LLATNG--G- EIGDYE---G
ADH4_SCHPO       SITVHLYDGV TPNPTVGNVN QGLEIVKENN CDSMVSIGGG SAHDCAKGIA LLATNG--G- KIADYE---G
ADH2_ZYMMO       GINSAVYDGV MPNPTVTAVL EGLKILKDNN SDFVISLGGG SPHDCAKGIA LVATNG--G- EVKDYE---G
ADH2_ECOLI       NIFSVIYDGT QPNPTTENVA AGLKLLKENN CDSVISLGGG SPHDCAKGIA LVAANG--G- DIRDYE---G 141
4HDB_CLOKL       ---------- --GKVPLVKN KELIIVPTTC GTGSEVTNVS VAELKR---R HTKKGIASDE LYATYAVLVP
YQHD_ECOLI       ---------- -TGGKEIKSA IPMGCVLTLP ATGSESNAGA VISRKT---T GDKQAFHSAH VQPVFAVLDP
ADH3_ENTHI       ---------- --KFKVNPAQ AKIGVVLTLP ATGSETNCWG VISRHA---D KLKLPFNNES VFPTWSIVDP
ADHA_BACSU       ---------- --TKKHQPKDA LPFGTVLTLA ATGSEMNSGS VITNWE---T KEKYGWGSPL VFPKFSILDP
ADHB_BACSU       ---------- --SKKVTAEDA LPFGTVLTLA ATGSEMNPDS VITNWE---T NEKFVWGSNV THPRFSILDP
ADHB_CLOAB       ---------- --LDGSKIKRV LPIASILTIA ATGSEMDTWA VINNMD---T NEKLIAAHPD MAPKFSILDP
ADHA_CLOAB       ---------- --DPSKITKV LPIASILTLS ATGSEMDQIA VISNME---T NEKLGVGHDD MRPKFSVLDP
MACA1_RHOOP      ---------- -------RTG VDQVILPTTY A-GSEVTP-- VLGETV---E GRKTTRSTLA VLPETVIYDV
TFDF2_RALEJ      ---------- -------HHG MRFVALPTTY A-GSEMTPIW GLTA-----D GAKRTGRDPR VLPSTVLYDP
TFDF1_RALEJ      ---------- -------NLD VPSLVIPTTY A-GSEMTTIW GVTE-----G GMKRTGRDPK VLPKTVIYDP
CLCE_PSESB       ---------- -------RTE LPIVAVPTTY A-GSEMTSIF GITE-----G GVKKTGRDAR VMPRAVIYEP
ADH1_CLOSA       DPF------- -TVPE-LRNK AKFLAIPSTS GTATEVTAFS VITDYK---T EIKYPLADFN ITPDVAVVDS
ADH2_ENTHI       QKFIDLRKRA FKFPT-MGKK ARLICIPTTS GTGSEVTPFA VISDHE---T GKKYPLADYS LTPSVAIVDP
ADHE_ECO57       LRFMDIRKRI YKFPK-MGVK AKMIAVTTTS GTGSEVTPFA VVTDDA---T GQKYPLADYA LTPDMAIVDA
MEDH_RHOER       ---------- -FAKSTNKEN PPHIAVSTTA GTGSEVTSWAY VITDTSDMNN PHKVGFDEA TIVTLAIDDP
EUTG_SALTY       ---------- --EHSTLRPR LPLIAVPTTA GTGSETTNVT VIIDAV---S GRKQVLAHAS LMPDVAILDA
EUTG_ECOLI       ---------- --ETSVLQPR LPLIAIPTTA GTGSETTNVT VIIDAV---S GRKQVLAHAS LMPDVAILDA
GBSB_BACSU       ---------- --KKPLENRI PPLTTIPTTA GTGSEVTQWA VITDE----R EPKFNTGGPL IAAHLTIIDP
FUCO_ECO57       ---------- --LSPTNKPS VPILAIPTTA GTAAEVTINY VITDEE---K RRKFVCVDPH DIPQVAFIDA
MEDH_BACMT       ---------- --VNSVEKPV VPVVAITTTA GTGSETTLS VITDSA---R KVKMPVIDEK ITPTVAIVDP
DHAT_CITFR       ---------- --IETLTNPL PPIVAVNTTA GTASEVTRHC VLTNTK---T KVKFVIVSWR NLPSVSINDP
DHAT_KLEPN       ---------- --IETLTNPL PPIVAVNTTA GTASEVTRHC VLTNTE---T KVKFVIVSWR NLPSVSINDP
ADH4_YEAST       ---------- --VNQSKKAA LPLFAINTTA GTASEMTRFT IISNEE---T K KIKMAIIDNN VTPAVAVNDP
ADH4_SCHPO       ---------- --VDKSSKPQ LPLIAINTTA GTASEMTRFA IITEET---R HIKMAIIDKH TMPILSVNDP
ADH2_ZYMMO       ---------- --IDKSKKPA LPLMSINTTA GTASEMTRFC IITDEV---R HVKMAIVDRH VTPMVSVNDP
ADH2_ECOLI       ---------- --VDRSAKPQ LPMIAINTTA GTASEMTRFC IITDEA---R HIKMAIVDKH VTPLLSVNDS
```

```
            211
4HDB_CLOKL  EFIKGLPYKF FVTSSVDALI HATEAYVSPN AN-PYTDMFS VKAMELILNG YMQMVEKG-N DYPVEIIEDF
YQHD_ECOLI  VYTYTLPPRQ VANGVVDAFV HTVEQYVTKP VEAKIQDRFA EGILLLTLIED GPKALKEP-E NYDVR--ANV
ADH3_ENTHI  CFTMSLPDNQ IRNGLVDSFV HCIEQYIGNY HLNPVVEAET EGVMRTIIGV SHHTLENH-Q DYQAR--ITF
ADHA_BACSU  VNTFTVPKNH TIYGMVDMMS HVFEQYFHHV SNTFYQDRMC ESLLRTVIET APKLINDL-E NYELR--ETI
ADHE_BACSU  ENTFTVPENQ TVYGNVDMMS HVFEQYPHHV ENTPLQDRMC FAVLQTVIET APKLLEDL-E NYELR--ETI
ADHB_CLOAB  TYTYTVPFNQ TRAGTADIMS HIPEVYFSHT KTAYLQDRMA EALLRTCIKY GGIALEKP-D DYEAR--ANL
ADHA_CLOAB  TYTFTVPKNQ TAAGTADIMS HTFESYPSGV EGAYVQDGIA EAILRTCIKY GKIAMEKT-D DYEAR--ANL
MACAI_RHOOP ELSKNLPVPI AVASAVNALA HAVEAMYSPD AN-PVVDTKA LEAAQALARG LRGLVSDP-S CRRIR--TDL
TFDF2_RALEJ HHLTSLPPEV TGPSGMNAIA HAVESMYAPD RN-PITMLLA EESIRAMAQG LPVAVDSP-G DLDAR--TRT
TFDF1_RALEJ LLTVDLPLAI SVTSALNAIA HAAEGLYSAD LN-PVLETMC KQGICALFDA IPELVAKF-T DAEAR--TDA
CLCE_PSESB  RLTLELPLSI SVTSAINAIA HAVEGLYAPD AT-PLLTIMA QEGIAATVRA ISRMYQSP-R DLQAR--GDA
ADH1_CLOSA  ELAETMPPKL TAHTGMDALT HAIEAYVATL HS-PFTDPLA MQAIEMINEH LFKSYE---G DKEAR--EQM
ADH2_ENTHI  MFTMSLPKRA IADTGLDVLV HATEAYVSVM AN-EYTDGLA REAVKLVFEN LLKSYN---G DLEAR--EKM
ADHE_ECO57  NLVMDMPKSL CAFGGLDAVT HAMEAYVSVL AS-EPSDGQA LQALKLLKEY LPASYHEGSK NPVAR--ERV
MEDH_RHOER  LLYYTCPQHF TAYCGFDVLA HGSEPFVSRL DF-APSLGNA IYSVELVAKN LREAVPEP-R NLKAR--EGM
EUTG_SALTY  AVTEGVPPNV TAMTGIDALT HAIEAYSALN AT-PFTDSLA IGAIAMIGKS LPKAVGYG-H DLAAR--ESM
EUTG_ECOLI  ALTEGVPSHV TAMTGIDALT HAIEAYSALN AT-PFTDSLA IGAIAMIGKS LPKAVGYG-H DLAAR--ESM
GBSB_BACSU  ELHVSMPPHV TAMTGIDALA HAIECYTMKF AQ-PITDAVA LMAIEYAAHY IKRAFADG-E DLEAR--YGM
FUCO_ECO57  DMMDGMPPAL KAATGVDALT HAIBGYITRG AW-ALTDALH IKAIEIIAGA LRGSVA---G DKDAG--EEM
MEDH_BACMT  ELMVKKPAGL TIATGMDALS HAIEAYVAKG AT-PVTDAPA IQAMKLINEY LPKAVANG-E DIEAR--EAM
DHAT_CITFR  LLMLGKPAPL TAATGMDALT HAVEAYISKD AN-PVTDAAA IQAIRLIARN LRQAVALG-S NLKAR--ENM
DHAT_KLEPN  LLMIGKPAAL TAATGMDALT HAVEAYISAD AN-PVTDAAA MQAIRLIARN LRQAVALG-S NLQAR--ENM
ADH4_YEAST  STMPGLPPAL TAATSLDALT HCIEAYVSTA SN-PITDACA LKGIDLINES LVAAYKDG-K DKKAR--TDM
ADH4_SCHPO  ETMYGLPPSL TAATGMDALT HAVEAYVSTA AN-PITDACA VKCIELVNKY LKRAVDNG-K DEEAR--DNM
ADH2_ZYMMO  LLNVGMPKGL TAATGMDALT HAFEAYSSTA AT-PITDACA LKAASMIAKN LKTACDNG-K DMPAR--EAM
ADH2_ECOLI  SLMIGMPKSL TAATGMDALT HAIEAYVSIA AT-PITDACA LKAVTMIAEN LPLAVEDG-S NAKAR--EAM 281
4HDB_CLOKL  VIGSNY---- ---------- AGIAFGNAGV GAVHALSYPI GGNYHVPHGE ANYLFFTEIF KIYY------
YQHD_ECOLI  MWAATQALN- ---------- GLIGAGVPQD WATHMLGHEL TAMHGLDHAQ TLAIVLPALW NEKR------
ADH3_ENTHI  CYAATVALNM SLLCGVTLCG GAHAVGHTLC GGAHAVGHEL GGAHAVGHEL TLAITTPGVM RFNK------
ADHA_BACSU  LYTGTIALN- ---------- GMLSMGARGD WATHNIEHAV SAVYDIPHAG GLAILFPNWM RHTL------
ADHB_BACSU  LYAGTIALN- ---------- GTLQMGYFGD WASHTMEHAV SAVYDIPHAG GLAILFPNWM RYTL------
ADHB_CLOAB  LYAGTIALN- ---------- GLLTYGKDTN WSCHPMEHEL SAYYDITHGV GLAILTPNWM EYIL------
ADHA_CLOAB  MWASSLAIN- ---------- GLLSLGKDRK WSCHPMEHEL SAYYDITHGV GLAILTPNWM EYIL------
MACAI_RHOOP LRGSWL---- ---------- AGMCLGSVGM AVHHKKLCHTL GGAFGLPHAP THTVVLPYAM SFNA------
TFDF2_RALEJ LYAAWL---- ---------- AGTVLGMVSM GLHHKKLCHVL GGRFNLPHAP MHAVLLPHVA AFNE------
TFDF1_RALEJ LFGAWM---- ---------- CGTALCHLGM GLHHKKLCHTL GGTLNLPHAB THAIVLPHAL AYNL------
CLCE_PSESB  LYGAWL---- ---------- CASVLGNVSM ALHHKKLCHTL GGTLDLPHAQ THTVVLPHAL AYNA------
ADH1_CLOSA  HYAQCL---- ---------- GICHSMAHKT GAVFHIPHGC ANAIYLPYVI KFNS------
ADH2_ENTHI  HNAATI---- ---------- AGMAPASAFL GMDHSMAHKV GAPFHLPHGR CVAVLLPHVI RYNG-QKPRK
ADHE_ECO57  HSAATI---- ---------- AGIAFANAPL GVCHSMAHKL GSQFHIPHGL ANALLICNVI RYNANDNPTK
MEDH_RHOER  MNAQYI---- ---------- AGQAFNSGGL GIVHSISHAV SAFFDSHHGL NNAIALPRVW EYNL------
EUTG_SALTY  LLASCM---- ---------- AGMAFSSAGL GLCHAMAHQP GAALHIPHGQ ANAMLLPTVM GFNR------
EUTG_ECOLI  LLASCM---- ---------- AGMAFSSAGL GLCHAMAHQP GAALHIPHGL ANAMLLPTVM EFNR------
GBSB_BACSU  AQAAML---- ---------- AGLSYGSESA GAAHAMSQTL GGIIPVAHGQ CVAPMMGPVM EYNW------
FUCC_ECO57  ALGQYV---- ---------- AGMGFSNVGL GLVHGMAHPL GAFYNTPHGV ANAILLPHVM RYNA------
MEDH_BACMT  AYAQYM---- ---------- AGVAFNNGGL GLVHSISHQV GGVYKLQHGI CNSVNMPHVC AFNL------
DHAT_CITFR  AYASLL---- ---------- AGMAFNNANL GYVHAMAHQL GGLYDMPHGV ANAVLLPHVA RYNL------
DHAT_KLEPN  AYASLL---- ---------- AGMAFNNANL GYVHAMAHQL GGLYDMPHGV ANAVLLPHVA RYNL------
ADH4_YEAST  CYAEYL---- ---------- AGMAFNNASL GYVHALAHQL GGFYHLPHGV CNAVLLPHVQ EANM------
ADH4_SCHPO  AYAEFL---- ---------- GGMAFNNASL GYVHAMAHQL GGPYGIPHGV CNAVLLAHVQ KFNS------
ADH2_ZYMMO  AYAQFL---- ---------- AGMAFNNASL GYVHAMAHQL GGYYNLPHGV CNAVLLPHVL AYNA------
ADH2_ECOLI  AYAQFL---- ---------- AGMAFNNASL GYVHAMAHQL GGFYNLPHGV CNAVLLPHVQ VPNS------

351
4HDB_CLOKL  ----------E --KNPNGKIK DVNKLLAGI- -----LKCDE SBAYDSLSQL LDK-LLSRKP LREYGMK---
YQHD_ECOLI  ----------D --TK-RAKLL QYAERVWNIT EG--SDDERI DAAIAATRNF FEQ-LGVPTH LSDYGLD---
ADH3_ENTHI  ----------E --KN-AKKLI QMGEQVFGI- -----KNSTP EAAIEATEKN FKS-IGMKTR LSEWGKG---
ADHA_BACSU  ----------S --EN-PARMK QLAVRVPDVE EAGKTDEEIA LEGIDKLSAF WTS-LGAPNR LADYDIN---
ADHB_BACSU  ----------D --TN-VGRFK NLMLNMFDID TEGKTDKEIA LEGIDKLSAF WTS-LGAPSR LADYNIG---
ADHB_CLOAB  ----------N --NDTIVYKPV EYGVNVWGID KE-KNHYDIA HQAIQKTRDY FVNVLGLPSR LRDVGIE---
ADHA_CLOAB  ----------N --DDTLHKFV SYGINVWGID KN-KDNYEIA REAIKNTREY FNS-LGIPSK LREVGIG---
MACAI_RHOOP ----------S --EV-PDVMD SLASAM-NV- -------SNA ---PAGVWDL IAD-AGGPTS LASLGLL---
TFDF2_RALEJ ----------V --AA-PAELG RVAAAL-GA- -------PGP GGAGAALHAL LRF-TCTERS LAAIGMP---
TFDF1_RALEJ ----------P --YA-APAER LLQEVA-GS- -------SDV ---PSALYDL ARN-AGAPLS LAEIGMR---
CLCE_PSESB  ----------R --AV-PDAMR VLRIAL-GH- -------DDP ---PTALYEL ARD-NGAPVA LRDLGMR---
ADH1_CLOSA  ----------K --TS-LERYA KIAKQI---S LAGNTNEELV DSLINLVKEL NKK-MQIPTT LKEYGIH---
ADH2_ENTHI  LAMWPKYNFY --KA-DQRYM ELAQMV-GLK C--NTPAEGV EAPAKACEEL MKA-TETITG FKKANID---
ADHE_ECO57  QTAFSQYDRP --QA-RRRYA EIADHL-GLS APGDRTAAKI EKLLAWLETL KAE-LGIPKS IREAGVQ---
MEDH_RHOER  ----------P --SR-YERYA QLAGAL-GVD TRNLTTVQAA DAAVEAAIRL AKD-VGIPDN FGQVRTDSYA
EUTG_SALTY  ----------M --VC-RERFS QIGPAL-TN- -----KKSDD RDAIAAVCEL IAE-VGQSKR LADAGAK---
EUTG_ECOLI  ----------M --VC-RERFS QIGRAL-RT- -----KKSDD RDAINAVSEL IAE-VGIGKR LGDVGAT---
GBSB_BACSU  ----------K --GY-PEKFA RIAKAF-GID TSKMTTEEAA KASVNWMYDL VED-LEVPT- LEEQGVS---
FUCO_ECO57  ----------D --FT-GEKYR DIARVM-GVK VEGMSLEEAR NAAVEAVFAL NRD-VGIPPH LRDVGVR---
MEDH_BACMT  ----------I --AK-TEREA HIRELL-GEN VSGLSTAAAA ERAIVALERY NKN-FGIPSG YAEMGVK---
DHAT_CITFR  ----------I --AN-PEKFA DIAEFM-GEN TDGLSTMDAA ELAIHAIARL SAD-IGIPQH LRDLGVK---
DHAT_KLEPN  ----------I --AN-PEKFA DIAELM-GEN ITGLSTLDAA EKAIAAITRL SMD-IGIPQH LRDLGVK---
ADH4_YEAST  ----------Q CPKA-KKRLG EIALHF-GA- -----SQEDP EETIKALHVL NRT-MNIPRN LKELGVK---
ADH4_SCHPO  ----------R DPRA-NARLG DIAFHL-GC- -----EEHTA EAALDRISQL VLE-VKIRPH LVDLGVK---
ADH2_ZYMMO  ----------S --VV-AGRLK DVGVAM-GLD IANLGDKEGA EATIQAVRDL AAS-IGIPAN LTELGAK---
ADH2_ECOLI  ----------K --VA-AARLR DCAAAM-GVN VTGKNDAEGA EACINAIREL AKK-VDIPAG LRDLNVK---
```

Fig. 1 (end)

SEQUENCE LISTING

<160> NUMBER OF SEQ ID NOS: 80

<210> SEQ ID NO 1
<211> LENGTH: 387
<212> TYPE: PRT
<213> ORGANISM: Escherichia coli

<400> SEQUENCE: 1

```
Met Asn Asn Phe Asn Leu His Thr Pro Thr Arg Ile Leu Phe Gly Lys
1               5                   10                  15

Gly Ala Ile Ala Gly Leu Arg Glu Gln Ile Pro His Asp Ala Arg Val
            20                  25                  30

Leu Ile Thr Tyr Gly Gly Gly Ser Val Lys Lys Thr Gly Val Leu Asp
        35                  40                  45

Gln Val Leu Asp Ala Leu Lys Gly Met Asp Val Leu Glu Phe Gly Gly
    50                  55                  60

Ile Glu Pro Asn Pro Ala Tyr Glu Thr Leu Met Asn Ala Val Lys Leu
65                  70                  75                  80

Val Arg Glu Gln Lys Val Thr Phe Leu Leu Ala Val Gly Gly Gly Ser
                85                  90                  95

Val Leu Asp Gly Thr Lys Phe Ile Ala Ala Ala Asn Tyr Pro Glu
                100                 105                 110

Asn Ile Asp Pro Trp His Ile Leu Gln Thr Gly Gly Lys Glu Ile Lys
            115                 120                 125

Ser Ala Ile Pro Met Gly Cys Val Leu Thr Leu Pro Ala Thr Gly Ser
    130                 135                 140

Glu Ser Asn Ala Glu Ala Val Ile Ser Arg Lys Thr Thr Gly Asp Lys
145                 150                 155                 160

Gln Ala Phe His Ser Ala His Val Gln Pro Val Phe Ala Val Leu Asp
                165                 170                 175

Pro Val Tyr Thr Tyr Thr Leu Pro Pro Arg Gln Val Ala Asn Gly Val
                180                 185                 190

Val Asp Ala Phe Val His Thr Val Glu Gln Tyr Val Thr Lys Pro Val
            195                 200                 205

Asp Ala Lys Ile Gln Asp Arg Phe Ala Glu Gly Ile Leu Leu Thr Leu
    210                 215                 220

Ile Glu Asp Gly Pro Lys Ala Leu Lys Glu Pro Glu Asn Tyr Asp Val
225                 230                 235                 240

Arg Ala Asn Val Met Trp Ala Ala Thr Gln Ala Leu Asn Gly Leu Ile
                245                 250                 255

Gly Ala Gly Val Pro Gln Asp Trp Ala Thr His Met Leu Gly His Glu
                260                 265                 270

Leu Thr Ala Met His Gly Leu Asp His Ala Gln Thr Leu Ala Ile Val
    275                 280                 285

Leu Pro Ala Leu Trp Asn Glu Lys Arg Asp Thr Lys Arg Ala Lys Leu
    290                 295                 300

Leu Gln Tyr Ala Glu Arg Val Trp Asn Ile Thr Glu Gly Ser Asp Asp
305                 310                 315                 320

Glu Arg Ile Asp Ala Ala Ile Ala Ala Thr Arg Asn Phe Phe Glu Gln
                325                 330                 335

Leu Gly Val Pro Thr His Leu Ser Asp Tyr Gly Leu Asp Gly Ser Ser
                340                 345                 350

Ile Pro Ala Leu Leu Lys Lys Leu Glu Glu His Gly Met Thr Gln Leu
    355                 360                 365
```

Gly Glu Asn His Asp Ile Thr Leu Asp Val Ser Arg Arg Ile Tyr Glu
            370                 375                 380

Ala Ala Arg
385

<210> SEQ ID NO 2
<211> LENGTH: 387
<212> TYPE: PRT
<213> ORGANISM: Escherichia coli

<400> SEQUENCE: 2

Met Asn Asn Phe Asn Leu His Thr Pro Thr Arg Ile Leu Phe Gly Lys
1               5                   10                  15

Gly Ala Ile Ala Gly Leu Arg Glu Gln Ile Pro His Asp Ala Arg Val
            20                  25                  30

Leu Ile Thr Tyr Gly Gly Gly Ser Val Lys Lys Thr Gly Val Leu Asp
        35                  40                  45

Gln Val Leu Asp Ala Leu Lys Gly Met Asp Val Leu Glu Phe Gly Gly
    50                  55                  60

Ile Glu Pro Asn Pro Ala Tyr Glu Thr Leu Met Asn Ala Val Lys Leu
65                  70                  75                  80

Val Arg Glu Gln Lys Val Thr Phe Leu Leu Ala Val Gly Gly Gly Ser
                85                  90                  95

Val Leu Asp Gly Thr Lys Phe Ile Ala Ala Ala Asn Tyr Pro Glu
            100                 105                 110

Asn Ile Asp Pro Trp His Ile Leu Gln Thr Gly Gly Lys Glu Ile Lys
        115                 120                 125

Ser Ala Ile Pro Met Gly Cys Val Leu Thr Leu Pro Ala Thr Gly Ser
    130                 135                 140

Glu Ser Asn Ala Ser Ala Val Ile Ser Arg Lys Thr Thr Gly Asp Lys
145                 150                 155                 160

Gln Ala Phe His Ser Ala His Val Gln Pro Val Phe Ala Val Leu Asp
                165                 170                 175

Pro Val Tyr Thr Tyr Thr Leu Pro Pro Arg Gln Val Ala Asn Gly Val
            180                 185                 190

Val Asp Ala Phe Val His Thr Val Glu Gln Tyr Val Thr Lys Pro Val
        195                 200                 205

Asp Ala Lys Ile Gln Asp Arg Phe Ala Glu Gly Ile Leu Leu Thr Leu
    210                 215                 220

Ile Glu Asp Gly Pro Lys Ala Leu Lys Glu Pro Glu Asn Tyr Asp Val
225                 230                 235                 240

Arg Ala Asn Val Met Trp Ala Ala Thr Gln Ala Leu Asn Gly Leu Ile
                245                 250                 255

Gly Ala Gly Val Pro Gln Asp Trp Ala Thr His Met Leu Gly His Glu
            260                 265                 270

Leu Thr Ala Met His Gly Leu Asp His Ala Gln Thr Leu Ala Ile Val
        275                 280                 285

Leu Pro Ala Leu Trp Asn Glu Lys Arg Asp Thr Lys Arg Ala Lys Leu
    290                 295                 300

Leu Gln Tyr Ala Glu Arg Val Trp Asn Ile Thr Glu Gly Ser Asp Asp
305                 310                 315                 320

Glu Arg Ile Asp Ala Ala Ile Ala Ala Thr Arg Asn Phe Phe Glu Gln
                325                 330                 335

Leu Gly Val Pro Thr His Leu Ser Asp Tyr Gly Leu Asp Gly Ser Ser
            340                 345                 350

Ile Pro Ala Leu Leu Lys Lys Leu Glu Glu His Gly Met Thr Gln Leu
            355                 360                 365

Gly Glu Asn His Asp Ile Thr Leu Asp Val Ser Arg Arg Ile Tyr Glu
        370                 375                 380

Ala Ala Arg
385

<210> SEQ ID NO 3
<211> LENGTH: 387
<212> TYPE: PRT
<213> ORGANISM: Escherichia coli

<400> SEQUENCE: 3

Met Asn Asn Phe Asn Leu His Thr Pro Thr Arg Ile Leu Phe Gly Lys
1               5                   10                  15

Gly Ala Ile Ala Gly Leu Arg Glu Gln Ile Pro His Asp Ala Arg Val
            20                  25                  30

Leu Ile Thr Tyr Gly Gly Gly Ser Val Lys Lys Thr Gly Val Leu Asp
        35                  40                  45

Gln Val Leu Asp Ala Leu Lys Gly Met Asp Val Leu Glu Phe Gly Gly
    50                  55                  60

Ile Glu Pro Asn Pro Ala Tyr Glu Thr Leu Met Asn Ala Val Lys Leu
65                  70                  75                  80

Val Arg Glu Gln Lys Val Thr Phe Leu Leu Ala Val Gly Gly Gly Ser
                85                  90                  95

Val Leu Asp Gly Thr Lys Phe Ile Ala Ala Ala Asn Tyr Pro Glu
            100                 105                 110

Asn Ile Asp Pro Trp His Ile Leu Gln Thr Gly Gly Lys Glu Ile Lys
        115                 120                 125

Ser Ala Ile Pro Met Gly Cys Val Leu Thr Leu Pro Ala Thr Gly Ser
130                 135                 140

Glu Ser Asn Ala Ser Ala Val Ile Ser Arg Lys Thr Thr Gly Asp Lys
145                 150                 155                 160

Gln Ala Phe His Ser Ala His Val Gln Pro Val Phe Ala Val Leu Asp
                165                 170                 175

Pro Val Tyr Thr Tyr Thr Leu Pro Pro Arg Gln Val Ala Asn Gly Val
            180                 185                 190

Val Asp Ala Phe Val His Thr Val Glu Gln Tyr Val Thr Lys Pro Val
        195                 200                 205

Asp Ala Lys Ile Gln Asp Arg Phe Ala Glu Gly Ile Leu Leu Thr Leu
    210                 215                 220

Ile Glu Asp Gly Pro Lys Ala Leu Lys Glu Pro Glu Asn Tyr Asp Val
225                 230                 235                 240

Arg Ala Asn Val Met Trp Ala Ala Thr Gln Ala Leu Asn Gly Leu Ile
                245                 250                 255

Gly Ala Gly Val Pro Gln Asp Trp Ala Thr His Met Leu Gly His Glu
            260                 265                 270

Leu Thr Ala Met His Gly Leu Asp His Ala Gln Thr Leu Thr Ile Val
        275                 280                 285

Leu Pro Ala Leu Trp Asn Glu Lys Arg Asp Thr Lys Arg Ala Lys Leu
    290                 295                 300

Leu Gln Tyr Ala Glu Arg Val Trp Asn Ile Thr Glu Gly Ser Asp Asp
305                 310                 315                 320

Glu Arg Ile Asp Ala Ala Ile Ala Ala Thr Arg Asn Phe Phe Glu Gln

```
              325                 330                 335
Leu Gly Val Pro Thr His Leu Ser Asp Tyr Gly Leu Asp Gly Ser Ser
        340                 345                 350

Ile Pro Ala Leu Leu Lys Lys Leu Glu Glu His Gly Met Thr Gln Leu
            355                 360                 365

Gly Glu Asn His Asp Ile Thr Leu Asp Val Ser Arg Arg Ile Tyr Glu
        370                 375                 380

Ala Ala Arg
385

<210> SEQ ID NO 4
<211> LENGTH: 43
<212> TYPE: DNA
<213> ORGANISM: Artificial Sequence
<220> FEATURE:
<223> OTHER INFORMATION: Oligonucleotide

<400> SEQUENCE: 4
cgatgcacgt catgaacaac tttaatctgc acaccccaac ccg                43

<210> SEQ ID NO 5
<211> LENGTH: 70
<212> TYPE: DNA
<213> ORGANISM: Artificial Sequence
<220> FEATURE:
<223> OTHER INFORMATION: Oligonucleotide

<400> SEQUENCE: 5
ggcgtaaaaa gcttagcggg cggcttcgta tatacggcgg ctgacatcca acgtaatgtc    60
gtgattttcg                                                          70

<210> SEQ ID NO 6
<211> LENGTH: 42
<212> TYPE: DNA
<213> ORGANISM: Artificial Sequence
<220> FEATURE:
<223> OTHER INFORMATION: Oligonucleotide

<400> SEQUENCE: 6
ggttcagaat ccaacgcaga agcggtgata tcccgtaaaa cc                 42

<210> SEQ ID NO 7
<211> LENGTH: 42
<212> TYPE: DNA
<213> ORGANISM: Artificial Sequence
<220> FEATURE:
<223> OTHER INFORMATION: Oligonucleotide

<400> SEQUENCE: 7
ggttttacgg gatatcaccg cttctgcgtt ggattctgaa cc                 42

<210> SEQ ID NO 8
<211> LENGTH: 48
<212> TYPE: DNA
<213> ORGANISM: Artificial Sequence
<220> FEATURE:
<223> OTHER INFORMATION: Oligonucleotide

<400> SEQUENCE: 8
ggttcagaat ccaacgcaag cgcggtgata tcccgtaaaa ccacaggc           48

<210> SEQ ID NO 9
<211> LENGTH: 48
```

<212> TYPE: DNA
<213> ORGANISM: Artificial Sequence
<220> FEATURE:
<223> OTHER INFORMATION: Oligonucleotide

<400> SEQUENCE: 9
gcctgtggtt ttacgggata tcaccgcgct tgcgttggat tctgaacc               48

<210> SEQ ID NO 10
<211> LENGTH: 55
<212> TYPE: DNA
<213> ORGANISM: Artificial Sequence
<220> FEATURE:
<223> OTHER INFORMATION: Oligonucleotide

<400> SEQUENCE: 10
gatcacgcgc aaacactgac tatagtactg cctgcactgt ggaatgaaaa acgcg       55

<210> SEQ ID NO 11
<211> LENGTH: 55
<212> TYPE: DNA
<213> ORGANISM: Artificial Sequence
<220> FEATURE:
<223> OTHER INFORMATION: Oligonucleotide

<400> SEQUENCE: 11
cgcgtttttc attccacagt gcaggcagta ctatagtcag tgtttgcgcg tgatc       55

<210> SEQ ID NO 12
<211> LENGTH: 24
<212> TYPE: DNA
<213> ORGANISM: Artificial Sequence
<220> FEATURE:
<223> OTHER INFORMATION: Oligonucleotide

<400> SEQUENCE: 12
ccgacagtaa gacgggtaag cctg                                        24

<210> SEQ ID NO 13
<211> LENGTH: 22
<212> TYPE: DNA
<213> ORGANISM: Artificial Sequence
<220> FEATURE:
<223> OTHER INFORMATION: Oligonucleotide

<400> SEQUENCE: 13
agcttagtaa agccctcgct ag                                          22

<210> SEQ ID NO 14
<211> LENGTH: 100
<212> TYPE: DNA
<213> ORGANISM: Artificial Sequence
<220> FEATURE:
<223> OTHER INFORMATION: Oligonucleotide

<400> SEQUENCE: 14
catgggctag ctacgtatta attaaagatc tcctagggag ctcaccggtt aaaaataaga   60
gttaccttaa atggtaactc ttatttttt aggcgcgcca                       100

<210> SEQ ID NO 15
<211> LENGTH: 100
<212> TYPE: DNA
<213> ORGANISM: Artificial Sequence
<220> FEATURE:
<223> OTHER INFORMATION: Oligonucleotide -continued

<400> SEQUENCE: 15
agcttggcgc gcctaaaaaa ataagagtta ccatttaagg taactcttat ttttaaccgg    60
tgagctccct aggagatctt taattaatac gtagctagcc                         100

<210> SEQ ID NO 16
<211> LENGTH: 43
<212> TYPE: DNA
<213> ORGANISM: Artificial Sequence
<220> FEATURE:
<223> OTHER INFORMATION: Oligonucleotide

<400> SEQUENCE: 16
cgatgcacgt catgaacaac tttaatctgc acaccccaac ccg                      43

<210> SEQ ID NO 17
<211> LENGTH: 29
<212> TYPE: DNA
<213> ORGANISM: Artificial Sequence
<220> FEATURE:
<223> OTHER INFORMATION: Oligonucleotide

<400> SEQUENCE: 17
ctagctagct tagcgggcgg cttcgtata                                      29

<210> SEQ ID NO 18
<211> LENGTH: 45
<212> TYPE: DNA
<213> ORGANISM: Artificial Sequence
<220> FEATURE:
<223> OTHER INFORMATION: Oligonucleotide

<400> SEQUENCE: 18
gacaccaaaa tcgtcgctgg cacacctgca cgtctgctag cggcg                    45

<210> SEQ ID NO 19
<211> LENGTH: 45
<212> TYPE: DNA
<213> ORGANISM: Artificial Sequence
<220> FEATURE:
<223> OTHER INFORMATION: Oligonucleotide

<400> SEQUENCE: 19
cgccgctagc agacgtgcag gtgtgccagc gacgattttg gtgtc                    45

<210> SEQ ID NO 20
<211> LENGTH: 105
<212> TYPE: DNA
<213> ORGANISM: Artificial Sequence
<220> FEATURE:
<223> OTHER INFORMATION: Oligonucleotide

<400> SEQUENCE: 20
gttaactacg gatgtacatt atggaactga cgactcgcac tttacctgcg cggaaacata    60
ttgcgctggt ggcacacgat caggcctggt gatgatggcg ggatc                   105

<210> SEQ ID NO 21
<211> LENGTH: 120
<212> TYPE: DNA
<213> ORGANISM: Artificial Sequence
<220> FEATURE:
<223> OTHER INFORMATION: Oligonucleotide

<400> SEQUENCE: 21
gggaaattaa gttaccggta gtgcctgttg catacagtac gtgttgttcc agtaacggtt    60

```
gatgccgttc acccagctc atcagcatct gtttgcattc agaagaactc gtcaagaagg        120
```

<210> SEQ ID NO 22
<211> LENGTH: 100
<212> TYPE: DNA
<213> ORGANISM: Artificial Sequence
<220> FEATURE:
<223> OTHER INFORMATION: Oligonucleotide

<400> SEQUENCE: 22

```
tccagtcgcc gcatttcaac gacgcggtcg atattctgat ccccgattat cagcgttatc        60
tcgcggaccg tctgaagtaa tgtaggctgg agctgcttcg                              100
```

<210> SEQ ID NO 23
<211> LENGTH: 100
<212> TYPE: DNA
<213> ORGANISM: Artificial Sequence
<220> FEATURE:
<223> OTHER INFORMATION: Oligonucleotide

<400> SEQUENCE: 23

```
tgtggaaata ctgaaaaatc tggatgtgcc ggtggcgaga aaaccgtaag aaacaggtgg        60
cgtttgccac ctgtgcaata catatgaata tcctccttag                              100
```

<210> SEQ ID NO 24
<211> LENGTH: 48
<212> TYPE: DNA
<213> ORGANISM: Artificial Sequence
<220> FEATURE:
<223> OTHER INFORMATION: Oligonucleotide

<400> SEQUENCE: 24

```
ggttcagaat ccaacgcaga agcggtgata tcccgtaaaa ccacaggc                     48
```

<210> SEQ ID NO 25
<211> LENGTH: 48
<212> TYPE: DNA
<213> ORGANISM: Artificial Sequence
<220> FEATURE:
<223> OTHER INFORMATION: Oligonucleotide

<400> SEQUENCE: 25

```
gcctgtggtt ttacgggata tcaccgcttc tgcgttggat tctgaacc                     48
```

<210> SEQ ID NO 26
<211> LENGTH: 41
<212> TYPE: DNA
<213> ORGANISM: Artificial Sequence
<220> FEATURE:
<223> OTHER INFORMATION: synthetic short Ptrc01 promoter

<400> SEQUENCE: 26

```
gagctgttga ctattaatca tccggctcga ataatgtgtg g                            41
```

<210> SEQ ID NO 27
<211> LENGTH: 36
<212> TYPE: DNA
<213> ORGANISM: Artificial Sequence
<220> FEATURE:
<223> OTHER INFORMATION: Oligonucleotide

<400> SEQUENCE: 27

```
ttacgtaccc agcaaaggga gcaagtaatg aacaac                                  36
```

<210> SEQ ID NO 28
<211> LENGTH: 32
<212> TYPE: DNA
<213> ORGANISM: Artificial Sequence
<220> FEATURE:
<223> OTHER INFORMATION: Oligonucleotide

<400> SEQUENCE: 28
aagatcttct tagcgggcgg cttcgtatat ac                                32

<210> SEQ ID NO 29
<211> LENGTH: 61
<212> TYPE: DNA
<213> ORGANISM: Artificial Sequence
<220> FEATURE:
<223> OTHER INFORMATION: Oligonucleotide

<400> SEQUENCE: 29
atgcttgctg tcagaagatt aacaagatac acattcctta gtttatcatt atcaatactc    60
g                                                                   61

<210> SEQ ID NO 30
<211> LENGTH: 23
<212> TYPE: DNA
<213> ORGANISM: Artificial Sequence
<220> FEATURE:
<223> OTHER INFORMATION: Oligonucleotide

<400> SEQUENCE: 30
atcctcgaaa ctaagttctt ggt                                           23

<210> SEQ ID NO 31
<211> LENGTH: 42
<212> TYPE: DNA
<213> ORGANISM: Artificial Sequence
<220> FEATURE:
<223> OTHER INFORMATION: Oligonucleotide

<400> SEQUENCE: 31
aaacaccaga acttagtttc gaactagttt attcccactc tt                      42

<210> SEQ ID NO 32
<211> LENGTH: 62
<212> TYPE: DNA
<213> ORGANISM: Artificial Sequence
<220> FEATURE:
<223> OTHER INFORMATION: Oligonucleotide

<400> SEQUENCE: 32
tgaaatataa ataacgttct taatactaac ataactataa actagtatgg accgcattat    60
tc                                                                  62

<210> SEQ ID NO 33
<211> LENGTH: 66
<212> TYPE: DNA
<213> ORGANISM: Artificial Sequence
<220> FEATURE:
<223> OTHER INFORMATION: Oligonucleotide

<400> SEQUENCE: 33
cctggatgta tttacccggt gattgaataa tgcggtccat actagtttat agttatgtta    60
gtatta                                                              66

```
<210> SEQ ID NO 34
<211> LENGTH: 60
<212> TYPE: DNA
<213> ORGANISM: Artificial Sequence
<220> FEATURE:
<223> OTHER INFORMATION: Oligonucleotide

<400> SEQUENCE: 34
gaggcaagct aaacagatct ctagacctag gtacccgccg gcaaattaaa gccttcgagc      60

<210> SEQ ID NO 35
<211> LENGTH: 62
<212> TYPE: DNA
<213> ORGANISM: Artificial Sequence
<220> FEATURE:
<223> OTHER INFORMATION: Oligonucleotide

<400> SEQUENCE: 35
gcttgagaag gttttgggac gctcgaaggc tttaatttgc taggtctaga gatctgttta      60
gc                                                                    62

<210> SEQ ID NO 36
<211> LENGTH: 64
<212> TYPE: DNA
<213> ORGANISM: Artificial Sequence
<220> FEATURE:
<223> OTHER INFORMATION: Oligonucleotide

<400> SEQUENCE: 36
ctattcgtca tcgatgtcta gctcttcaat catctccggt ccactagtgg atctgatatc      60
acct                                                                  64

<210> SEQ ID NO 37
<211> LENGTH: 20
<212> TYPE: DNA
<213> ORGANISM: Artificial Sequence
<220> FEATURE:
<223> OTHER INFORMATION: Oligonucleotide

<400> SEQUENCE: 37
atgcttgctg tcagaagatt                                                 20

<210> SEQ ID NO 38
<211> LENGTH: 20
<212> TYPE: DNA
<213> ORGANISM: Artificial Sequence
<220> FEATURE:
<223> OTHER INFORMATION: Oligonucleotide

<400> SEQUENCE: 38
tagtatggac cgcattattc                                                 20

<210> SEQ ID NO 39
<211> LENGTH: 60
<212> TYPE: DNA
<213> ORGANISM: Artificial Sequence
<220> FEATURE:
<223> OTHER INFORMATION: Oligonucleotide

<400> SEQUENCE: 39
atgtctgccc ctaagaagat cgtcgttttg ccaggtgacc agctggagct catagcttca      60

<210> SEQ ID NO 40
<211> LENGTH: 60
<212> TYPE: DNA
```

```
<213> ORGANISM: Artificial Sequence
<220> FEATURE:
<223> OTHER INFORMATION: Oligonucleotide

<400> SEQUENCE: 40
tgcgggttgg ggtgtgcaga ttaaagttgt tcatactagt ggatccacta gttctagaaa      60

<210> SEQ ID NO 41
<211> LENGTH: 60
<212> TYPE: DNA
<213> ORGANISM: Artificial Sequence
<220> FEATURE:
<223> OTHER INFORMATION: Oligonucleotide

<400> SEQUENCE: 41
catagcaatc taatctaagt tttctagaac tagtggatcc actagtatga caaactttaa      60

<210> SEQ ID NO 42
<211> LENGTH: 60
<212> TYPE: DNA
<213> ORGANISM: Artificial Sequence
<220> FEATURE:
<223> OTHER INFORMATION: Oligonucleotide

<400> SEQUENCE: 42
tgaaatataa ataacgttct taatactaac ataactataa actagtttag cgggcggctt      60

<210> SEQ ID NO 43
<211> LENGTH: 60
<212> TYPE: DNA
<213> ORGANISM: Artificial Sequence
<220> FEATURE:
<223> OTHER INFORMATION: Oligonucleotide

<400> SEQUENCE: 43
tgtcagccgc cgtatatacg aagccgcccg ctaaactagt ttatagttat gttagtatta      60

<210> SEQ ID NO 44
<211> LENGTH: 60
<212> TYPE: DNA
<213> ORGANISM: Artificial Sequence
<220> FEATURE:
<223> OTHER INFORMATION: Oligonucleotide

<400> SEQUENCE: 44
ctccatgtcg ctggccgggt gacccggcgg ggacgaggca gcaaattaaa gccttcgagc      60

<210> SEQ ID NO 45
<211> LENGTH: 60
<212> TYPE: DNA
<213> ORGANISM: Artificial Sequence
<220> FEATURE:
<223> OTHER INFORMATION: Oligonucleotide

<400> SEQUENCE: 45
gcttgagaag gttttgggac gctcgaaggc tttaatttgc tgcctcgtcc ccgccgggtc      60

<210> SEQ ID NO 46
<211> LENGTH: 60
<212> TYPE: DNA
<213> ORGANISM: Artificial Sequence
<220> FEATURE:
<223> OTHER INFORMATION: Oligonucleotide

<400> SEQUENCE: 46
ttaagcaagg attttcttaa cttcttcggc gacagcatca cagtatagcg accagcattc      60
```

<210> SEQ ID NO 47
<211> LENGTH: 21
<212> TYPE: DNA
<213> ORGANISM: Artificial Sequence
<220> FEATURE:
<223> OTHER INFORMATION: Oligonucleotide

<400> SEQUENCE: 47
atgtctgccc ctaagaagat c                                                  21

<210> SEQ ID NO 48
<211> LENGTH: 20
<212> TYPE: DNA
<213> ORGANISM: Artificial Sequence
<220> FEATURE:
<223> OTHER INFORMATION: Oligonucleotide

<400> SEQUENCE: 48
actagtttag cgggcggctt                                                    20

<210> SEQ ID NO 49
<211> LENGTH: 60
<212> TYPE: DNA
<213> ORGANISM: Artificial Sequence
<220> FEATURE:
<223> OTHER INFORMATION: Oligonucleotide

<400> SEQUENCE: 49
atgtcgaaag ctacatataa ggaacgtgct gctactcatc gccagatctg tttagcttgc         60

<210> SEQ ID NO 50
<211> LENGTH: 40
<212> TYPE: DNA
<213> ORGANISM: Artificial Sequence
<220> FEATURE:
<223> OTHER INFORMATION: Oligonucleotide

<400> SEQUENCE: 50
gtgcgagtcg tcagttccat aatacgcaaa ccgcctctcc                              40

<210> SEQ ID NO 51
<211> LENGTH: 40
<212> TYPE: DNA
<213> ORGANISM: Artificial Sequence
<220> FEATURE:
<223> OTHER INFORMATION: Oligonucleotide

<400> SEQUENCE: 51
ggagaggcgg tttgcgtatt atggaactga cgactcgcac                              40

<210> SEQ ID NO 52
<211> LENGTH: 60
<212> TYPE: DNA
<213> ORGANISM: Artificial Sequence
<220> FEATURE:
<223> OTHER INFORMATION: Oligonucleotide

<400> SEQUENCE: 52
ttagttttgc tggccgcatc ttctcaaata tgcttccctt tacttcagac ggtccgcgag         60

<210> SEQ ID NO 53
<211> LENGTH: 18
<212> TYPE: DNA
<213> ORGANISM: Artificial Sequence
<220> FEATURE:

-continued

<223> OTHER INFORMATION: Oligonucleotide

<400> SEQUENCE: 53
ggaactgacg actcgcac                                                 18

<210> SEQ ID NO 54
<211> LENGTH: 20
<212> TYPE: DNA
<213> ORGANISM: Artificial Sequence
<220> FEATURE:
<223> OTHER INFORMATION: Oligonucleotide

<400> SEQUENCE: 54
ttagtttcta gagttgatga                                               20

<210> SEQ ID NO 55
<211> LENGTH: 371
<212> TYPE: PRT
<213> ORGANISM: Clostridium kluyveri

<400> SEQUENCE: 55

Met Lys Leu Leu Lys Leu Ala Pro Asp Val Tyr Lys Phe Asp Thr Ala
1               5                   10                  15

Glu Glu Phe Met Lys Tyr Phe Lys Val Gly Lys Gly Asp Phe Ile Leu
            20                  25                  30

Thr Asn Glu Phe Leu Tyr Lys Pro Phe Leu Glu Lys Phe Asn Asp Gly
        35                  40                  45

Ala Asp Ala Val Phe Gln Glu Lys Tyr Gly Leu Gly Glu Pro Ser Asp
    50                  55                  60

Glu Met Ile Asn Asn Ile Ile Lys Asp Ile Gly Asp Lys Gln Tyr Asn
65                  70                  75                  80

Arg Ile Ile Ala Val Gly Gly Gly Ser Val Ile Asp Ile Ala Lys Ile
                85                  90                  95

Leu Ser Leu Lys Tyr Thr Asp Asp Ser Leu Asp Leu Phe Glu Gly Lys
            100                 105                 110

Val Pro Leu Val Lys Asn Lys Glu Leu Ile Ile Val Pro Thr Thr Cys
        115                 120                 125

Gly Thr Gly Ser Glu Val Thr Asn Val Ser Val Ala Glu Leu Lys Arg
    130                 135                 140

Arg His Thr Lys Lys Gly Ile Ala Ser Asp Glu Leu Tyr Ala Thr Tyr
145                 150                 155                 160

Ala Val Leu Val Pro Glu Phe Ile Lys Gly Leu Pro Tyr Lys Phe Phe
                165                 170                 175

Val Thr Ser Ser Val Asp Ala Leu Ile His Ala Thr Glu Ala Tyr Val
            180                 185                 190

Ser Pro Asn Ala Asn Pro Tyr Thr Asp Met Phe Ser Val Lys Ala Met
        195                 200                 205

Glu Leu Ile Leu Asn Gly Tyr Met Gln Met Val Glu Lys Gly Asn Asp
    210                 215                 220

Tyr Arg Val Glu Ile Ile Glu Asp Phe Val Ile Gly Ser Asn Tyr Ala
225                 230                 235                 240

Gly Ile Ala Phe Gly Asn Ala Gly Val Gly Ala Val His Ala Leu Ser
                245                 250                 255

Tyr Pro Ile Gly Gly Asn Tyr His Val Pro His Gly Glu Ala Asn Tyr
            260                 265                 270

Leu Phe Phe Thr Glu Ile Phe Lys Thr Tyr Tyr Glu Lys Asn Pro Asn
        275                 280                 285

```
Gly Lys Ile Lys Asp Val Asn Lys Leu Leu Ala Gly Ile Leu Lys Cys
        290                 295                 300

Asp Glu Ser Glu Ala Tyr Asp Ser Leu Ser Gln Leu Leu Asp Lys Leu
305                 310                 315                 320

Leu Ser Arg Lys Pro Leu Arg Glu Tyr Gly Met Lys Glu Glu Glu Ile
                325                 330                 335

Glu Thr Phe Ala Asp Ser Val Ile Glu Gly Gln Gln Arg Leu Leu Val
            340                 345                 350

Asn Asn Tyr Glu Pro Phe Ser Arg Glu Asp Ile Val Asn Thr Tyr Lys
        355                 360                 365

Lys Leu Tyr
    370

<210> SEQ ID NO 56
<211> LENGTH: 387
<212> TYPE: PRT
<213> ORGANISM: Escherichia coli

<400> SEQUENCE: 56

Met Asn Asn Phe Asn Leu His Thr Pro Thr Arg Ile Leu Phe Gly Lys
1               5                   10                  15

Gly Ala Ile Ala Gly Leu Arg Glu Gln Ile Pro His Asp Ala Arg Val
            20                  25                  30

Leu Ile Thr Tyr Gly Gly Gly Ser Val Lys Lys Thr Gly Val Leu Asp
        35                  40                  45

Gln Val Leu Asp Ala Leu Lys Gly Met Asp Val Leu Glu Phe Gly Gly
    50                  55                  60

Ile Glu Pro Asn Pro Ala Tyr Glu Thr Leu Met Asn Ala Val Lys Leu
65                  70                  75                  80

Val Arg Glu Gln Lys Val Thr Phe Leu Leu Ala Val Gly Gly Gly Ser
                85                  90                  95

Val Leu Asp Gly Thr Lys Phe Ile Ala Ala Ala Ala Asn Tyr Pro Glu
            100                 105                 110

Asn Ile Asp Pro Trp His Ile Leu Gln Thr Gly Gly Lys Glu Ile Lys
        115                 120                 125

Ser Ala Ile Pro Met Gly Cys Val Leu Thr Leu Pro Ala Thr Gly Ser
    130                 135                 140

Glu Ser Asn Ala Gly Ala Val Ile Ser Arg Lys Thr Thr Gly Asp Lys
145                 150                 155                 160

Gln Ala Phe His Ser Ala His Val Gln Pro Val Phe Ala Val Leu Asp
                165                 170                 175

Pro Val Tyr Thr Tyr Thr Leu Pro Pro Arg Gln Val Ala Asn Gly Val
            180                 185                 190

Val Asp Ala Phe Val His Thr Val Glu Gln Tyr Val Thr Lys Pro Val
        195                 200                 205

Asp Ala Lys Ile Gln Asp Arg Phe Ala Glu Gly Ile Leu Leu Thr Leu
    210                 215                 220

Ile Glu Asp Gly Pro Lys Ala Leu Lys Glu Pro Glu Asn Tyr Asp Val
225                 230                 235                 240

Arg Ala Asn Val Met Trp Ala Ala Thr Gln Ala Leu Asn Gly Leu Ile
                245                 250                 255

Gly Ala Gly Val Pro Gln Asp Trp Ala Thr His Met Leu Gly His Glu
            260                 265                 270

Leu Thr Ala Met His Gly Leu Asp His Ala Gln Thr Leu Ala Ile Val
```

```
                275                 280                 285
Leu Pro Ala Leu Trp Asn Glu Lys Arg Asp Thr Lys Arg Ala Lys Leu
290                 295                 300

Leu Gln Tyr Ala Glu Arg Val Trp Asn Ile Thr Glu Gly Ser Asp Asp
305                 310                 315                 320

Glu Arg Ile Asp Ala Ile Ala Ala Thr Arg Asn Phe Phe Glu Gln
            325                 330                 335

Leu Gly Val Pro Thr His Leu Ser Asp Tyr Gly Leu Asp Gly Ser Ser
                340                 345                 350

Ile Pro Ala Leu Leu Lys Lys Leu Glu Glu His Gly Met Thr Gln Leu
            355                 360                 365

Gly Glu Asn His Asp Ile Thr Leu Asp Val Ser Arg Arg Ile Tyr Glu
        370                 375                 380

Ala Ala Arg
385

<210> SEQ ID NO 57
<211> LENGTH: 395
<212> TYPE: PRT
<213> ORGANISM: Entamoeba histolytica

<400> SEQUENCE: 57

Met Thr Met Leu Asn Phe Thr Tyr Tyr Asn Pro Val Arg Leu Ile Tyr
1               5                   10                  15

Gly Lys Gly Ser Leu Asp Glu Ile Glu Lys Gln His Leu Ile Pro Glu
            20                  25                  30

Asp Ala Arg Ile Met Met Thr Tyr Gly Gly Ser Ile Lys Lys Asn
        35                  40                  45

Gly Val Tyr Glu Glu Val Leu Lys His Ile Lys Pro Ile Val Glu Phe
50                  55                  60

Gly Gly Ile Glu Pro Asn Pro Ser His Glu Thr Cys Ile Lys Ala Ile
65                  70                  75                  80

Lys Ile Ala Lys Glu Asn Lys Ile Asn Phe Leu Val Ala Val Gly Gly
                85                  90                  95

Gly Ser Ile Ile Asp Ala Thr Lys Tyr Ile Ala Leu Gly Met Glu His
            100                 105                 110

Thr Tyr Ser Asp Asp Pro Tyr Asp Ile Cys Leu Lys Gly Gly Lys Phe
        115                 120                 125

Lys Val Asn Pro Ala Gln Ala Lys Ile Gly Val Val Leu Thr Ile Pro
    130                 135                 140

Ala Thr Gly Ser Glu Thr Asn Cys Trp Gly Val Ile Ser Arg His Ala
145                 150                 155                 160

Asp Lys Leu Lys Leu Pro Phe Asn Asn Glu Ser Val Phe Pro Thr Trp
                165                 170                 175

Ser Ile Val Asp Pro Cys Phe Thr Met Ser Leu Pro Asp Asn Gln Ile
            180                 185                 190

Arg Asn Gly Leu Val Asp Ser Phe Val His Cys Ile Glu Gln Tyr Ile
        195                 200                 205

Gly Asn Tyr His Leu Asn Pro Val Val Glu Ala Glu Thr Glu Gly Val
    210                 215                 220

Met Arg Thr Ile Ile Gly Val Ser His Lys Thr Leu Glu Asn His Gln
225                 230                 235                 240

Asp Tyr Gln Ala Arg Ile Thr Phe Cys Tyr Ala Ala Thr Val Ala Leu
                245                 250                 255
```

```
Asn Met Ser Leu Leu Cys Gly Val Thr Leu Cys Gly Ala His Ala
            260                 265                 270

Val Gly Val Thr Leu Cys Gly Ala His Ala Val Gly His Glu Leu
            275                 280                 285

Thr Ser Tyr Tyr Gly Leu Ala His Gly Glu Thr Leu Ala Ile Thr Thr
            290                 295                 300

Pro Gly Val Met Arg Phe Asn Lys Glu Lys Asn Ala Lys Lys Leu Ile
305                 310                 315                 320

Gln Met Gly Glu Gln Val Phe Gly Ile Lys Asn Ser Thr Pro Glu Ala
                325                 330                 335

Ala Ile Glu Ala Thr Glu Lys Trp Phe Lys Ser Ile Gly Met Lys Thr
            340                 345                 350

Arg Leu Ser Glu Trp Gly Lys Gly Lys Glu Glu Phe Glu Thr Ile Ala
            355                 360                 365

Arg Lys Phe Glu Gly Asn Pro Ala Gly Ala His Lys Asp Ile Asp Tyr
            370                 375                 380

Lys Gly Cys Leu Gln Ile Leu Asn Asp Ile Tyr
385                 390                 395

<210> SEQ ID NO 58
<211> LENGTH: 349
<212> TYPE: PRT
<213> ORGANISM: Bacillus subtilis

<400> SEQUENCE: 58

Met Cys Asn Gln His Gln Thr Arg Val Leu Ser Val Ser His Ala Lys
1               5                   10                  15

Ala Lys Phe Glu Gln Thr Thr Ile Glu Arg Arg Gly Leu Arg Pro His
                20                  25                  30

Asp Val Leu Ile Asp Ile Lys Phe Ser Gly Ile Cys His Ser Asp Ile
            35                  40                  45

His Ser Ala Phe Asp Glu Trp Gly Gly Gly Ile Phe Pro Met Val Pro
        50                  55                  60

Gly His Glu Ile Ala Gly Val Val Thr Ala Val Gly Thr Lys Val Thr
65                  70                  75                  80

Lys Leu Ala Val Gly Asp Arg Val Gly Val Gly Cys Phe Val Asp Ser
                85                  90                  95

Cys Gly Glu Cys Glu Tyr Cys Leu Asn Ala Glu Glu Gln Phe Cys Thr
            100                 105                 110

Lys Gly Val Val Gln Thr Tyr Asn Ser Val Asp Tyr Asp Gly Asn Pro
        115                 120                 125

Thr Tyr Gly Gly Tyr Ser Gln Lys Ile Val Val Thr Asp Arg Phe Val
130                 135                 140

Val Arg Ile Pro Asp Arg Leu Glu Met Asp Val Ala Ser Pro Leu Leu
145                 150                 155                 160

Cys Ala Gly Ile Thr Thr Tyr Ser Pro Leu Lys His Trp Asn Val Gly
                165                 170                 175

Pro Gly Lys Lys Val Ala Ile Val Gly Val Gly Gly Leu Gly His Leu
            180                 185                 190

Ala Ile Gln Phe Ala His Ala Met Gly Ala Glu Val Thr Val Leu Ser
        195                 200                 205

Arg Ser Met Asn Lys Lys Glu Glu Ala Leu Glu Leu Gly Ala Asn His
210                 215                 220

Tyr Phe Ala Thr Ser Asp Pro Ala Thr Phe Thr Ala Leu Ala Gly Arg
225                 230                 235                 240
```

```
Phe Asp Val Ile Leu Asn Thr Val Ser Ala Asn Leu Asp Val Asp Ala
                245                 250                 255

Tyr Leu Ser Met Leu Arg Ile Asp Gly Thr Leu Val Ser Val Gly Ala
            260                 265                 270

Pro Ala Lys Pro Asp Thr Tyr Ser Val Phe Ser Leu Ile Met Gly Arg
        275                 280                 285

Arg Ser Ile Ala Gly Ser Leu Val Gly Ile Gln Glu Thr Gln Glu
    290                 295                 300

Met Leu Asp Phe Ala Ala Glu His Gly Ile Glu Pro Lys Ile Glu Val
305                 310                 315                 320

Ile Gly Ala Asp Gln Val Asp Glu Ala Tyr Glu Arg Ile Leu Arg Ser
                325                 330                 335

Asp Val Arg Tyr Arg Phe Val Ile Asp Ile Ser Thr Leu
            340                 345
```

<210> SEQ ID NO 59
<211> LENGTH: 378
<212> TYPE: PRT
<213> ORGANISM: Bacillus subtilis

<400> SEQUENCE: 59

```
Met Lys Ala Val Thr Tyr Gln Gly Ile Lys Asn Val Val Lys Asp
1               5                   10                  15

Val Pro Asp Pro Lys Ile Glu Lys Ser Asp Asp Met Ile Ile Lys Val
            20                  25                  30

Thr Ser Thr Ala Ile Cys Gly Ser Asp Leu His Leu Ile His Gly Phe
        35                  40                  45

Ile Pro Asn Met Gln Glu Asp Tyr Val Ile Gly His Glu Pro Met Gly
50                  55                  60

Ile Val Glu Glu Val Gly Ser Gly Val Thr Lys Leu Lys Lys Gly Asp
65                  70                  75                  80

Arg Val Ile Ile Pro Phe Asn Ile Ala Cys Gly Glu Cys Phe Phe Cys
                85                  90                  95

Lys Asn Gln Leu Glu Ser Gln Cys Asp Gln Ser Asn Asp Asn Gly Glu
            100                 105                 110

Met Gly Ala Tyr Phe Gly Tyr Ser Gly Gln Thr Gly Gly Tyr Pro Gly
        115                 120                 125

Gly Gln Ala Glu Tyr Leu Arg Val Pro Phe Ala Asn Phe Thr His Phe
130                 135                 140

Lys Ile Pro Glu Ser Cys Glu Glu Pro Asp Glu Lys Leu Ser Val Ile
145                 150                 155                 160

Ala Asp Ala Met Thr Thr Gly Phe Trp Ser Val Asp Asn Ala Gly Val
                165                 170                 175

Lys Lys Gly Asp Thr Val Ile Val Leu Gly Cys Gly Pro Val Gly Leu
            180                 185                 190

Phe Ala Gln Lys Phe Cys Trp Leu Lys Gly Ala Lys Arg Val Ile Ala
        195                 200                 205

Val Asp Tyr Val Asn Tyr Arg Leu Gln His Ala Lys Arg Thr Asn Lys
210                 215                 220

Val Glu Ile Val Asn Phe Glu Asp His Glu Asn Thr Gly Asn Tyr Leu
225                 230                 235                 240

Lys Glu Ile Thr Lys Gly Gly Ala Asp Val Val Ile Asp Ala Val Gly
                245                 250                 255

Met Asp Gly Lys Met Ser Asp Leu Glu Phe Leu Ala Ser Gly Leu Lys
```

```
                   260                 265                 270
Leu His Gly Gly Thr Met Ser Ala Leu Val Ile Ala Ser Gln Ala Val
                275                 280                 285

Arg Lys Gly Gly Thr Ile Gln Ile Thr Gly Val Tyr Gly Gly Arg Tyr
            290                 295                 300

Asn Gly Phe Pro Leu Gly Asp Ile Met Gln Arg Asn Val Asn Ile Arg
305                 310                 315                 320

Ser Gly Gln Ala Pro Val Ile His Tyr Met Pro Tyr Met Phe Glu Leu
                325                 330                 335

Val Ser Thr Gly Lys Ile Asp Pro Gly Asp Val Val Ser His Val Leu
            340                 345                 350

Pro Leu Ser Glu Ala Lys His Gly Tyr Asp Ile Phe Asp Ser Lys Met
                355                 360                 365

Asp Asp Cys Ile Lys Val Val Leu Lys Pro
370                 375

<210> SEQ ID NO 60
<211> LENGTH: 390
<212> TYPE: PRT
<213> ORGANISM: Clostridium acetobutylicum

<400> SEQUENCE: 60

Met Val Asp Phe Glu Tyr Ser Ile Pro Thr Arg Ile Phe Phe Gly Lys
1               5                   10                  15

Asp Lys Ile Asn Val Leu Gly Arg Glu Leu Lys Lys Tyr Gly Ser Lys
                20                  25                  30

Val Leu Ile Val Tyr Gly Gly Gly Ser Ile Lys Arg Asn Gly Ile Tyr
            35                  40                  45

Asp Lys Ala Val Ser Ile Leu Glu Lys Asn Ser Ile Lys Phe Tyr Glu
        50                  55                  60

Leu Ala Gly Val Glu Pro Asn Pro Arg Val Thr Thr Val Glu Lys Gly
65                  70                  75                  80

Val Lys Ile Cys Arg Glu Asn Gly Val Glu Val Val Leu Ala Ile Gly
                85                  90                  95

Gly Gly Ser Ala Ile Asp Cys Ala Lys Val Ile Ala Ala Ala Cys Glu
            100                 105                 110

Tyr Asp Gly Asn Pro Trp Asp Ile Val Leu Asp Gly Ser Lys Ile Lys
        115                 120                 125

Arg Val Leu Pro Ile Ala Ser Ile Leu Thr Ile Ala Ala Thr Gly Ser
130                 135                 140

Glu Met Asp Thr Trp Ala Val Ile Asn Asn Met Asp Thr Asn Glu Lys
145                 150                 155                 160

Leu Ile Ala Ala His Pro Asp Met Ala Pro Lys Phe Ser Ile Leu Asp
                165                 170                 175

Pro Thr Tyr Thr Tyr Thr Val Pro Thr Asn Gln Thr Ala Ala Gly Thr
            180                 185                 190

Ala Asp Ile Met Ser His Ile Phe Glu Val Tyr Phe Ser Asn Thr Lys
        195                 200                 205

Thr Ala Tyr Leu Gln Asp Arg Met Ala Glu Ala Leu Leu Arg Thr Cys
    210                 215                 220

Ile Lys Tyr Gly Gly Ile Ala Leu Glu Lys Pro Asp Asp Tyr Glu Ala
225                 230                 235                 240

Arg Ala Asn Leu Met Trp Ala Ser Ser Leu Ala Ile Asn Gly Leu Leu
                245                 250                 255
```

```
Thr Tyr Gly Lys Asp Thr Asn Trp Ser Val His Leu Met Glu His Glu
            260                 265                 270

Leu Ser Ala Tyr Tyr Asp Ile Thr His Gly Val Gly Leu Ala Ile Leu
            275                 280                 285

Thr Pro Asn Trp Met Glu Tyr Ile Leu Asn Asn Asp Thr Val Tyr Lys
290                 295                 300

Phe Val Glu Tyr Gly Val Asn Val Trp Gly Ile Asp Lys Glu Lys Asn
305                 310                 315                 320

His Tyr Asp Ile Ala His Gln Ala Ile Gln Lys Thr Arg Asp Tyr Phe
                325                 330                 335

Val Asn Val Leu Gly Leu Pro Ser Arg Leu Arg Asp Val Gly Ile Glu
            340                 345                 350

Glu Glu Lys Leu Asp Ile Met Ala Lys Glu Ser Val Lys Leu Thr Gly
            355                 360                 365

Gly Thr Ile Gly Asn Leu Arg Pro Val Asn Ala Ser Glu Val Leu Gln
370                 375                 380

Ile Phe Lys Lys Ser Val
385                 390

<210> SEQ ID NO 61
<211> LENGTH: 389
<212> TYPE: PRT
<213> ORGANISM: Clostridium acetobutylicum

<400> SEQUENCE: 61

Met Leu Ser Phe Asp Tyr Ser Ile Pro Thr Lys Val Phe Phe Gly Lys
1               5                   10                  15

Gly Lys Ile Asp Val Ile Gly Glu Glu Ile Lys Lys Tyr Gly Ser Arg
            20                  25                  30

Val Leu Ile Val Tyr Gly Gly Ser Ile Lys Arg Asn Gly Ile Tyr
            35                  40                  45

Asp Arg Ala Thr Ala Ile Leu Lys Glu Asn Asn Ile Ala Phe Tyr Glu
        50                  55                  60

Leu Ser Gly Val Glu Pro Asn Pro Arg Ile Thr Thr Val Lys Lys Gly
65                  70                  75                  80

Ile Glu Ile Cys Arg Glu Asn Asn Val Asp Leu Val Leu Ala Ile Gly
                85                  90                  95

Gly Gly Ser Ala Ile Asp Cys Ser Lys Val Ile Ala Ala Gly Val Tyr
            100                 105                 110

Tyr Asp Gly Asp Thr Trp Asp Met Val Lys Asp Pro Ser Lys Ile Thr
        115                 120                 125

Lys Val Leu Pro Ile Ala Ser Ile Leu Thr Leu Ser Ala Thr Gly Ser
130                 135                 140

Glu Met Asp Gln Ile Ala Val Ile Ser Asn Met Glu Thr Asn Glu Lys
145                 150                 155                 160

Leu Gly Val Gly His Asp Asp Met Arg Pro Lys Phe Ser Val Leu Asp
                165                 170                 175

Pro Thr Tyr Thr Phe Thr Val Pro Lys Asn Gln Thr Ala Ala Gly Thr
            180                 185                 190

Ala Asp Ile Met Ser His Thr Phe Glu Ser Tyr Phe Ser Gly Val Glu
        195                 200                 205

Gly Ala Tyr Val Gln Asp Gly Ile Ala Glu Ala Ile Leu Arg Thr Cys
    210                 215                 220

Ile Lys Tyr Gly Lys Ile Ala Met Glu Lys Thr Asp Asp Tyr Glu Ala
225                 230                 235                 240
```

Arg Ala Asn Leu Met Trp Ala Ser Ser Leu Ala Ile Asn Gly Leu Leu
            245                 250                 255

Ser Leu Gly Lys Asp Arg Lys Trp Ser Cys His Pro Met Glu His Glu
        260                 265                 270

Leu Ser Ala Tyr Tyr Asp Ile Thr His Gly Val Gly Leu Ala Ile Leu
    275                 280                 285

Thr Pro Asn Trp Met Glu Tyr Ile Leu Asn Asp Thr Leu His Lys
290                 295                 300

Phe Val Ser Tyr Gly Ile Asn Val Trp Gly Ile Asp Lys Asn Lys Asp
305                 310                 315                 320

Asn Tyr Glu Ile Ala Arg Glu Ala Ile Lys Asn Thr Arg Glu Tyr Phe
                325                 330                 335

Asn Ser Leu Gly Ile Pro Ser Lys Leu Arg Glu Val Gly Ile Gly Lys
            340                 345                 350

Asp Lys Leu Glu Leu Met Ala Lys Gln Ala Val Arg Asn Ser Gly Gly
        355                 360                 365

Thr Ile Gly Ser Leu Arg Pro Ile Asn Ala Glu Asp Val Leu Glu Ile
    370                 375                 380

Phe Lys Lys Ser Tyr
385

<210> SEQ ID NO 62
<211> LENGTH: 357
<212> TYPE: PRT
<213> ORGANISM: Rhodococcus opacus

<400> SEQUENCE: 62

Met Ala Glu Arg Ser Ser Glu Phe Val Phe Thr Gly Asn Pro Ala Arg
1               5                   10                  15

Val Ile Phe Gly Ala Gly Arg Met Arg Asn Val Arg Glu Glu Val Glu
            20                  25                  30

Arg Leu Gly Arg Gly Arg Val Leu Leu Leu Gly Ser Glu Asn Leu Arg
        35                  40                  45

Glu Val Cys Asp Gln Val Gln Asp Leu Leu Gly Glu Leu Phe Val Asn
    50                  55                  60

Arg Tyr Asp Gly Ala Ala Met His Thr Pro Val Glu Val Thr Asp Ile
65                  70                  75                  80

Ala Leu Ala Gln Leu Arg Thr Ser Glu Ala Asp Cys Val Val Ala Ile
                85                  90                  95

Gly Gly Gly Ser Thr Thr Gly Leu Ala Lys Ala Leu Ala Ala Arg Thr
            100                 105                 110

Gly Val Asp Gln Val Ile Leu Pro Thr Thr Tyr Ala Gly Ser Glu Val
        115                 120                 125

Thr Pro Val Leu Gly Glu Thr Val Glu Gly Arg Lys Thr Thr Arg Ser
    130                 135                 140

Thr Leu Ala Val Leu Pro Glu Thr Val Ile Tyr Asp Val Glu Leu Ser
145                 150                 155                 160

Lys Asn Leu Pro Val Pro Ile Ala Val Ala Ser Ala Val Asn Ala Leu
                165                 170                 175

Ala His Ala Val Glu Ala Met Tyr Ser Pro Asp Ala Asn Pro Val Val
            180                 185                 190

Asp Thr Trp Ala Leu Glu Ala Ala Gln Ala Leu Ala Arg Gly Leu Arg
        195                 200                 205

Gly Leu Val Ser Asp Pro Ser Cys Arg Arg Ile Arg Thr Asp Leu Leu

```
                        210                 215                 220
Arg Gly Ser Trp Leu Ala Gly Met Cys Leu Gly Ser Val Gly Met Ala
225                 230                 235                 240

Val His His Lys Leu Cys His Thr Leu Gly Gly Ala Phe Gly Leu Pro
                245                 250                 255

His Ala Pro Thr His Thr Val Val Leu Pro Tyr Ala Met Ser Phe Asn
            260                 265                 270

Ala Ser Glu Val Pro Asp Val Met Asp Ser Leu Ala Ser Ala Met Asn
        275                 280                 285

Val Ser Asn Ala Pro Ala Gly Val Trp Asp Leu Ile Ala Asp Ala Gly
    290                 295                 300

Gly Pro Thr Ser Leu Ala Ser Leu Gly Leu Leu Gln Thr Asp Leu Asp
305                 310                 315                 320

Arg Ala Ala Asp Leu Ala Thr Glu Ala Pro Tyr Arg Asn Pro Arg Gln
                325                 330                 335

Ile Thr Arg Ser Gly Ile Arg Asp Leu Leu Gln Ser Ala Trp Glu Gly
            340                 345                 350

Asn Arg Pro Pro Glu
        355

<210> SEQ ID NO 63
<211> LENGTH: 359
<212> TYPE: PRT
<213> ORGANISM: Cupriavidus pinatubonensis

<400> SEQUENCE: 63

Met Thr Gly Asp Leu Asn Glu Phe Val Ala His Phe Trp Pro Val Arg
1               5                   10                  15

Val Val Phe Gly Ala Gly Ser Thr Glu Arg Ile Pro Ala Glu Val Lys
                20                  25                  30

Arg Leu Gly Ala Arg Arg Ala Leu Val Leu Cys Thr Pro Asp Gln Arg
            35                  40                  45

Asp Leu Ala Gln Arg Val Leu Gly Asp Leu Gly Asp Leu Gly Ala Gly
        50                  55                  60

Phe His Asp Gly Ala Val Met His Val Pro Glu Ala Ser Val Thr Arg
65                  70                  75                  80

Ala Ala Gln Ala Ala Arg Asp Ala Asp Ala Asp Leu Leu Val Ala Val
                85                  90                  95

Gly Gly Gly Ser Thr Ile Gly Leu Ala Lys Ala Leu Ala Leu His His
            100                 105                 110

Gly Met Arg Phe Val Ala Leu Pro Thr Thr Tyr Ala Gly Ser Glu Met
        115                 120                 125

Thr Pro Ile Trp Gly Leu Thr Ala Asp Gly Ala Lys Arg Thr Gly Arg
    130                 135                 140

Asp Pro Arg Val Leu Pro Ser Thr Val Leu Tyr Asp Pro His His Leu
145                 150                 155                 160

Thr Ser Leu Pro Pro Glu Val Thr Gly Pro Ser Gly Met Asn Ala Ile
                165                 170                 175

Ala His Ala Val Glu Ser Met Tyr Ala Pro Asp Arg Asn Pro Ile Thr
            180                 185                 190

Met Leu Leu Ala Glu Glu Ser Ile Arg Ala Met Ala Gln Gly Leu Pro
        195                 200                 205

Val Ala Val Asp Ser Pro Gly Asp Leu Asp Ala Arg Thr Arg Thr Leu
    210                 215                 220
```

Tyr Ala Ala Trp Leu Ala Gly Thr Val Leu Gly Met Val Ser Met Gly
225                 230                 235                 240

Leu His His Lys Leu Cys His Val Leu Gly Gly Arg Phe Asn Leu Pro
            245                 250                 255

His Ala Pro Met His Ala Val Leu Leu Pro His Val Ala Ala Phe Asn
        260                 265                 270

Glu Val Ala Ala Pro Ala Glu Leu Gly Arg Val Ala Ala Ala Leu Gly
    275                 280                 285

Ala Pro Gly Pro Gly Gly Ala Gly Ala Ala Leu His Ala Leu Leu Arg
    290                 295                 300

Phe Thr Cys Thr Glu Arg Ser Leu Ala Ala Ile Gly Met Pro Ala Gln
305                 310                 315                 320

Gly Ile Tyr Asp Ala Ala Glu His Ala Leu Ala Asp Ala Tyr Ala Asn
                325                 330                 335

Pro Arg Gln Ala Ser Arg Glu Asp Ile Ala Arg Leu Leu Arg Ala Ala
            340                 345                 350

Phe Thr Gly Glu Met Pro Ala
            355

<210> SEQ ID NO 64
<211> LENGTH: 354
<212> TYPE: PRT
<213> ORGANISM: Cupriavidus pinatubonensis

<400> SEQUENCE: 64

Met Lys Lys Phe Thr Leu Asp Tyr Leu Ser Pro Arg Val Val Phe Gly
1               5                   10                  15

Ala Gly Thr Ala Ser Ala Leu Pro Asp Glu Ile Gly Arg Leu Gly Ala
            20                  25                  30

Arg Arg Pro Leu Val Leu Ser Ser Pro Glu Gln Arg Glu Leu Ala Lys
        35                  40                  45

Asp Ile Val Arg Pro Ile Gly Asp Arg Val Ala Gly Tyr Phe Asp Gly
    50                  55                  60

Ala Thr Met His Val Pro Val Asp Val Ile Gln Lys Ala Glu Arg Ala
65                  70                  75                  80

Phe Asn Asp Thr Asp Ala Asp Ser Ile Ile Ala Ile Gly Gly Gly Ser
                85                  90                  95

Thr Thr Gly Leu Ala Lys Ile Leu Ser Met Asn Leu Asp Val Pro Ser
            100                 105                 110

Leu Val Ile Pro Thr Thr Tyr Ala Gly Ser Glu Met Thr Thr Ile Trp
        115                 120                 125

Gly Val Thr Glu Gly Gly Met Lys Arg Thr Gly Arg Asp Pro Lys Val
    130                 135                 140

Leu Pro Lys Thr Val Ile Tyr Asp Pro Leu Leu Thr Val Asp Leu Pro
145                 150                 155                 160

Leu Ala Ile Ser Val Thr Ser Ala Leu Asn Ala Ile Ala His Ala Ala
                165                 170                 175

Glu Gly Leu Tyr Ser Ala Asp Leu Asn Pro Val Leu Glu Thr Met Cys
            180                 185                 190

Lys Gln Gly Ile Cys Ala Leu Phe Asp Ala Ile Pro Arg Leu Val Ala
        195                 200                 205

Lys Pro Thr Asp Ala Glu Ala Arg Thr Asp Ala Leu Phe Gly Ala Trp
    210                 215                 220

Met Cys Gly Thr Ala Leu Cys His Leu Gly Met Gly Leu His His Lys
225                 230                 235                 240

```
Leu Cys His Thr Leu Gly Gly Thr Leu Asn Leu Pro His Ala Glu Thr
                245                 250                 255

His Ala Ile Val Leu Pro His Ala Leu Ala Tyr Asn Leu Pro Tyr Ala
            260                 265                 270

Ala Pro Ala Glu Arg Leu Leu Gln Glu Val Ala Gly Ser Ser Asp Val
        275                 280                 285

Pro Ser Ala Leu Tyr Asp Leu Ala Arg Asn Ala Gly Ala Pro Leu Ser
    290                 295                 300

Leu Ala Glu Ile Gly Met Arg Pro Glu Asp Ile Pro Arg Val Arg Asp
305                 310                 315                 320

Leu Ala Leu Arg Asp Gln Tyr Pro Asn Pro Arg Pro Leu Glu Ser Asp
                325                 330                 335

Ala Leu Glu Thr Leu Leu Val Asn Ala Phe Arg Gly Arg Pro Asp
            340                 345                 350

Phe Lys
```

<210> SEQ ID NO 65
<211> LENGTH: 352
<212> TYPE: PRT
<213> ORGANISM: Pseudomonas sp. B13

<400> SEQUENCE: 65

```
Met Asn Phe Ile His Asp Tyr Arg Ser Pro Arg Val Ile Phe Gly Pro
1               5                   10                  15

Asp Ser Leu Ala Arg Leu Pro Gln Glu Leu Glu Arg Leu Gly Ile Asp
            20                  25                  30

Arg Ala Leu Val Leu Thr Thr Pro Glu Gln Ala Pro Leu Gly Arg Gln
        35                  40                  45

Val Ala Glu Pro Val Ile Gly His Val Ala Ala Phe Tyr Asp Gly Ala
    50                  55                  60

Thr Met His Val Pro Ala Leu Val Ala Glu Glu Ala Cys Lys Ile Ala
65                  70                  75                  80

Arg Thr Ser Glu Ala Asn Gly Val Ile Ala Ile Gly Gly Gly Ser Thr
                85                  90                  95

Ile Gly Leu Ala Lys Ile Val Ala Leu Arg Thr Glu Leu Pro Ile Val
            100                 105                 110

Ala Val Pro Thr Thr Tyr Ala Gly Ser Glu Met Thr Ser Ile Phe Gly
        115                 120                 125

Ile Thr Glu Gly Gly Val Lys Lys Thr Gly Arg Asp Ala Arg Val Met
130                 135                 140

Pro Arg Ala Val Ile Tyr Glu Pro Arg Leu Thr Leu Glu Leu Pro Leu
145                 150                 155                 160

Ser Ile Ser Val Thr Ser Ala Ile Asn Ala Ile Ala His Ala Val Glu
                165                 170                 175

Gly Leu Tyr Ala Pro Asp Ala Thr Pro Leu Leu Thr Ile Met Ala Gln
            180                 185                 190

Glu Gly Ile Ala Ala Thr Val Arg Ala Ile Ser Arg Met Tyr Gln Ser
        195                 200                 205

Pro Arg Asp Leu Gln Ala Arg Gly Asp Ala Leu Tyr Gly Ala Trp Leu
    210                 215                 220

Cys Ala Ser Val Leu Gly Asn Val Ser Met Ala Leu His His Lys Leu
225                 230                 235                 240

Cys His Thr Leu Gly Gly Thr Leu Asp Leu Pro His Ala Gln Thr His
                245                 250                 255
```

```
Thr Val Val Leu Pro His Ala Leu Ala Tyr Asn Ala Arg Ala Val Pro
            260                 265                 270

Asp Ala Met Arg Val Leu Arg Ile Ala Leu Gly His Asp Asp Pro Pro
            275                 280                 285

Thr Ala Leu Tyr Glu Leu Ala Arg Asp Asn Gly Ala Pro Val Ala Leu
            290                 295                 300

Arg Asp Leu Gly Met Arg Glu Asp Ile Glu His Val Gly Asp Leu
305                 310                 315                 320

Ala Leu Gln Asp Arg Tyr Pro Asn Pro Arg Glu Leu Asp Arg Asp Ala
            325                 330                 335

Leu Leu Ala Leu Leu Arg Asp Ala Tyr His Gly Arg Pro Pro Ser Ala
            340                 345                 350

<210> SEQ ID NO 66
<211> LENGTH: 388
<212> TYPE: PRT
<213> ORGANISM: Clostridium saccharobutylicum

<400> SEQUENCE: 66

Met Met Arg Phe Thr Leu Pro Arg Asp Ile Tyr Tyr Gly Lys Gly Ser
1               5                   10                  15

Leu Glu Gln Leu Lys Asn Leu Lys Gly Lys Ala Met Leu Val Leu
            20                  25                  30

Gly Gly Gly Ser Met Lys Arg Phe Gly Phe Val Asp Lys Val Leu Gly
            35                  40                  45

Tyr Leu Lys Glu Ala Gly Ile Glu Val Lys Leu Ile Glu Gly Val Glu
50                  55                  60

Pro Asp Pro Ser Val Glu Thr Val Phe Lys Gly Ala Glu Leu Met Arg
65                  70                  75                  80

Gln Phe Glu Pro Asp Trp Ile Ile Ala Met Gly Gly Gly Ser Pro Ile
            85                  90                  95

Asp Ala Ala Lys Ala Met Trp Ile Phe Tyr Glu His Pro Glu Lys Thr
            100                 105                 110

Phe Asp Asp Ile Lys Asp Pro Phe Thr Val Pro Glu Leu Arg Asn Lys
            115                 120                 125

Ala Lys Phe Leu Ala Ile Pro Ser Thr Ser Gly Thr Ala Thr Glu Val
            130                 135                 140

Thr Ala Phe Ser Val Ile Thr Asp Tyr Lys Thr Glu Ile Lys Tyr Pro
145                 150                 155                 160

Leu Ala Asp Phe Asn Ile Thr Pro Asp Val Ala Val Val Asp Ser Glu
            165                 170                 175

Leu Ala Glu Thr Met Pro Pro Lys Leu Thr Ala His Thr Gly Met Asp
            180                 185                 190

Ala Leu Thr His Ala Ile Glu Ala Tyr Val Ala Thr Leu His Ser Pro
            195                 200                 205

Phe Thr Asp Pro Leu Ala Met Gln Ala Ile Glu Met Ile Asn Glu His
            210                 215                 220

Leu Phe Lys Ser Tyr Glu Gly Asp Lys Glu Ala Arg Glu Gln Met His
225                 230                 235                 240

Tyr Ala Gln Cys Leu Ala Gly Met Ala Phe Ser Asn Ala Leu Leu Gly
            245                 250                 255

Ile Cys His Ser Met Ala His Lys Thr Gly Ala Val Phe His Ile Pro
            260                 265                 270

His Gly Cys Ala Asn Ala Ile Tyr Leu Pro Tyr Val Ile Lys Phe Asn
```

```
                        275                 280                 285
Ser Lys Thr Ser Leu Glu Arg Tyr Ala Lys Ile Ala Lys Gln Ile Ser
    290                 295                 300

Leu Ala Gly Asn Thr Asn Glu Glu Leu Val Asp Ser Leu Ile Asn Leu
305                 310                 315                 320

Val Lys Glu Leu Asn Lys Lys Met Gln Ile Pro Thr Thr Leu Lys Glu
                325                 330                 335

Tyr Gly Ile His Glu Gln Glu Phe Lys Asn Lys Val Asp Leu Ile Ser
            340                 345                 350

Glu Arg Ala Ile Gly Asp Ala Cys Thr Gly Ser Asn Pro Arg Gln Leu
        355                 360                 365

Asn Lys Asp Glu Met Lys Lys Ile Phe Glu Cys Val Tyr Tyr Gly Thr
    370                 375                 380

Glu Val Asp Phe
385

<210> SEQ ID NO 67
<211> LENGTH: 870
<212> TYPE: PRT
<213> ORGANISM: Entamoeba histolytica

<400> SEQUENCE: 67

Met Ser Thr Gln Gln Thr Met Thr Val Asp Glu His Ile Asn Gln Leu
1               5                   10                  15

Val Arg Lys Ala Gln Val Ala Leu Lys Glu Tyr Leu Lys Pro Glu Tyr
            20                  25                  30

Thr Gln Glu Lys Ile Asp Tyr Ile Val Lys Lys Ala Ser Val Ala Ala
        35                  40                  45

Leu Asp Gln His Cys Ala Leu Ala Ala Ala Val Glu Glu Thr Gly
    50                  55                  60

Arg Gly Ile Phe Glu Asp Lys Ala Thr Lys Asn Ile Phe Ala Cys Glu
65                  70                  75                  80

His Val Thr His Glu Met Arg His Ala Lys Thr Val Gly Ile Ile Asn
                85                  90                  95

Val Asp Pro Leu Tyr Gly Ile Thr Glu Ile Ala Glu Pro Val Gly Val
            100                 105                 110

Val Cys Gly Val Thr Pro Val Thr Asn Pro Thr Ser Thr Ala Ile Phe
        115                 120                 125

Lys Ser Leu Ile Ser Ile Lys Thr Arg Asn Pro Ile Val Phe Ser Phe
    130                 135                 140

His Pro Ser Ala Leu Lys Cys Ser Ile Met Ala Ala Lys Ile Val Arg
145                 150                 155                 160

Asp Ala Ala Ile Ala Ala Gly Ala Pro Glu Asn Cys Ile Gln Trp Ile
                165                 170                 175

Glu Phe Gly Gly Ile Glu Ala Ser Asn Lys Leu Met Asn His Pro Gly
            180                 185                 190

Val Ala Thr Ile Leu Ala Thr Gly Gly Asn Ala Met Val Lys Ala Ala
        195                 200                 205

Tyr Ser Ser Gly Lys Pro Ala Leu Gly Val Gly Ala Gly Asn Val Pro
    210                 215                 220

Thr Tyr Ile Glu Lys Thr Cys Asn Ile Lys Gln Ala Ala Asn Asp Val
225                 230                 235                 240

Val Met Ser Lys Ser Phe Asp Asn Gly Met Ile Cys Ala Ser Glu Gln
                245                 250                 255
```

```
Ala Ala Ile Ile Asp Lys Glu Ile Tyr Asp Gln Val Val Glu Met
            260                 265                 270
Lys Thr Leu Gly Ala Tyr Phe Ile Asn Glu Glu Lys Ala Lys Leu
        275                 280                 285
Glu Lys Phe Met Phe Gly Val Asn Ala Tyr Ser Ala Asp Val Asn Asn
290                 295                 300
Ala Arg Leu Asn Pro Lys Cys Pro Gly Met Ser Pro Gln Trp Phe Ala
305                 310                 315                 320
Glu Gln Val Gly Ile Lys Val Pro Glu Asp Cys Asn Ile Ile Cys Ala
                325                 330                 335
Val Cys Lys Glu Val Gly Pro Asn Glu Pro Leu Thr Arg Glu Lys Leu
            340                 345                 350
Ser Pro Val Leu Ala Ile Leu Lys Ala Glu Asn Thr Gln Asp Gly Ile
        355                 360                 365
Asp Lys Ala Glu Ala Met Val Glu Phe Asn Gly Arg Gly His Ser Ala
370                 375                 380
Ala Ile His Ser Asn Asp Lys Ala Val Val Glu Lys Tyr Ala Leu Thr
385                 390                 395                 400
Met Lys Ala Cys Arg Ile Leu His Asn Thr Pro Ser Ser Gln Gly Gly
                405                 410                 415
Ile Gly Ser Ile Tyr Asn Tyr Ile Trp Pro Ser Phe Thr Leu Gly Cys
            420                 425                 430
Gly Ser Tyr Gly Gly Asn Ser Val Ser Ala Asn Val Thr Tyr His Asn
        435                 440                 445
Leu Leu Asn Ile Lys Arg Leu Ala Asp Arg Arg Asn Asn Leu Gln Trp
450                 455                 460
Phe Arg Val Pro Pro Lys Ile Phe Phe Glu Pro His Ser Ile Arg Tyr
465                 470                 475                 480
Leu Ala Glu Leu Lys Glu Leu Ser Lys Ile Phe Ile Val Ser Asp Arg
                485                 490                 495
Met Met Tyr Lys Leu Gly Tyr Val Asp Arg Val Met Asp Val Leu Lys
            500                 505                 510
Arg Arg Ser Asn Glu Val Glu Ile Glu Ile Phe Ile Asp Val Glu Pro
        515                 520                 525
Asp Pro Ser Ile Gln Thr Val Gln Lys Gly Leu Ala Val Met Asn Thr
530                 535                 540
Phe Gly Pro Asp Asn Ile Ile Ala Ile Gly Gly Gly Ser Ala Met Asp
545                 550                 555                 560
Ala Ala Lys Ile Met Trp Leu Leu Tyr Glu His Pro Glu Ala Asp Phe
                565                 570                 575
Phe Ala Met Lys Gln Lys Phe Ile Asp Leu Arg Lys Arg Ala Phe Lys
            580                 585                 590
Phe Pro Thr Met Gly Lys Lys Ala Arg Leu Ile Cys Ile Pro Thr Thr
        595                 600                 605
Ser Gly Thr Gly Ser Glu Val Thr Pro Phe Ala Val Ile Ser Asp His
610                 615                 620
Glu Thr Gly Lys Lys Tyr Pro Leu Ala Asp Tyr Ser Leu Thr Pro Ser
625                 630                 635                 640
Val Ala Ile Val Asp Pro Met Phe Thr Met Ser Leu Pro Lys Arg Ala
                645                 650                 655
Ile Ala Asp Thr Gly Leu Asp Val Leu Val His Ala Thr Glu Ala Tyr
            660                 665                 670
Val Ser Val Met Ala Asn Glu Tyr Thr Asp Gly Leu Ala Arg Glu Ala
```

```
                675                 680                 685
Val Lys Leu Val Phe Glu Asn Leu Leu Lys Ser Tyr Asn Gly Asp Leu
        690                 695                 700

Glu Ala Arg Glu Lys Met His Asn Ala Ala Thr Ile Ala Gly Met Ala
705                 710                 715                 720

Phe Ala Ser Ala Phe Leu Gly Met Asp His Ser Met Ala His Lys Val
                725                 730                 735

Gly Ala Ala Phe His Leu Pro His Gly Arg Cys Val Ala Val Leu Leu
                740                 745                 750

Pro His Val Ile Arg Tyr Asn Gly Gln Lys Pro Arg Lys Leu Ala Met
        755                 760                 765

Trp Pro Lys Tyr Asn Phe Tyr Lys Ala Asp Gln Arg Tyr Met Glu Leu
770                 775                 780

Ala Gln Met Val Gly Leu Lys Cys Asn Thr Pro Ala Glu Gly Val Glu
785                 790                 795                 800

Ala Phe Ala Lys Ala Cys Glu Glu Leu Met Lys Ala Thr Glu Thr Ile
                805                 810                 815

Thr Gly Phe Lys Lys Ala Asn Ile Asp Glu Ala Ala Trp Met Ser Lys
                820                 825                 830

Val Pro Glu Met Ala Leu Leu Ala Phe Glu Asp Gln Cys Ser Pro Ala
        835                 840                 845

Asn Pro Arg Val Pro Met Val Lys Asp Met Glu Lys Ile Leu Lys Ala
850                 855                 860

Ala Tyr Tyr Pro Ile Ala
865                 870

<210> SEQ ID NO 68
<211> LENGTH: 891
<212> TYPE: PRT
<213> ORGANISM: Escherichia coli

<400> SEQUENCE: 68

Met Ala Val Thr Asn Val Ala Glu Leu Asn Ala Leu Val Glu Arg Val
1               5                   10                  15

Lys Lys Ala Gln Arg Glu Tyr Ala Ser Phe Thr Gln Glu Gln Val Asp
                20                  25                  30

Lys Ile Phe Arg Ala Ala Ala Leu Ala Ala Ala Asp Ala Arg Ile Pro
            35                  40                  45

Leu Ala Lys Met Ala Val Ala Glu Ser Gly Met Gly Ile Val Glu Asp
        50                  55                  60

Lys Val Ile Lys Asn His Phe Ala Ser Glu Tyr Ile Tyr Asn Ala Tyr
65                  70                  75                  80

Lys Asp Glu Lys Thr Cys Gly Val Leu Ser Glu Asp Asp Thr Phe Gly
                85                  90                  95

Thr Ile Thr Ile Ala Glu Pro Ile Gly Ile Ile Cys Gly Ile Val Pro
            100                 105                 110

Thr Thr Asn Pro Thr Ser Thr Ala Ile Phe Lys Ser Leu Ile Ser Leu
        115                 120                 125

Lys Thr Arg Asn Ala Ile Ile Phe Ser Pro His Pro Arg Ala Lys Asp
    130                 135                 140

Ala Thr Asn Lys Ala Ala Asp Ile Val Leu Gln Ala Ala Ile Ala Ala
145                 150                 155                 160

Gly Ala Pro Lys Asp Leu Ile Gly Trp Ile Asp Gln Pro Ser Val Glu
                165                 170                 175
```

-continued

```
Leu Ser Asn Ala Leu Met His His Pro Asp Ile Asn Leu Ile Leu Ala
                180                 185                 190

Thr Gly Gly Pro Gly Met Val Lys Ala Ala Tyr Ser Ser Gly Lys Pro
            195                 200                 205

Ala Ile Gly Val Gly Ala Gly Asn Thr Pro Val Val Ile Asp Glu Thr
        210                 215                 220

Ala Asp Ile Lys Arg Ala Val Ala Ser Val Leu Met Ser Lys Thr Phe
225                 230                 235                 240

Asp Asn Gly Val Ile Cys Ala Ser Glu Gln Ser Val Val Val Val Asp
                245                 250                 255

Ser Val Tyr Asp Ala Val Arg Glu Arg Phe Ala Thr His Gly Gly Tyr
            260                 265                 270

Leu Leu Gln Gly Lys Glu Leu Lys Ala Val Gln Asp Val Ile Leu Lys
        275                 280                 285

Asn Gly Ala Leu Asn Ala Ala Ile Val Gly Gln Pro Ala Tyr Lys Ile
290                 295                 300

Ala Glu Leu Ala Gly Phe Ser Val Pro Glu Asn Thr Lys Ile Leu Ile
305                 310                 315                 320

Gly Glu Val Thr Val Val Asp Glu Ser Glu Pro Phe Ala His Glu Lys
                325                 330                 335

Leu Ser Pro Thr Leu Ala Met Tyr Arg Ala Lys Asp Phe Glu Asp Ala
            340                 345                 350

Val Glu Lys Ala Glu Lys Leu Val Ala Met Gly Gly Ile Gly His Thr
        355                 360                 365

Ser Cys Leu Tyr Thr Asp Gln Asp Asn Gln Pro Ala Arg Val Ser Tyr
370                 375                 380

Phe Gly Gln Lys Met Lys Thr Ala Arg Ile Leu Ile Asn Thr Pro Ala
385                 390                 395                 400

Ser Gln Gly Gly Ile Gly Asp Leu Tyr Asn Phe Lys Leu Ala Pro Ser
                405                 410                 415

Leu Thr Leu Gly Cys Gly Ser Trp Gly Gly Asn Ser Ile Ser Glu Asn
            420                 425                 430

Val Gly Pro Lys His Leu Ile Asn Lys Lys Thr Val Ala Lys Arg Ala
        435                 440                 445

Glu Asn Met Leu Trp His Lys Leu Pro Lys Ser Ile Tyr Phe Arg Arg
450                 455                 460

Gly Ser Leu Pro Ile Ala Leu Asp Glu Val Ile Thr Asp Gly His Lys
465                 470                 475                 480

Arg Ala Leu Ile Val Thr Asp Arg Phe Leu Phe Asn Asn Gly Tyr Ala
                485                 490                 495

Asp Gln Ile Thr Ser Val Leu Lys Ala Ala Gly Val Glu Thr Glu Val
            500                 505                 510

Phe Phe Glu Val Glu Ala Asp Pro Thr Leu Ser Ile Val Arg Lys Gly
        515                 520                 525

Ala Glu Leu Ala Asn Ser Phe Lys Pro Asp Val Ile Ile Ala Leu Gly
530                 535                 540

Gly Gly Ser Pro Met Asp Ala Ala Lys Ile Met Trp Val Met Tyr Glu
545                 550                 555                 560

His Pro Glu Thr His Phe Glu Glu Leu Ala Leu Arg Phe Met Asp Ile
                565                 570                 575

Arg Lys Arg Ile Tyr Lys Phe Pro Lys Met Gly Val Lys Ala Lys Met
            580                 585                 590

Ile Ala Val Thr Thr Thr Ser Gly Thr Gly Ser Glu Val Thr Pro Phe
```

```
                595                 600                 605
Ala Val Val Thr Asp Asp Ala Thr Gly Gln Lys Tyr Pro Leu Ala Asp
            610                 615                 620

Tyr Ala Leu Thr Pro Asp Met Ala Ile Val Asp Ala Asn Leu Val Met
625                 630                 635                 640

Asp Met Pro Lys Ser Leu Cys Ala Phe Gly Leu Asp Ala Val Thr
                645                 650                 655

His Ala Met Glu Ala Tyr Val Ser Val Leu Ala Ser Glu Phe Ser Asp
                660                 665                 670

Gly Gln Ala Leu Gln Ala Leu Lys Leu Leu Lys Glu Tyr Leu Pro Ala
            675                 680                 685

Ser Tyr His Glu Gly Ser Lys Asn Pro Val Ala Arg Glu Arg Val His
690                 695                 700

Ser Ala Ala Thr Ile Ala Gly Ile Ala Phe Ala Asn Ala Phe Leu Gly
705                 710                 715                 720

Val Cys His Ser Met Ala His Lys Leu Gly Ser Gln Phe His Ile Pro
                725                 730                 735

His Gly Leu Ala Asn Ala Leu Leu Ile Cys Asn Val Ile Arg Tyr Asn
            740                 745                 750

Ala Asn Asp Asn Pro Thr Lys Gln Thr Ala Phe Ser Gln Tyr Asp Arg
                755                 760                 765

Pro Gln Ala Arg Arg Arg Tyr Ala Glu Ile Ala Asp His Leu Gly Leu
            770                 775                 780

Ser Ala Pro Gly Asp Arg Thr Ala Ala Lys Ile Glu Lys Leu Leu Ala
785                 790                 795                 800

Trp Leu Glu Thr Leu Lys Ala Glu Leu Gly Ile Pro Lys Ser Ile Arg
                805                 810                 815

Glu Ala Gly Val Gln Glu Ala Asp Phe Leu Ala Asn Val Asp Lys Leu
            820                 825                 830

Ser Glu Asp Ala Phe Asp Asp Gln Cys Thr Gly Ala Asn Pro Arg Tyr
835                 840                 845

Pro Leu Ile Ser Glu Leu Lys Gln Ile Leu Leu Asp Thr Tyr Tyr Gly
                850                 855                 860

Arg Asp Tyr Val Glu Gly Glu Thr Ala Ala Lys Lys Glu Ala Ala Pro
865                 870                 875                 880

Ala Lys Ala Glu Lys Lys Ala Lys Lys Ser Ala
                885                 890

<210> SEQ ID NO 69
<211> LENGTH: 423
<212> TYPE: PRT
<213> ORGANISM: Rhodococcus erythropolis

<400> SEQUENCE: 69

Ala Ile Glu Leu Asn Gln Ile Trp Asp Phe Pro Ile Lys Glu Phe His
1               5                   10                  15

Pro Phe Pro Arg Ala Leu Met Gly Val Gly Ala His Asp Ile Ile Gly
                20                  25                  30

Val Glu Ala Lys Asn Leu Gly Phe Lys Arg Thr Leu Leu Met Thr Thr
            35                  40                  45

Gly Leu Arg Gly Ser Gly Ile Ile Glu Glu Leu Val Gly Lys Ile Glu
        50                  55                  60

Tyr Gln Gly Val Glu Val Val Leu Tyr Asp Lys Val Glu Ser Asn Pro
65                  70                  75                  80
```

```
Lys Asp Tyr Asn Val Met Glu Ala Ala Leu Tyr Gln Lys Glu Lys
                85                  90                  95

Cys Asp Ser Ile Ile Ser Ile Gly Gly Ser Ser His Asp Ala Ala
            100                 105                 110

Lys Gly Ala Arg Val Ile Ala His Asp Gly Arg Asn Ile Asn Glu
        115                 120                 125

Phe Glu Gly Phe Ala Lys Ser Thr Asn Lys Glu Asn Pro Pro His Ile
    130                 135                 140

Ala Val Ser Thr Thr Ala Gly Thr Gly Ser Glu Thr Ser Trp Ala Tyr
145                 150                 155                 160

Val Ile Thr Asp Thr Ser Asp Met Asn Asn Pro His Lys Trp Val Gly
                165                 170                 175

Phe Asp Glu Ala Thr Ile Val Thr Leu Ala Ile Asp Asp Pro Leu Leu
            180                 185                 190

Tyr Tyr Thr Cys Pro Gln His Phe Thr Ala Tyr Cys Gly Phe Asp Val
        195                 200                 205

Leu Ala His Gly Ser Glu Pro Phe Val Ser Arg Leu Asp Phe Ala Pro
    210                 215                 220

Ser Leu Gly Asn Ala Ile Tyr Ser Val Glu Leu Val Ala Lys Asn Leu
225                 230                 235                 240

Arg Glu Ala Val Phe Glu Pro Arg Asn Leu Lys Ala Arg Glu Gly Met
                245                 250                 255

Met Asn Ala Gln Tyr Ile Ala Gly Gln Ala Phe Asn Ser Gly Gly Leu
            260                 265                 270

Gly Ile Val His Ser Ile Ser His Ala Val Ser Ala Phe Phe Asp Ser
        275                 280                 285

His His Gly Leu Asn Asn Ala Ile Ala Leu Pro Arg Val Trp Glu Tyr
    290                 295                 300

Asn Leu Pro Ser Arg Tyr Glu Arg Tyr Ala Gln Leu Ala Gly Ala Leu
305                 310                 315                 320

Gly Val Asp Thr Arg Asn Leu Thr Thr Val Gln Ala Ala Asp Ala Ala
                325                 330                 335

Val Glu Ala Ala Ile Arg Leu Ala Lys Asp Val Gly Ile Pro Asp Asn
            340                 345                 350

Phe Gly Gln Val Arg Thr Asp Ser Tyr Ala Lys Asn Gln Met Asn Thr
        355                 360                 365

Lys Lys Tyr Glu Gly Arg Gly Asp Val Ile Lys Gly Asp Glu Lys Thr
    370                 375                 380

Val Arg Ala Ile Ser Glu His Ile Gln Asp Asp Trp Cys Thr Pro Gly
385                 390                 395                 400

Asn Pro Arg Glu Val Thr Val Glu Ser Met Ile Pro Val Val Asp His
                405                 410                 415

Ala Ile Asn Lys Ser Tyr Phe
            420

<210> SEQ ID NO 70
<211> LENGTH: 395
<212> TYPE: PRT
<213> ORGANISM: Salmonella typhimurium

<400> SEQUENCE: 70

Met Gln Ala Glu Leu Gln Thr Ala Leu Phe Gln Ala Phe Asp Thr Leu
1               5                   10                  15

Asn Leu Gln Arg Val Lys Thr Phe Ser Val Pro Pro Val Thr Leu Cys
            20                  25                  30
```

Gly Leu Gly Ala Leu Gly Ala Cys Gly Gln Glu Ala Gln Ala Arg Gly
            35                  40                  45

Val Ser His Leu Phe Val Met Val Asp Ser Phe Leu His Gln Ala Gly
 50                  55                  60

Met Thr Ala Pro Leu Ala Arg Ser Leu Ala Met Lys Gly Val Ala Met
 65                  70                  75                  80

Thr Val Trp Pro Cys Pro Pro Gly Glu Pro Cys Ile Thr Asp Val Cys
                85                  90                  95

Ala Ala Val Ala Gln Leu Arg Glu Ala Ala Cys Asp Gly Val Val Ala
               100                 105                 110

Phe Gly Gly Gly Ser Val Leu Asp Ala Ala Lys Ala Val Ala Leu Leu
               115                 120                 125

Val Thr Asn Pro Asp Gln Thr Leu Ser Ala Met Thr Glu His Ser Thr
130                 135                 140

Leu Arg Pro Arg Leu Pro Leu Ile Ala Val Pro Thr Thr Ala Gly Thr
145                 150                 155                 160

Gly Ser Glu Thr Thr Asn Val Thr Val Ile Ile Asp Ala Val Ser Gly
                165                 170                 175

Arg Lys Gln Val Leu Ala His Ser Leu Met Pro Asp Val Ala Ile
               180                 185                 190

Leu Asp Ala Ala Val Thr Glu Gly Val Pro Pro Asn Val Thr Ala Met
               195                 200                 205

Thr Gly Ile Asp Ala Leu Thr His Ala Ile Glu Ala Tyr Ser Ala Leu
               210                 215                 220

Asn Ala Thr Pro Phe Thr Asp Ser Leu Ala Ile Gly Ala Ile Ala Met
225                 230                 235                 240

Ile Gly Lys Ser Leu Pro Lys Ala Val Gly Tyr Gly His Asp Leu Ala
               245                 250                 255

Ala Arg Glu Asn Met Leu Leu Ala Ser Cys Met Ala Gly Met Ala Phe
               260                 265                 270

Ser Ser Ala Gly Leu Gly Leu Cys His Ala Met Ala His Gln Pro Gly
               275                 280                 285

Ala Ala Leu His Ile Pro His Gly Gln Ala Asn Ala Met Leu Leu Pro
               290                 295                 300

Thr Val Met Gly Phe Asn Arg Met Val Cys Arg Glu Arg Phe Ser Gln
305                 310                 315                 320

Ile Gly Arg Ala Leu Thr Asn Lys Lys Ser Asp Asp Arg Asp Ala Ile
               325                 330                 335

Ala Ala Val Cys Glu Leu Ile Ala Glu Val Gly Gln Ser Lys Arg Leu
               340                 345                 350

Ala Asp Ala Gly Ala Lys Pro Glu His Tyr Ser Ala Trp Ala Gln Ala
               355                 360                 365

Ala Leu Glu Asp Ile Cys Leu Arg Ser Asn Pro Arg Thr Ala Thr Gln
               370                 375                 380

Ala Gln Ile Ile Asp Leu Tyr Ala Ala Ala Gly
385                 390                 395

<210> SEQ ID NO 71
<211> LENGTH: 395
<212> TYPE: PRT
<213> ORGANISM: Escherichia coli

<400> SEQUENCE: 71

Met Gln Asn Glu Leu Gln Thr Ala Leu Phe Gln Ala Phe Asp Thr Leu

```
               1               5                   10                  15
            Asn Leu Gln Arg Val Lys Thr Phe Ser Val Pro Pro Val Thr Leu Cys
                           20                  25                  30
            Gly Pro Gly Ser Val Ser Ser Cys Gly Gln Gln Ala Gln Thr Arg Gly
                           35                  40                  45
            Leu Lys His Leu Phe Val Met Ala Asp Ser Phe Leu His Gln Ala Gly
             50                      55                  60
            Met Thr Ala Gly Leu Thr Arg Ser Leu Thr Val Lys Gly Ile Ala Met
             65                  70                  75                  80
            Thr Leu Trp Pro Cys Pro Val Gly Glu Pro Cys Ile Thr Asp Val Cys
                               85                  90                  95
            Ala Ala Val Ala Gln Leu Arg Glu Ser Gly Cys Asp Gly Val Ile Ala
                           100                 105                 110
            Phe Gly Gly Gly Ser Val Leu Asp Ala Ala Lys Ala Val Thr Leu Leu
                           115                 120                 125
            Val Thr Asn Pro Asp Ser Thr Leu Ala Glu Met Ser Glu Thr Ser Val
             130                     135                 140
            Leu Gln Pro Arg Leu Pro Leu Ile Ala Ile Pro Thr Thr Ala Gly Thr
             145                 150                 155                 160
            Gly Ser Glu Thr Thr Asn Val Thr Val Ile Ile Asp Ala Val Ser Gly
                               165                 170                 175
            Arg Lys Gln Val Leu Ala His Ala Ser Leu Met Pro Asp Val Ala Ile
                           180                 185                 190
            Leu Asp Ala Ala Leu Thr Glu Gly Val Pro Ser His Val Thr Ala Met
                           195                 200                 205
            Thr Gly Ile Asp Ala Leu Thr His Ala Ile Glu Ala Tyr Ser Ala Leu
             210                     215                 220
            Asn Ala Thr Pro Phe Thr Asp Ser Leu Ala Ile Gly Ala Ile Ala Met
             225                 230                 235                 240
            Ile Gly Lys Ser Leu Pro Lys Ala Val Gly Tyr Gly His Asp Leu Ala
                               245                 250                 255
            Ala Arg Glu Ser Met Leu Leu Ala Ser Cys Met Ala Gly Met Ala Phe
                           260                 265                 270
            Ser Ser Ala Gly Leu Gly Leu Cys His Ala Met Ala His Gln Pro Gly
                           275                 280                 285
            Ala Ala Leu His Ile Pro His Gly Leu Ala Asn Ala Met Leu Leu Pro
             290                     295                 300
            Thr Val Met Glu Phe Asn Arg Met Val Cys Arg Glu Arg Phe Ser Gln
             305                 310                 315                 320
            Ile Gly Arg Ala Leu Arg Thr Lys Lys Ser Asp Asp Arg Asp Ala Ile
                               325                 330                 335
            Asn Ala Val Ser Glu Leu Ile Ala Glu Val Gly Ile Gly Lys Arg Leu
                           340                 345                 350
            Gly Asp Val Gly Ala Thr Ser His Tyr Gly Ala Trp Ala Gln Ala
                           355                 360                 365
            Ala Leu Glu Asp Ile Cys Leu Arg Ser Asn Pro Arg Thr Ala Ser Leu
             370                     375                 380
            Glu Gln Ile Val Gly Leu Tyr Ala Ala Ala Gln
             385                 390                 395

<210> SEQ ID NO 72
<211> LENGTH: 402
<212> TYPE: PRT
<213> ORGANISM: Bacillus subtilis
```

<400> SEQUENCE: 72

```
Met Thr Leu Asn Met Lys Val Glu Ser Met Gln Lys Phe His Thr Phe
1               5                   10                  15
Glu Ile Pro Thr Val Ile Lys His Gly Ile Gly Ala Ile Lys His Thr
                20                  25                  30
Gly Glu Glu Val Ala Ala Leu Gly Val Ser Lys Ala Leu Leu Val Thr
            35                  40                  45
Asp Pro Gly Ile Tyr Lys Ala Gly Val Ala Asp Pro Val Ile Glu Ser
        50                  55                  60
Leu Lys Glu Ala Gly Ile Glu Val Val Leu Phe Asn Lys Val Glu Pro
65                  70                  75                  80
Asn Pro Pro Val Arg Leu Val Asn Glu Gly Ser Glu Leu Tyr Lys Lys
                85                  90                  95
Glu Asn Cys Asn Gly Leu Val Ala Val Gly Gly Gly Ser Ser Met Asp
                100                 105                 110
Thr Ala Lys Ala Ile Gly Val Glu Ala Thr His Glu Gly Ser Val Leu
            115                 120                 125
Asp Tyr Glu Ala Ala Asp Gly Lys Lys Pro Leu Glu Asn Arg Ile Pro
        130                 135                 140
Pro Leu Thr Thr Ile Pro Thr Thr Ala Gly Thr Gly Ser Glu Val Thr
145                 150                 155                 160
Gln Trp Ala Val Ile Thr Asp Glu Glu Arg Glu Phe Lys Phe Asn Thr
                165                 170                 175
Gly Gly Pro Leu Ile Ala Ala His Leu Thr Ile Ile Asp Pro Glu Leu
                180                 185                 190
His Val Ser Met Pro Pro His Val Thr Ala Met Thr Gly Ile Asp Ala
            195                 200                 205
Leu Ala His Ala Ile Glu Cys Tyr Thr Met Lys Phe Ala Gln Pro Ile
        210                 215                 220
Thr Asp Ala Val Ala Leu Met Ala Ile Glu Tyr Ala Ala His Tyr Ile
225                 230                 235                 240
Lys Arg Ala Phe Ala Asp Gly Glu Asp Leu Glu Ala Arg Tyr Gly Met
                245                 250                 255
Ala Gln Ala Ala Met Leu Ala Gly Leu Ser Tyr Gly Ser Glu Ser Ala
                260                 265                 270
Gly Ala Ala His Ala Met Ser Gln Thr Leu Gly Gly Ile Ile Pro Val
            275                 280                 285
Ala His Gly Gln Cys Val Ala Ala Met Met Gly Pro Val Met Glu Tyr
        290                 295                 300
Asn Trp Lys Gly Tyr Pro Glu Lys Phe Ala Arg Ile Ala Lys Ala Phe
305                 310                 315                 320
Gly Ile Asp Thr Ser Lys Met Thr Thr Glu Glu Ala Ala Lys Ala Ser
                325                 330                 335
Val Asn Trp Met Tyr Asp Leu Val Glu Asp Leu Glu Val Pro Thr Leu
                340                 345                 350
Glu Glu Gln Gly Val Ser Pro Asp Met Ile Glu Arg Leu Ser Lys Glu
            355                 360                 365
Ala Met Lys Asp Pro Gln Thr Phe Gly Asn Pro Arg Asp Leu Asn Glu
        370                 375                 380
Lys Ala Tyr Asn Trp Ile Tyr Lys Arg Cys Phe Asn Leu Thr Pro Lys
385                 390                 395                 400
Thr Val
```

<210> SEQ ID NO 73
<211> LENGTH: 382
<212> TYPE: PRT
<213> ORGANISM: Escherichia coli

<400> SEQUENCE: 73

```
Met Ala Asn Arg Met Ile Leu Asn Glu Thr Ala Trp Phe Gly Arg Gly
1               5                   10                  15

Ala Val Gly Ala Leu Thr Asp Glu Val Lys Arg Arg Gly Tyr Gln Lys
            20                  25                  30

Ala Leu Ile Val Thr Asp Lys Thr Leu Val Gln Cys Gly Val Val Ala
        35                  40                  45

Lys Val Thr Asp Lys Met Asp Ala Ala Gly Leu Ala Trp Ala Ile Tyr
50                  55                  60

Asp Gly Val Val Pro Asn Pro Thr Ile Thr Val Val Lys Glu Gly Leu
65                  70                  75                  80

Gly Val Phe Gln Asn Ser Gly Ala Asp Tyr Leu Ile Ala Ile Gly Gly
                85                  90                  95

Gly Ser Pro Gln Asp Thr Cys Lys Ala Ile Gly Ile Ile Ser Asn Asn
            100                 105                 110

Pro Glu Phe Ala Asp Val Arg Ser Leu Glu Gly Leu Ser Pro Thr Asn
        115                 120                 125

Lys Pro Ser Val Pro Ile Leu Ala Ile Pro Thr Thr Ala Gly Thr Ala
130                 135                 140

Ala Glu Val Thr Ile Asn Tyr Val Ile Thr Asp Glu Glu Lys Arg Arg
145                 150                 155                 160

Lys Phe Val Cys Val Asp Pro His Asp Ile Pro Gln Val Ala Phe Ile
                165                 170                 175

Asp Ala Asp Met Met Asp Gly Met Pro Pro Ala Leu Lys Ala Ala Thr
            180                 185                 190

Gly Val Asp Ala Leu Thr His Ala Ile Glu Gly Tyr Ile Thr Arg Gly
        195                 200                 205

Ala Trp Ala Leu Thr Asp Ala Leu His Ile Lys Ala Ile Glu Ile Ile
210                 215                 220

Ala Gly Ala Leu Arg Gly Ser Val Ala Gly Asp Lys Asp Ala Gly Glu
225                 230                 235                 240

Glu Met Ala Leu Gly Gln Tyr Val Ala Gly Met Gly Phe Ser Asn Val
                245                 250                 255

Gly Leu Gly Leu Val His Gly Met Ala His Pro Leu Gly Ala Phe Tyr
            260                 265                 270

Asn Thr Pro His Gly Val Ala Asn Ala Ile Leu Leu Pro His Val Met
        275                 280                 285

Arg Tyr Asn Ala Asp Phe Thr Gly Glu Lys Tyr Arg Asp Ile Ala Arg
290                 295                 300

Val Met Gly Val Lys Val Glu Gly Met Ser Leu Glu Glu Ala Arg Asn
305                 310                 315                 320

Ala Ala Val Glu Ala Val Phe Ala Leu Asn Arg Asp Val Gly Ile Pro
                325                 330                 335

Pro His Leu Arg Asp Val Gly Val Arg Lys Glu Asp Ile Pro Ala Leu
            340                 345                 350

Ala Gln Ala Ala Leu Asp Asp Val Cys Thr Gly Gly Asn Pro Arg Glu
        355                 360                 365

Ala Thr Leu Glu Asp Ile Val Glu Leu Tyr His Thr Ala Trp
```

```
                370            375            380
```

<210> SEQ ID NO 74
<211> LENGTH: 381
<212> TYPE: PRT
<213> ORGANISM: Bacillus methanolicus

<400> SEQUENCE: 74

```
Met Thr Asn Phe Phe Ile Pro Pro Ala Ser Val Ile Gly Arg Gly Ala
1               5                  10                  15

Val Lys Glu Val Gly Thr Arg Leu Lys Gln Ile Gly Ala Lys Lys Ala
            20                  25                  30

Leu Ile Val Thr Asp Ala Phe Leu His Ser Thr Gly Leu Ser Glu Glu
        35                  40                  45

Val Ala Lys Asn Ile Arg Glu Ala Gly Leu Asp Val Ala Ile Phe Pro
    50                  55                  60

Lys Ala Gln Pro Asp Pro Ala Asp Thr Gln Val His Glu Gly Val Asp
65                  70                  75                  80

Val Phe Lys Gln Glu Asn Cys Asp Ala Leu Val Ser Ile Gly Gly Gly
                85                  90                  95

Ser Ser His Asp Thr Ala Lys Ala Ile Gly Leu Val Ala Ala Asn Gly
            100                 105                 110

Gly Arg Ile Asn Asp Tyr Gln Gly Val Asn Ser Val Glu Lys Pro Val
        115                 120                 125

Val Pro Val Val Ala Ile Thr Thr Thr Ala Gly Thr Gly Ser Glu Thr
    130                 135                 140

Thr Ser Leu Ala Val Ile Thr Asp Ser Ala Arg Lys Val Lys Met Pro
145                 150                 155                 160

Val Ile Asp Glu Lys Ile Thr Pro Thr Val Ala Ile Val Asp Pro Glu
                165                 170                 175

Leu Met Val Lys Lys Pro Ala Gly Leu Thr Ile Ala Thr Gly Met Asp
            180                 185                 190

Ala Leu Ser His Ala Ile Glu Ala Tyr Val Ala Lys Gly Ala Thr Pro
        195                 200                 205

Val Thr Asp Ala Phe Ala Ile Gln Ala Met Lys Leu Ile Asn Glu Tyr
    210                 215                 220

Leu Pro Lys Ala Val Ala Asn Gly Glu Asp Ile Glu Ala Arg Glu Ala
225                 230                 235                 240

Met Ala Tyr Ala Gln Tyr Met Ala Gly Val Ala Phe Asn Asn Gly Gly
                245                 250                 255

Leu Gly Leu Val His Ser Ile Ser His Gln Val Gly Gly Val Tyr Lys
            260                 265                 270

Leu Gln His Gly Ile Cys Asn Ser Val Asn Met Pro His Val Cys Ala
        275                 280                 285

Phe Asn Leu Ile Ala Lys Thr Glu Arg Phe Ala His Ile Ala Glu Leu
    290                 295                 300

Leu Gly Glu Asn Val Ser Gly Leu Ser Thr Ala Ala Ala Glu Arg
305                 310                 315                 320

Ala Ile Val Ala Leu Glu Arg Tyr Asn Lys Asn Phe Gly Ile Pro Ser
                325                 330                 335

Gly Tyr Ala Glu Met Gly Val Lys Glu Asp Ile Glu Leu Leu Ala
            340                 345                 350

Lys Asn Ala Phe Glu Asp Val Cys Thr Gln Ser Asn Pro Arg Val Ala
        355                 360                 365
```

```
Thr Val Gln Asp Ile Ala Gln Ile Ile Lys Asn Ala Leu
        370                 375                 380
```

<210> SEQ ID NO 75
<211> LENGTH: 387
<212> TYPE: PRT
<213> ORGANISM: Citrobacter freundii

<400> SEQUENCE: 75

```
Met Ser Tyr Arg Met Phe Asp Tyr Leu Val Pro Asn Val Asn Phe Phe
1               5                   10                  15

Gly Pro Asn Ala Ile Ser Val Val Gly Glu Arg Cys Lys Leu Leu Gly
            20                  25                  30

Gly Lys Lys Ala Leu Leu Val Thr Asp Lys Gly Leu Arg Ala Ile Lys
        35                  40                  45

Asp Gly Ala Val Asp Lys Thr Leu Thr His Leu Arg Glu Ala Gly Ile
    50                  55                  60

Asp Val Val Val Phe Asp Gly Val Glu Pro Asn Pro Lys Asp Thr Asn
65                  70                  75                  80

Val Arg Asp Gly Leu Glu Val Phe Arg Lys Glu His Cys Asp Ile Ile
                85                  90                  95

Val Thr Val Gly Gly Gly Ser Pro His Asp Cys Gly Lys Gly Ile Gly
            100                 105                 110

Ile Ala Ala Thr His Glu Gly Asp Leu Tyr Ser Tyr Ala Gly Ile Glu
        115                 120                 125

Thr Leu Thr Asn Pro Leu Pro Pro Ile Val Ala Val Asn Thr Thr Ala
    130                 135                 140

Gly Thr Ala Ser Glu Val Thr Arg His Cys Val Leu Thr Asn Thr Lys
145                 150                 155                 160

Thr Lys Val Lys Phe Val Ile Val Ser Trp Arg Asn Leu Pro Ser Val
                165                 170                 175

Ser Ile Asn Asp Pro Leu Leu Met Leu Gly Lys Pro Ala Pro Leu Thr
            180                 185                 190

Ala Ala Thr Gly Met Asp Ala Leu Thr His Ala Val Glu Ala Tyr Ile
        195                 200                 205

Ser Lys Asp Ala Asn Pro Val Thr Asp Ala Ala Ile Gln Ala Ile
    210                 215                 220

Arg Leu Ile Ala Arg Asn Leu Arg Gln Ala Val Ala Leu Gly Ser Asn
225                 230                 235                 240

Leu Lys Ala Arg Glu Asn Met Ala Tyr Ala Ser Leu Leu Ala Gly Met
                245                 250                 255

Ala Phe Asn Asn Ala Asn Leu Gly Tyr Val His Ala Met Ala His Gln
            260                 265                 270

Leu Gly Gly Leu Tyr Asp Met Pro His Gly Val Ala Asn Ala Val Leu
        275                 280                 285

Leu Pro His Val Ala Arg Tyr Asn Leu Ile Ala Asn Pro Glu Lys Phe
    290                 295                 300

Ala Asp Ile Ala Glu Phe Met Gly Glu Asn Thr Asp Gly Leu Ser Thr
305                 310                 315                 320

Met Asp Ala Ala Glu Leu Ala Ile His Ala Ile Ala Arg Leu Ser Ala
                325                 330                 335

Asp Ile Gly Ile Pro Gln His Leu Arg Asp Leu Gly Val Lys Glu Ala
            340                 345                 350

Asp Phe Pro Tyr Met Ala Glu Met Ala Leu Lys Asp Gly Asn Ala Phe
        355                 360                 365
```

```
Ser Asn Pro Arg Lys Gly Asn Glu Lys Glu Ile Ala Glu Ile Phe Arg
    370                 375                 380

Gln Ala Phe
385

<210> SEQ ID NO 76
<211> LENGTH: 387
<212> TYPE: PRT
<213> ORGANISM: Klebsiella pneumoniae

<400> SEQUENCE: 76

Met Ser Tyr Arg Met Phe Asp Tyr Leu Val Pro Asn Val Asn Phe Phe
1               5                   10                  15

Gly Pro Asn Ala Ile Ser Val Val Gly Glu Arg Cys Gln Leu Leu Gly
                20                  25                  30

Gly Lys Lys Ala Leu Leu Val Thr Asp Lys Gly Leu Arg Ala Ile Lys
            35                  40                  45

Asp Gly Ala Val Asp Lys Thr Leu His Tyr Leu Arg Glu Ala Gly Ile
        50                  55                  60

Glu Val Ala Ile Phe Asp Gly Val Glu Pro Asn Pro Lys Asp Thr Asn
65                  70                  75                  80

Val Arg Asp Gly Leu Ala Val Phe Arg Arg Glu Gln Cys Asp Ile Ile
                85                  90                  95

Val Thr Val Gly Gly Gly Ser Pro His Asp Cys Gly Lys Gly Ile Gly
                100                 105                 110

Ile Ala Ala Thr His Glu Gly Asp Leu Tyr Gln Tyr Ala Gly Ile Glu
            115                 120                 125

Thr Leu Thr Asn Pro Leu Pro Pro Ile Val Ala Val Asn Thr Thr Ala
        130                 135                 140

Gly Thr Ala Ser Glu Val Thr Arg His Cys Val Leu Thr Asn Thr Glu
145                 150                 155                 160

Thr Lys Val Lys Phe Val Ile Val Ser Trp Arg Asn Leu Pro Ser Val
                165                 170                 175

Ser Ile Asn Asp Pro Leu Leu Met Ile Gly Lys Pro Ala Ala Leu Thr
                180                 185                 190

Ala Ala Thr Gly Met Asp Ala Leu Thr His Ala Val Glu Ala Tyr Ile
            195                 200                 205

Ser Lys Asp Ala Asn Pro Val Thr Asp Ala Ala Ala Met Gln Ala Ile
        210                 215                 220

Arg Leu Ile Ala Arg Asn Leu Arg Gln Ala Val Ala Leu Gly Ser Asn
225                 230                 235                 240

Leu Gln Ala Arg Glu Asn Met Ala Tyr Ala Ser Leu Leu Ala Gly Met
                245                 250                 255

Ala Phe Asn Asn Ala Asn Leu Gly Tyr Val His Ala Met Ala His Gln
                260                 265                 270

Leu Gly Gly Leu Tyr Asp Met Pro His Gly Val Ala Asn Ala Val Leu
            275                 280                 285

Leu Pro His Val Ala Arg Tyr Asn Leu Ile Ala Asn Pro Glu Lys Phe
        290                 295                 300

Ala Asp Ile Ala Glu Leu Met Gly Glu Asn Ile Thr Gly Leu Ser Thr
305                 310                 315                 320

Leu Asp Ala Ala Glu Lys Ala Ile Ala Ala Ile Thr Arg Leu Ser Met
                325                 330                 335

Asp Ile Gly Ile Pro Gln His Leu Arg Asp Leu Gly Val Lys Glu Ala
```

```
            340             345             350
Asp Phe Pro Tyr Met Ala Glu Met Ala Leu Lys Asp Gly Asn Ala Phe
            355             360             365

Ser Asn Pro Arg Lys Gly Asn Glu Gln Glu Ile Ala Ala Ile Phe Arg
370             375             380

Gln Ala Phe
385

<210> SEQ ID NO 77
<211> LENGTH: 382
<212> TYPE: PRT
<213> ORGANISM: Saccharomyces cerevisiae

<400> SEQUENCE: 77

Met Ser Ser Val Thr Gly Phe Tyr Ile Pro Pro Ile Ser Phe Phe Gly
1               5                   10                  15

Glu Gly Ala Leu Glu Glu Thr Ala Asp Tyr Ile Lys Asn Lys Asp Tyr
                20                  25                  30

Lys Lys Ala Leu Ile Val Thr Asp Pro Gly Ile Ala Ala Ile Gly Leu
            35                  40                  45

Ser Gly Arg Val Gln Lys Met Leu Glu Glu Arg Asp Leu Asn Val Ala
50                  55                  60

Ile Tyr Asp Lys Thr Gln Pro Asn Pro Asn Ile Ala Asn Val Thr Ala
65                  70                  75                  80

Gly Leu Lys Val Leu Lys Glu Gln Asn Ser Glu Ile Val Val Ser Ile
                85                  90                  95

Gly Gly Gly Ser Ala His Asp Asn Ala Lys Ala Ile Ala Leu Leu Ala
            100                 105                 110

Thr Asn Gly Gly Glu Ile Gly Asp Tyr Glu Gly Val Asn Gln Ser Lys
            115                 120                 125

Lys Ala Ala Leu Pro Leu Phe Ala Ile Asn Thr Thr Ala Gly Thr Ala
130                 135                 140

Ser Glu Met Thr Arg Phe Thr Ile Ile Ser Asn Glu Glu Lys Lys Ile
145                 150                 155                 160

Lys Met Ala Ile Ile Asp Asn Asn Val Thr Pro Ala Val Ala Val Asn
                165                 170                 175

Asp Pro Ser Thr Met Phe Gly Leu Pro Pro Ala Leu Thr Ala Ala Thr
            180                 185                 190

Gly Leu Asp Ala Leu Thr His Cys Ile Glu Ala Tyr Val Ser Thr Ala
            195                 200                 205

Ser Asn Pro Ile Thr Asp Ala Cys Ala Leu Lys Gly Ile Asp Leu Ile
210                 215                 220

Asn Glu Ser Leu Val Ala Ala Tyr Lys Asp Gly Lys Asp Lys Lys Ala
225                 230                 235                 240

Arg Thr Asp Met Cys Tyr Ala Glu Tyr Leu Ala Gly Met Ala Phe Asn
                245                 250                 255

Asn Ala Ser Leu Gly Tyr Val His Ala Leu Ala His Gln Leu Gly Gly
            260                 265                 270

Phe Tyr His Leu Pro His Gly Val Cys Asn Ala Val Leu Leu Pro His
            275                 280                 285

Val Gln Glu Ala Asn Met Gln Cys Pro Lys Ala Lys Lys Arg Leu Gly
290                 295                 300

Glu Ile Ala Leu His Phe Gly Ala Ser Gln Glu Asp Pro Glu Glu Thr
305                 310                 315                 320
```

Ile Lys Ala Leu His Val Leu Asn Arg Thr Met Asn Ile Pro Arg Asn
            325                 330                 335

Leu Lys Glu Leu Gly Val Lys Thr Glu Asp Phe Glu Ile Leu Ala Glu
            340                 345                 350

His Ala Met His Asp Ala Cys His Leu Thr Asn Pro Val Gln Phe Thr
            355                 360                 365

Lys Glu Gln Val Val Ala Ile Ile Lys Lys Ala Tyr Glu Tyr
            370                 375             380

<210> SEQ ID NO 78
<211> LENGTH: 422
<212> TYPE: PRT
<213> ORGANISM: Schizosaccharomyces pombe

<400> SEQUENCE: 78

Met Ser Ile Leu Arg Ser Pro Phe Arg Leu Ile Arg Ser Pro Ala Arg
1               5                   10                  15

Phe Phe Pro Ser Leu Phe His Ser Ser Cys Asn Gln Ser Phe Thr Asn
            20                  25                  30

Gly Leu Lys His Gln Ser Thr Ser Ser Lys Ala Met Pro Val Ser Ala
            35                  40                  45

Phe Tyr Ile Pro Ser Phe Asn Leu Phe Gly Lys Gly Cys Leu Ala Glu
    50                  55                  60

Ala Ala Lys Gln Ile Lys Met Ser Gly Phe Lys Asn Thr Leu Ile Val
65                  70                  75                  80

Thr Asp Pro Gly Ile Ile Lys Val Gly Leu Tyr Asp Lys Val Lys Ala
                85                  90                  95

Leu Leu Glu Glu Gln Ser Ile Thr Val His Leu Tyr Asp Gly Val Gln
            100                 105                 110

Pro Asn Pro Thr Val Gly Asn Val Asn Gln Gly Leu Glu Ile Val Lys
            115                 120                 125

Lys Glu Asn Cys Asp Ser Met Val Ser Ile Gly Gly Ser Ala His
            130                 135                 140

Asp Cys Ala Lys Gly Ile Ala Leu Leu Ala Thr Asn Gly Gly Lys Ile
145                 150                 155                 160

Ala Asp Tyr Glu Gly Val Asp Lys Ser Ser Lys Pro Gln Leu Pro Leu
                165                 170                 175

Ile Ala Ile Asn Thr Thr Ala Gly Thr Ala Ser Glu Met Thr Arg Phe
            180                 185                 190

Ala Ile Ile Thr Glu Glu Thr Arg His Ile Lys Met Ala Ile Ile Asp
            195                 200                 205

Lys His Thr Met Pro Ile Leu Ser Val Asn Asp Pro Glu Thr Met Tyr
            210                 215                 220

Gly Leu Pro Pro Ser Leu Thr Ala Ala Thr Gly Met Asp Ala Leu Thr
225                 230                 235                 240

His Ala Val Glu Ala Tyr Val Ser Thr Ala Ala Asn Pro Ile Thr Asp
                245                 250                 255

Ala Cys Ala Val Lys Cys Ile Glu Leu Val Asn Lys Tyr Leu Lys Arg
            260                 265                 270

Ala Val Asp Asn Gly Lys Asp Glu Glu Ala Arg Asp Asn Met Ala Tyr
            275                 280                 285

Ala Glu Phe Leu Gly Gly Met Ala Phe Asn Asn Ala Ser Leu Gly Tyr
            290                 295                 300

Val His Ala Met Ala His Gln Leu Gly Gly Phe Tyr Gly Ile Pro His
305                 310                 315                 320

```
Gly Val Cys Asn Ala Val Leu Leu Ala His Val Gln Lys Phe Asn Ser
                325                 330                 335
Arg Asp Pro Arg Ala Asn Ala Arg Leu Gly Asp Ile Ala Phe His Leu
            340                 345                 350
Gly Cys Glu Glu His Thr Ala Glu Ala Leu Asp Arg Ile Ser Gln
        355                 360                 365
Leu Val Leu Glu Val Lys Ile Arg Pro His Leu Val Asp Leu Gly Val
    370                 375                 380
Lys Glu Lys Asp Phe Asp Val Leu Val Asp His Ala Met Lys Asp Ala
385                 390                 395                 400
Cys Gly Ala Thr Asn Pro Ile Gln Pro Thr His Asp Glu Val Lys Ala
                405                 410                 415
Ile Phe Lys Ser Ala Met
            420

<210> SEQ ID NO 79
<211> LENGTH: 383
<212> TYPE: PRT
<213> ORGANISM: Zymomonas mobilis

<400> SEQUENCE: 79

Met Ala Ser Ser Thr Phe Tyr Ile Pro Phe Val Asn Glu Met Gly Glu
1               5                   10                  15
Gly Ser Leu Glu Lys Ala Ile Lys Asp Leu Asn Gly Ser Gly Phe Lys
            20                  25                  30
Asn Ala Leu Ile Val Ser Asp Ala Phe Met Asn Lys Ser Gly Val Val
        35                  40                  45
Lys Gln Val Ala Asp Leu Leu Lys Ala Gln Gly Ile Asn Ser Ala Val
    50                  55                  60
Tyr Asp Gly Val Met Pro Asn Pro Thr Val Thr Ala Val Leu Glu Gly
65                  70                  75                  80
Leu Lys Ile Leu Lys Asp Asn Asn Ser Asp Phe Val Ile Ser Leu Gly
                85                  90                  95
Gly Gly Ser Pro His Asp Cys Ala Lys Ala Ile Ala Leu Val Ala Thr
            100                 105                 110
Asn Gly Gly Glu Val Lys Asp Tyr Glu Gly Ile Asp Lys Ser Lys Lys
        115                 120                 125
Pro Ala Leu Pro Leu Met Ser Ile Asn Thr Thr Ala Gly Thr Ala Ser
    130                 135                 140
Glu Met Thr Arg Phe Cys Ile Ile Thr Asp Glu Val Arg His Val Lys
145                 150                 155                 160
Met Ala Ile Val Asp Arg His Val Thr Pro Met Val Ser Val Asn Asp
                165                 170                 175
Pro Leu Leu Met Val Gly Met Pro Lys Gly Leu Thr Ala Ala Thr Gly
            180                 185                 190
Met Asp Ala Leu Thr His Ala Phe Glu Ala Tyr Ser Ser Thr Ala Ala
        195                 200                 205
Thr Pro Ile Thr Asp Ala Cys Ala Leu Lys Ala Ala Ser Met Ile Ala
    210                 215                 220
Lys Asn Leu Lys Thr Ala Cys Asp Asn Gly Lys Asp Met Pro Ala Arg
225                 230                 235                 240
Glu Ala Met Ala Tyr Ala Gln Phe Leu Ala Gly Met Ala Phe Asn Asn
                245                 250                 255
Ala Ser Leu Gly Tyr Val His Ala Met Ala His Gln Leu Gly Gly Tyr
```

```
                   260                 265                 270
Tyr Asn Leu Pro His Gly Val Cys Asn Ala Val Leu Leu Pro His Val
            275                 280                 285

Leu Ala Tyr Asn Ala Ser Val Ala Gly Arg Leu Lys Asp Val Gly
            290                 295                 300

Val Ala Met Gly Leu Asp Ile Ala Asn Leu Gly Asp Lys Glu Gly Ala
305                 310                 315                 320

Glu Ala Thr Ile Gln Ala Val Arg Asp Leu Ala Ala Ser Ile Gly Ile
                325                 330                 335

Pro Ala Asn Leu Thr Glu Leu Gly Ala Lys Lys Glu Asp Val Pro Leu
                340                 345                 350

Leu Ala Asp His Ala Leu Lys Asp Ala Cys Ala Leu Thr Asn Pro Arg
                355                 360                 365

Gln Gly Asp Gln Lys Glu Val Glu Glu Leu Phe Leu Ser Ala Phe
                370                 375                 380

<210> SEQ ID NO 80
<211> LENGTH: 383
<212> TYPE: PRT
<213> ORGANISM: Escherichia coli

<400> SEQUENCE: 80

Met Ala Ala Ser Thr Phe Phe Ile Pro Ser Val Asn Val Ile Gly Ala
1               5                   10                  15

Asp Ser Leu Thr Asp Ala Met Asn Met Met Ala Asp Tyr Gly Phe Thr
                20                  25                  30

Arg Thr Leu Ile Val Thr Asp Asn Met Leu Thr Lys Leu Gly Met Ala
                35                  40                  45

Gly Asp Val Gln Lys Ala Leu Glu Glu Arg Asn Ile Phe Ser Val Ile
            50                  55                  60

Tyr Asp Gly Thr Gln Pro Asn Pro Thr Thr Glu Asn Val Ala Ala Gly
65              70                  75                  80

Leu Lys Leu Leu Lys Glu Asn Asn Cys Asp Ser Val Ile Ser Leu Gly
                85                  90                  95

Gly Gly Ser Pro His Asp Cys Ala Lys Gly Ile Ala Leu Val Ala Ala
                100                 105                 110

Asn Gly Gly Asp Ile Arg Asp Tyr Glu Gly Val Asp Arg Ser Ala Lys
                115                 120                 125

Pro Gln Leu Pro Met Ile Ala Ile Asn Thr Thr Ala Gly Thr Ala Ser
130                 135                 140

Glu Met Thr Arg Phe Cys Ile Ile Thr Asp Glu Ala Arg His Ile Lys
145                 150                 155                 160

Met Ala Ile Val Asp Lys His Val Thr Pro Leu Leu Ser Val Asn Asp
                165                 170                 175

Ser Ser Leu Met Ile Gly Met Pro Lys Ser Leu Thr Ala Ala Thr Gly
                180                 185                 190

Met Asp Ala Leu Thr His Ala Ile Glu Ala Tyr Val Ser Ile Ala Ala
                195                 200                 205

Thr Pro Ile Thr Asp Ala Cys Ala Leu Lys Ala Val Thr Met Ile Ala
                210                 215                 220

Glu Asn Leu Pro Leu Ala Val Glu Asp Gly Ser Asn Ala Lys Ala Arg
225                 230                 235                 240

Glu Ala Met Ala Tyr Ala Gln Phe Leu Ala Gly Met Ala Phe Asn Asn
                245                 250                 255
```

-continued

| | | | | | | | | | | | | | |
|---|---|---|---|---|---|---|---|---|---|---|---|---|---|
| Ala | Ser | Leu | Gly 260 | Tyr | Val | His | Ala | Met 265 | Ala | His | Gln | Leu | Gly 270 | Gly | Phe |
| Tyr | Asn | Leu 275 | Pro | His | Gly | Val | Cys 280 | Asn | Ala | Val | Leu | Leu 285 | Pro | His | Val |
| Gln | Val | Phe 290 | Asn | Ser | Lys | Val 295 | Ala | Ala | Ala | Arg | Leu 300 | Arg | Asp | Cys | Ala |
| Ala 305 | Ala | Met | Gly | Val | Asn 310 | Val | Thr | Gly | Lys | Asn 315 | Asp | Ala | Glu | Gly | Ala 320 |
| Glu | Ala | Cys | Ile | Asn 325 | Ala | Ile | Arg | Glu | Leu 330 | Ala | Lys | Lys | Val | Asp 335 | Ile |
| Pro | Ala | Gly | Leu 340 | Arg | Asp | Leu | Asn | Val 345 | Lys | Glu | Glu | Asp | Phe 350 | Ala | Val |
| Leu | Ala | Thr 355 | Asn | Ala | Leu | Lys | Asp 360 | Ala | Cys | Gly | Phe | Thr 365 | Asn | Pro | Ile |
| Gln | Ala | Thr 370 | His | Glu | Glu | Ile | Val 375 | Ala | Ile | Tyr | Arg 380 | Ala | Ala | Met | |

MUTANT YQHD ENZYME FOR THE PRODUCTION OF A BIOCHEMICAL BY FERMENTATION

CROSS REFERENCE TO RELATED APPLICATIONS

This application is a §371 National Stage Application of PCT/EP2010/061106, filed Jul. 30, 2010, which claims priority to European Application No. 09166856.6, filed Jul. 30, 2009 and U.S. Provisional Application No. 61/229,866, filed Jul. 30, 2009.

BACKGROUND OF THE INVENTION

1. Field of the Invention

The present invention concerns a method for the production of a biochemical selected among acetol and 1,2-propanediol, 1,3-propanediol, ethylene glycol and 1,4-butanediol comprising culturing a microorganism modified for an improved production of the biochemical selected among acetol and 1,2-propanediol, 1,3-propanediol, ethylene glycol and 1,4-butanediol in an appropriate culture medium and recovery of the desired biochemical which may be further purified wherein the microorganism expresses a YqhD enzyme which catalytic efficiency toward NADPH is increased.

The present invention also relates to a mutant YqhD enzyme comprising at least one amino acid residue in the protein sequence of the parent enzyme replaced by a different amino acid residue at the same position wherein
- the mutant enzyme has retained more than 50% of the YqhD activity of the parent enzyme and
- the catalytic efficiency toward NADPH of the mutant YqhD is increased as compared with the catalytic efficiency toward NADPH of the parent enzyme.

1. Description of Related Art

YqhD was first identified as an 1,3-propanediol oxidoreductase catalysing the NADPH-dependent reduction of 3-hydroxypropionaldehyde (3-HPA) into 1,3-propanediol (PDO). This activity, endogenous to *E. coli*, was found to be more efficient that the recombinant NADH-dependent activity (encoded by dhaT gene from *Klebsiella pneumoniae*) used to built a PDO biosynthetic pathway in *E. coli* (Nakamura and Whited, 2003). The Du Pont de Nemours—Genencor project for the production of PDO in *E. coli* resulted in an industrial process with high titers and high yields (WO2001/012833 and WO2004/033646).

Expression of the yqhD gene was later used for purpose of production of PDO in different organisms, *E. coli* or *Saccharomyces cerevisiae* (Wang et al, 2007, Rao et al, 2008, Wang et al, 2009).

We showed that YqhD can act as a methylglyoxal reductase in the biosynthesis of 1,2-propanediol in *E. coli* (WO2008/116853).

The crystal structure of YqhD was determined with bound NADP co-factor. YqhD was shown to be a tetramer containing 1 atom of Zn by monomer. Alcohol dehydrogenase activity was recorded on several alcohols but with a weak affinity. However, the discovery of the presence of a modified (hydroxylated) co-factor in the enzyme cast doubt about the activity data provided (Sulzenbacher et al, 2004).

A more recent study characterized YqhD as an NADPH-dependent aldehyde reductase working on different substrates: acetaldehyde, propanaldehyde, butanaldehyde, acrolein and malondialdehyde (Perez et al, 2008). In this study, no activity was detected on short or medium chain alcohols. These authors proposed that YqhD was of relevance for the detoxification of toxic aldehydes inside the cell.

Miller et al (2009) showed that purified YqhD exhibited a furfural reductase activity. In this study, YqhD was found to have a very strong affinity for its NADPH co-factor with Km value for NADPH of 8 µM. With such an affinity, an active YqhD could scavenge NADPH normally used for the biosynthetic reactions of the cell and would thus inhibit growth.

Mutants of YqhD were produced by error-prone PCR in the aim of improving the enzyme activity towards 3-HPA for the production of 1,3-propanediol (Li et al, 2008). Two mutants, a double mutant (D99Q N147H) and a single mutant ((Q202A) were found to have an improved affinity (lower Km) for 3-HPA and an improved catalytic efficiency (Kcat/Km) for 3-HPA.

PDO is a monomer used in the production of polyester fibers, especially poly(trimethylene terephthalate) (PTT) and with potential applications in the manufacture of polyurethanes and cyclic compounds.

PDO can be produced by different chemical routes from i) acrolein, water and hydrogen, ii) ethylene oxide, carbon monoxide and water in the presence of phosphine and iii) glycerol and hydrogen in the presence of carbon monoxide. All of these methods have in common to be expensive and to generate waste streams containing toxic substances potentially harmful to the environment.

PDO is a typical product of glycerol fermentation and has not been found in anaerobic conversions of other organic substrates. Only very few organisms, all of them bacteria, are able to form it. They include enterobacteria of the genera *Klebsiella* (*K. pneumoniae*), *Enterobacter* (*E. agglomerans*) and *Citrobacter* (*C. freundii*), lactobacilli (*L. brevis* and *L. buchneri*) and clostridia of the *C. butyricum* and the *C. pasteurianum* group.

New bioprocesses for the production of PDO in recombinant *E. coli* have been disclosed in WO2001/012833 and WO2004/033646. These processes rely on the utilization of the yqhD gene encoding the YqhD enzyme for the last step of synthesis of PDO. Production of PDO from glycerol in a recombinant *Klebsiella* expressing the yqhD gene was described in CN1011260379. The same system applied to the production of PDO from glucose in a recombinant *Saccharomyces cerevisiae* was disclosed in CN101130782.

An alternative solution to produce PDO in recombinant organisms using a different biosynthetic pathway without glycerol as an intermediate has been proposed in patent application EP08173129.1. Production of other diols, such as ethylene glycol and 1,4-butanediol, according to the same scheme was also incorporated in the same patent application. All these processes are using the enzyme YqhD for the last step of synthesis.

1,2-propanediol or propylene glycol, a C3 dialcohol, is a widely-used chemical. It is a component of unsaturated polyester resins, liquid detergents, coolants, anti-freeze and de-icing fluids for aircraft. Propylene glycol has been increasingly used since 1993-1994 as a replacement for ethylene derivatives, which are recognised as being more toxic than propylene derivatives.

1,2-propanediol is currently produced by chemical means using a propylene oxide hydration process that consumes large amounts of water. Propylene oxide can be produced by either of two processes, one using epichlorhydrin, and the other hydroperoxide. Both routes use highly toxic substances. In addition, the hydroperoxide route generates by-products such as tert-butanol and 1-phenyl ethanol. For the production of propylene to be profitable, a use must be found for these by-products. The chemical route generally produces racemic 1,2-propanediol, whereas each of the two stereoisomers (R)1, 2-propanediol and (S)1,2-propanediol are of interest for certain applications (e.g. chiral starting materials for specialty chemicals and pharmaceutical products).

Acetol or hydroxyacetone (1-hydroxy- 2-propanone) is a C3 keto alcohol. This product is used in vat dyeing process in the textile industry as a reducing agent. It can advantageously replace traditional sulphur containing reducing agents in order to reduce the sulphur content in wastewater, harmful for the environment. Acetol is also a starting material for the chemical industry, used for example to make polyols or heterocyclic molecules. It possesses also interesting chelating and solvent properties.

Acetol is currently produced mainly by catalytic oxidation or dehydration of 1,2-propanediol. New processes starting from renewable feedstocks like glycerol are now proposed (see DE4128692 and WO 2005/095536). Currently, the production cost of acetol by chemical processes reduces its industrial applications and markets.

The disadvantages of the chemical processes for the production of 1,2-propanediol and acetol make biological synthesis an attractive alternative. 1,2-propanediol can be derived from central metabolism in three steps whereas acetol can be obtained in two steps. Methylglyoxal synthase converting dihydroxyacetone phosphate into methylglyoxal (MG) is the mandatory first step for the production of these two compounds. MG can then be converted to either acetol or D- or L-lactaldehyde by methylglyoxal reductases (Cameron et al, 1998, Bennett and San, 2001, Ko et al, 2005). As mentioned earlier, YqhD was shown to be very efficient in the production of acetol from methylglyoxal (WO2008/116853). Acetol or lactaldehyde can be converted to 1,2-propanediol by several enzymatic activities, especially glycerol dehydrogenase (encoded by gldA gene) or 1,2-propanediol oxidoreductase (encoded by fucO gene) in *E. coli* (Altaras and Cameron, 2000).

Processes for the production of 1,2-propanediol or acetol using different microorganisms, *Clostridium sphenoides* (DE3336051), *Klebsiella pneumoniae* (WO 2004/087936), recombinant yeast (WO 99/28481) or recombinant *E. coli* (WO 98/37204) have been disclosed. We recently proposed alternative approaches for the production of 1,2-propanediol or acetol (WO 2005/073364, WO 2008/116852, WO 2008/116848, WO 2008/116849, WO 2008/116851)), some of them relying on the use of the methylglyoxal reductase YqhD.

During their investigations on 1,2-propanediol production, the inventors identified new mutant YqhD enzymes with increased catalytic efficiency (increased Kcat/Km) toward NADPH, while keeping most of their specific activity for the conversion of methylglyoxal into acetol, as demonstrated in Example 2 by the characterization of purified enzymes. Use of these mutants is a key element in the design of more efficient processes for the production of all the products using a metabolic pathway based on YqhD activity.

SUMMARY

The present invention concerns a method for the production of a biochemical selected among acetol and 1,2-propanediol, 1,3-propanediol, ethylene glycol and 1,4-butanediol comprising culturing a microorganism modified for an improved production of the biochemical selected among acetol and 1,2-propanediol, 1,3-propanediol, ethylene glycol and 1,4-butanediol in an appropriate culture medium and recovery of the desired biochemical which may be further purified wherein the microorganism expresses a YqhD enzyme which catalytic efficiency toward NADPH is increased.

The present invention concerns a mutant YqhD enzyme comprising at least one amino acid residue in the protein sequence of the parent enzyme replaced by a different amino acid residue at the same position wherein the mutant enzyme has retained more than 50% of the YqhD activity of the parent enzyme and the catalytic efficiency toward NADPH of the mutant YqhD is increased as compared with the catalytic efficiency toward NADPH of the parent enzyme.

The invention also concerns a DNA sequence comprising a sequence coding for the mutant YqhD enzyme of the invention and a microorganism expressing such YqhD, which catalytic efficiency toward NADPH is increased, particularly a microorganism comprising a gene coding for the mutant YqhD enzyme of the invention.

BRIEF DESCRIPTION OF THE DRAWINGS

FIGS. 1-3 depict embodiments of the present invention as described herein.

DETAILED DESCRIPTION OF A PREFERRED EMBODIMENT

Figure 2:
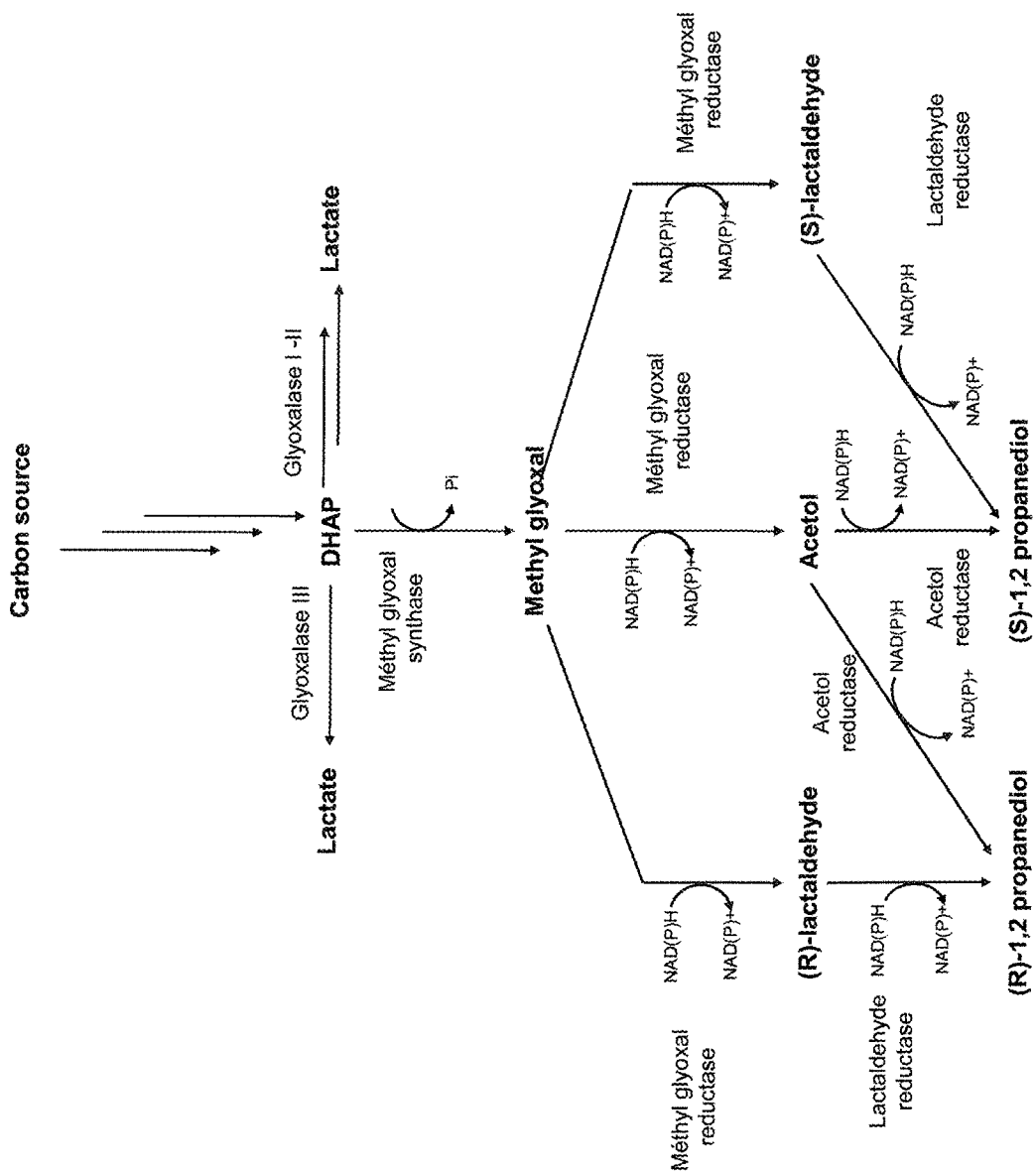

In the present application, terms are employed with their usual meaning, except when precised otherwise.

Microorganisms

A "microorganism" means all kind of unicellular organisms, including procaryotic organisms like bacteria, and eucaryotic organisms like yeasts. Preferentially, the microorganism is selected among the group consisting of bacteria, yeasts and fungi, more preferentially selected among Enterobacteriaceae, Bacillaceae, Streptomycetaceae, Clostridiaceae and Corynebacteriaceae. More preferentially, the microorganism is a species of *Escherichia, Klebsiella, Pantoea, Salmonella, Bacillus, Streptomyces, Clostridium* or *Corynebacterium*. Even more preferentially, the microorganism is selected among the group consisting of *Escherichia coli, Klebsiella pneumoniae, Thermoanaerobacterium thermosaccharolyticum, Clostridium sphenoides* or *Saccharomyces cerevisiae*.

As used herein, the term "modified microorganism" or "modified" or "recombinant" refer to a host cell that has a modification of its genome, e.g., as by addition of nucleic acid not naturally occurring in the organism or by a modification of nucleic acid naturally occurring in the host cell.

A "microorganism modified for an improved production of acetol and/or 1,2-propanediol and/or 1,3-propanediol and/or ethylene glycol and/or 1,4-butanediol" is a microorganism in which pathways to favour the production of the desired biochemical by conversion of a simple source of carbon have been modified. The microorganism modified for such improved production produces more of the desired biochemical than a native, unmodified microorganism.

Such microorganisms modified for an improved production of acetol and/or 1,2-propanediol and/or 1,3-propanediol and/or ethylene glycol and/or 1,4-butanediol are described in the scientific publications and patent applications cited in the "background of the invention" section, the content of said publications and patent applications being incorporated herein by reference.

In a preferred embodiment, the desired biochemical is 1,2-propanediol. The preferred biosynthetic pathways for the production of 1,2-propanediol with the microorganism of the invention are represented on FIG. 2. The person skilled in the art shall identify the enzymatic activities related to the pathway to be promoted and the other enzymatic activities to be attenuated.

Microorganisms modified for the improved production of 1,2-propanediol by conversion of methyl glyoxal are also disclosed in Cameron et al, 1998, Bennett and San, 2001, Ko et al, 2005 and WO 99/28481, WO 98/37204, WO 2005/073364, WO 2008/116852, WO 2008/116848, PCT/EP2009/053093 which content is incorporated herein by reference.

In the case of yeasts, the following modifications of the host organism are preferred:
attenuation of expression of at least one of the following genes: TPI1, NDE1, NDE2, GUT2, GPD1, GPD2, PDC1, PDC2, PDC5, PDC6, GLO1
enhancement of expression of GRE3 gene.

In the microorganisms of the invention, the DNA sequence coding for a mutant YqhD enzyme of the invention may be introduced in a vector for the expression and translation of the mutant YqhD enzyme. It can also be integrated in the chromosome of the said microorganism.

Integration of the DNA sequence can be done either entirely, or simply by introducing in the native gene of the microorganism, the mutation in the coding sequence by replacing the nucleotide(s) coding for the amino acid to be changed by the nucleotide(s) coding for the amino acid of the mutated protein.

Total, partial or specific nucleotides replacement in a gene of a microorganism is well known in the art of genetic engineering, including Sambrook J et al., Molecular cloning: a laboratory manual, Cold Spring Harbour Press, New York (2001), Ausubel F M et al., Current protocols in molecular biology, John Wiley and sons, New York (1999), Adams A et al., Methods in yeast genetics, Cold Spring Harbour Press, New York (1997).

The microorganism of the invention may additionally comprise a gene coding for a glycerol dehydrogenase (GlyDH) enzyme with reduced inhibition of its activity by NAD+ and/or its substrate and/or its product.

"The inhibition of which activity by NAD+ and/or its substrate and/or its product is reduced" means that the inhibition of the activity of the GlyDH enzyme expressed in the microorganism is less inhibited that the activity of the native GlyDH enzyme of the same microorganism. The inhibition of the activity of the GlyDH enzyme can be defined by the Inhibition Concentration 50 (IC50) or the Inhibition Constant (Ki) or any other techniques known by the skilled person. The reduced inhibition of the activity of the GlyDH enzyme means that the IC50 or the Ki of the GlyDH enzyme of the invention is higher than the IC50 or the Ki of the native GlyDH enzyme. The skilled person knows the relation between IC50 and Ki, and their meaning on the activity of enzyme according to the classic Michaelis-Menten kinetics.

Preferably, the activity of the GlyDH enzyme is less inhibited than the native GlyDH enzyme of *E. coli*. In a preferred embodiment, the enzyme activity is less inhibited for at least two members of the group consisting of NAD+, the enzyme's substrate and the enzyme's product. More preferably the enzyme activity is less inhibited by the three of NAD+, its substrate and its product.

The enzyme "substrate" is dihydroxyacetone, hydroxyacetone, methylglyoxal, lactaldehyde, glyceraldehyde, glycolaldehyde and derivatives thereof.

The enzyme "product" is the molecule obtained from the selected substrate by reduction of the carbonyl function.

For the production of 1,2-propanediol, the substrate is hydroxyacetone and the product is 1,2-propanediol.

Particularly the GlyDH enzyme is a mutant enzyme, wherein
the mutant enzyme has retained more than 50% of the activity of the parent enzyme and
the glycerol dehydrogenase activity of the mutant GlyDH is less inhibited by NAD+ and/or by its substrate as compared to the parent enzyme and/or by its product as compared to the parent enzyme.

Preferably, the mutant GlyDH preferably comprises at least a mutation selected among the group consisting of A160T and T120N, and combinations thereof. The aminoacids positions are given by reference to the GlyDH sequence of *E. coli*, encoded by the gldA gene. The person skilled in the art shall find the corresponding aminoacids in sequences from other organisms by standard techniques of sequence alignment.

The microorganism of the invention may also comprise, additionally, a gene coding for a methylglyoxal synthase (MGS) enzyme which activity is not inhibited by orthophosphate, "Not inhibited by orthophosphate" or "lacking inhibition by orthophosphate" means that no inhibition by orthophosphate is identified in an activity assay, when activity of the enzyme is studied in presence of orthophosphate.

In addition, kinetics of the MGS enzyme of the invention follows Michaelis-Menten kinetics regardless of the presence or absence of orthophosphate. Kinetics of the native enzyme follow a Michaelis-Menten model only in the absence of orthophosphate. The presence of orthophosphate makes the kinetic profile (specific activity over substrate concentration) of the native enzyme to become sigmoidal, which denotes the allosteric inhibition by orthophosphate.

Such enzyme has preferably a methylglyoxal synthase activity of at least 50% of the activity of the methylglyoxal synthase of *E. coli*.

Particularly, the MGS enzyme is a mutant MGS enzyme wherein
the mutant enzyme has retained more than 50% of the activity of the parent enzyme and
the methylglyoxal synthase activity of the mutant MGS is not inhibited by orthophosphate as compared to the parent enzyme.

Preferably the mutant MGS comprises at least a mutation selected among the group consisting of H21Q, A95V and V116L, and combinations thereof. The aminoacids positions are given by reference to the MgsA sequence of *E. coli*. The person skilled in the art shall find the corresponding aminoacids in sequences from other organisms by standard techniques of sequence alignment.

YqhD Enzyme

The invention concerns an YqhD enzyme which catalytic efficiency toward NADPH is increased, a microorganism comprising the same and a method for the production of a desired biochemical by fermentation of said microorganism on a culture medium comprising a simple source of carbon.

An YqhD enzyme "which catalytic efficiency toward NADPH is increased" means that the catalytic efficiency towards NADPH of the YqhD enzyme expressed in the microorganism is higher than the catalytic efficiency towards NADPH of the native YqhD enzyme of the same microorganism. The catalytic efficiency is defined as the ratio between the catalytic constant (Kcat) and the Michaelis constant (Km). Increase of catalytic efficiency of YqhD enzyme means that the Kcat of the enzyme is increased or that the Km of the enzyme is decreased. In a preferred embodiment the Kcat of the YqhD enzyme is increased and the Km of the YqhD enzyme is decreased.

Preferably, the catalytic efficiency towards NADPH of the YqhD enzyme is higher than the efficiency of the native YqhD enzyme of *E. coli*.

In another aspect of the invention, the YqhD enzyme is more sensitive to inhibition by $NADP^+$. Inhibition of catalytic activity of YqhD by $NADP^+$ is higher than the inhibition of catalytic activity of the native YqhD enzyme of *E. coli*.

In a preferred embodiment of the invention, the catalytic efficiency towards NADPH of the YqhD enzyme and its sensitivity to $NADP^+$ are higher than the efficiency and sensitivity of the native YqhD of *E. coli*.

Catalytic efficiency of the enzyme towards NADPH and its sensitivity to $NADP^+$ can be measured by methods known to the person skilled in the art, and particularly as disclosed in example 3.

Such enzyme has preferably an enzymatic activity of at least 50% of the activity of the YqhD of *E. coli*, more preferably at least 60% of the activity of the YqhD of *E. coli*.

YqhD is reducing methylglyoxal with NADPH as a cofactor and the methylglyoxal reductase activity of the enzyme can be measured by means known to the person skilled in the art. Such an activity assay is well known in the art and can be carried out as disclosed in Example 2.

The enzymes may be obtained by various ways known to the person skilled in the art.

A first approach consists in screening native enzymes of various organisms for their increased catalytic efficiency towards NADPH.

A second approach consists in inducing mutation(s) in enzymes of known organisms and selecting the enzymes for increased catalytic efficiency towards NADPH. Mutations may be induced by methods known in the art such as subjecting the microorganism to mutagenic agents. Another method to induce mutations is to growth the microorganism under selection pressure and identify the microorganism growing under such conditions and select the enzymes obtained for their increased catalytic efficiency towards NADPH.

Other methods are also known in the art to obtain mutations by shuffling DNA from various origins and select the proteins encoded by the shuffled DNA so obtained based on their methylglyoxal reductase activity and their increased catalytic efficiency towards NADPH.

In a particular embodiment of the invention, the inventors obtained several mutants YqhD retaining their methylglyoxal reductase activity and having an increased catalytic efficiency towards NADPH by selecting strains modified for an improved production of 1,2-propanediol cultured under selection pressure as disclosed in WO 2005/073364 and as shown in Example 1.

The present invention concerns a mutant YqhD enzyme comprising at least one amino acid residue in the protein sequence of the parent enzyme replaced by a different amino acid residue at the same position wherein the mutant enzyme has retained more than 50% of the YqhD activity of the parent enzyme and the catalytic efficiency toward NADPH of the mutant YqhD is increased as compared with the catalytic efficiency toward NADPH of the parent enzyme.

"Mutant" means that a mutation was introduced in a protein sequence by a person. According to the invention, a mutant enzyme is an enzyme comprising at least one amino acid difference with a parent enzyme. In the mutant enzyme of the invention, any change in amino acids may be introduced, either by directed mutagenesis or random mutagenesis, but also chimerical enzymes can be constructed, comprising parts of a second enzyme replacing corresponding parts of the parent enzyme.

The "parent enzyme" is the enzyme prior mutation. The parent enzyme may be of any origin, natural, isolated from another organism or synthetic.

The method for determining that the mutated YqhD has retained "more than 50%" of the activity of the parent enzyme is well known in the art and disclosed in Example 2.

Indeed, the skilled person shall choose the level of desired activity according to the final use of mutant YqhD. Indeed, when a high activity is necessary, the skilled person will choose a mutant having more than 80% of activity, compared to the non mutated parent enzyme, more preferably more than 90% of activity. In other cases, selecting a mutant YqhD with an activity around and above 50% compared to the parent enzyme may prevent additional modifications in a microorganism, like modifying the promoter to lower the level of expression of the enzyme.

According to the invention, "increased catalytic efficiency towards NADPH" means that the catalytic efficiency towards NADPH is at least 80 000 M−1 s−1, more preferably at least 100 000 M−1 s−1.

Methods used to calculate the kinetic parameters of the enzymes are given in Examples 2 and 3 but can also be found e.g. in Segel, I H, Enzyme Kinetics, John Wiley & Sons (1993).

In a preferred embodiment, the mutant YqhD enzyme of the invention comprises at least one amino acid residue of an identified region in the native parent YqhD enzyme replaced by a different amino acid residue at the same position.

The inventors have identified mutants YqhD comprising at least one amino acid residue of one of the following Conserved Regions in the native parent YqhD which has been replaced by a different amino acid residue at the same position:

$$-Glu-Xa1-Xa2-Xa3-Xa4-Xa5-Xa6-Xa7-Xa8- \quad (CR1)$$

wherein

Xa1 represents Met, Ser, Thr and Val, preferably Met and Val,

Xa2 represents Asn, Asp, Ser and Thr, preferably Thr,

Xa3 represents Ala, Arg, Asn, Cys, Gln, Ile, Pro, Ser, Thr and Trp,

Xa4 represents Ala, Asn, Asp, Gly, His, Ile, Leu, Phe, Trp and Val,

Xa5 represents Ala, Cys, Gly, Phe, Ser, Thr, Trp and Tyr,

Xa6 represents Gly, Ile and Val, preferably Val,
Xa7 represents Ala, Ile, Leu and Val, preferably Ile, and
Xa8 represents Glu, Gly, Ile, Ser and Thr, preferably Thr,

```
-His-Xa9-X10-X11-X12-X13-X14-X15-X16-X17-(CR2)
``` wherein
Xa9 represents Ala and Gly, preferably Gly,
X10 represents Arg, Cys, Gln, Glu, Gly, Ile, Leu, Pro and Val,
X11 represents Ala, Asn, Cys, Gly, Met and Thr,
X12 represents Asn, H is, Leu and Val, preferably Asn,
X13 represents Ala, Ser, Thr and Tyr, preferably Ala,
X14 represents Ala, Ile, Leu, Met and Val, preferably Ile and Val,
X15 represents Ala, Asn, Leu, Met, Phe, Thr, Tyr and Val, preferably Leu,
X16 represents Ile, Leu, Met, Phe and Thr, preferably Leu, and
X17 represents Ala, Cys, Gly, Pro and Thr, preferably Pro.

Figure 1END:
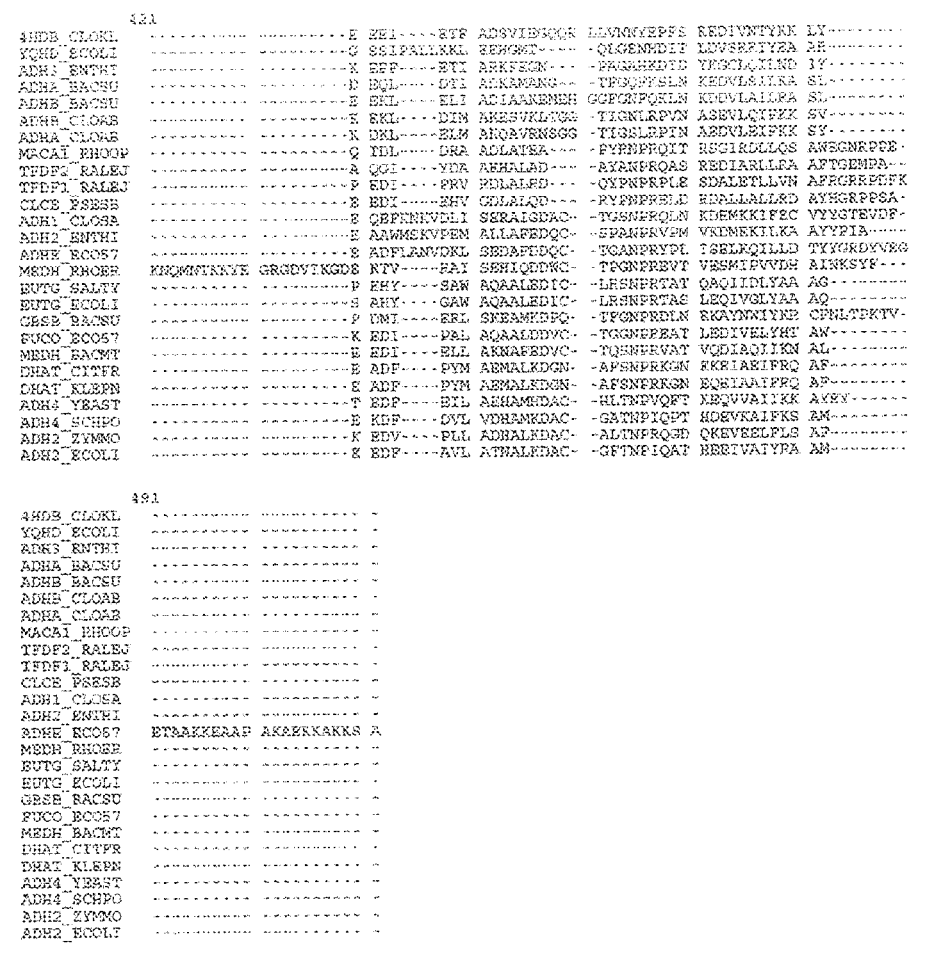

These conserved regions can be identified in different YqhD enzymes by simple sequence alignment using standard sequence alignment tools such as ClustalW2, Kalign, MAFFT, MUSCLE or T-coffee, all available on the European Bioinformatics Institute website. A sequence alignment of several YqhD enzymes of different species is given in FIG. 1.

Amino acids numbers in the present application are given by reference to the proteins of *E. coli*.

It can be found in FIG. 1 that CR1 correspond to amino acids 145 to 153 of *E. coli* YqhD and CR2 correspond to amino acids 281 to 290 of *E. coli* YqhD.

According to the invention, the mutant YqhD can have at least one mutation in one of CR1 or CR2, and can have at least two mutations in CR1 and CR2.

"At least" in such context means that the mutated enzyme may have other mutations, but nor related to the identified Conserved Regions CR1 and CR2. These other non identified mutations have no substantial impact on the mutated enzyme of the invention, provided that:
 the mutant enzyme has retained more than 50% of the YqhD activity of the parent enzyme and
 the catalytic efficiency toward NADPH of the mutant YqhD is increased as compared with the catalytic efficiency toward NADPH of the parent enzyme.

In preferred embodiments, the amino acid residue in the conserved regions CR1 and CR2 in the native parent YqhD replaced by a different amino acid residue at the same position in the mutant YqhD is selected among the group consisting of amino acid Xa4 in CR1 and amino acid X13 in CR2 and combinations thereof.

Xa4 correspond to amino acid 149 in the YqhD sequence of *E. coli*. X13 corresponds to amino acid 286 in the YqhD sequence of *E. coli*.

Particularly, the mutated YqhD of the invention comprises at least one of the mutations selected among the group consisting in G149E, G149S, A286T and combinations thereof, the aminoacid positions being given by reference to the YqhD sequence of *E. coli*.

More preferably, the mutated YqhD of the invention comprises at least one of the following amino acid sequence in conserved regions CR1 and CR2:

```
CR1: Glu Ser Asn Ala Ser Ala Val Ile Ser or

Glu Ser Asn Ala Glu Ala Val Ile Ser

CR2: His Ala Gln Thr Leu Thr Ile Val Leu Pro
``` the amino acid residue marked in bold and underlined corresponding to the amino acid in the mutant YqhD different from the amino acid in the parent YqhD.

Particularly, the mutant YqhD of the invention has at least 25% sequence identity compared to the YqhD sequence of *E. coli*, provided that it comprises at least one of the following mutations in CR1 and/or CR2:

```
CR1: Glu Ser Asn Ala Ser Ala Val Ile Ser or

Glu Ser Asn Ala Glu Ala Val Ile Ser

CR2: His Ala Gln Thr Leu Thr Ile Val Leu Pro.
```

Sequence identity is defined after sequence alignment of the YqhD sequence of *E. coli* with the protein sequence to be compared using CLUSTALW2 available on the EBI website (see above) with default parameters. The sequence identity is then calculated with the sequence alignment by the ratio of the number of identical amino acids at the same position with the total number of amino acids in the reference sequence (*E. coli*).

Preferably, the mutant YqhD has at least 35% sequence identity.

In most preferred embodiments, the mutant YqhD of the invention comprises the sequence selected among the group consisting of YqhD identified in SEQ ID NO 1, SEQ ID NO 2 and SEQ ID NO 3.

DNA, Vectors, Genes

The present invention also concerns a DNA sequence comprising a sequence coding for the mutant YqhD of the invention. The sequence sequence coding for the mutant YqhD of the invention is not a limiting factor by itself. The skilled person can easily obtain the sequence of a native YqhD from a microorganism and introduce in the coding sequence the mutation(s) to be introduced in the protein by changing one or more appropriate nucleotide.

The skilled person can also perform a mutagenesis in the sequence of a microorganism, and isolate the mutated DNA sequence by standard methods.

Mutations can be introduced by site-directed mutagenesis by usual methods like Polymerase Chain Reaction (PCR, see Sambrook J et al., Molecular cloning: a laboratory manual, Cold Spring Harbour Press, New York (2001), Ausubel F M et al., Current protocols in molecular biology, John Wiley and sons, New York (1999), Adams A et al., Methods in yeast genetics, Cold Spring Harbour Press, New York (1997)), or by random mutagenesis techniques, such as use of mutagenic agents (Ultra-Violet rays or chemical agents like nitrosoguanidine (NTG) or ethylmethanesulfonate (EMS)) or use of PCR techniques (DNA shuffling or error-prone PCR).

The person skilled in the art can also prepare synthetic genes with preferred codons selected for an improved expression in a specific organism. Codons usages by various organisms are well known in the art and several companies are proposing the manufacture of synthetic genes with codon optimization.

The sequence of the invention can be isolated, consisting in the coding sequence as defined above, or within a gene comprising regulatory elements upstream and downstream the coding sequence for its expression in a specific organism.

The sequence can also be present in a vector, for its replication (replication vector) or for the expression and translation of the mutated protein of the invention in a microorganism (expression vector). Such vectors are known in the art and not a limiting factor for the definition of the invention.

Said genes and vectors are also part of the invention.

Preferably, the DNA sequence of the invention is in a microorganism with regulatory elements allowing expression and translation of the mutated YqhD of the invention.

Production of the Desired Biochemical

The invention also concerns a method for the production of acetol and/or 1,2-propanediol and/or 1,3-propanediol and/or ethylene glycol and/or 1,4-butanediol by fermentation comprising culturing a microorganism of the invention, modified for an improved production of acetol and/or 1,2-propanediol and/or 1,3-propanediol and/or ethylene glycol and/or 1,4-butanediol and recovery of the acetol and/or 1,2-propanediol and/or 1,3-propanediol and/or ethylene glycol and/or 1,4-butanediol.

In a particular embodiment, the recovered acetol and/or 1,2-propanediol and/or 1,3-propanediol and/or ethylene glycol and/or 1,4-butanediol is purified is purified.

Methods for the purification acetol and/or 1,2-propanediol and/or 1,3-propanediol and/or ethylene glycol and/or 1,4-butanediol are known in the art.

In a preferred embodiment, the desired biochemical is 1,2-propanediol. Purification of 1,2-propanediol are known in the art and described in U.S. Pat. No. 5,076,896 and WO 2007/074066.

Advantageously, the production is done by fermentation in a batch, fed-batch or continuous process, according to processes known to the person skilled in the art of microorganisms fermentation. Preferably, the production is done by fermentation in a fed-batch process.

Culture Medium and Carbon Source

In the production method of the invention, the microorganism is cultured on an appropriate culture medium.

An "appropriate culture medium" means a medium of known molecular composition adapted to the growth of the micro-organism. In particular, said medium contains at least a source of phosphorus and a source of nitrogen. Said appropriate medium is for example a mineral culture medium of known set composition adapted to the bacteria used, containing at least one carbon source. Said appropriate medium may also designate any liquid comprising a source of nitrogen and/or a source of phosphorus, said liquid being added and/or mixed to the source of sucrose. In particular, the mineral growth medium for Enterobacteriaceae can thus be of identical or similar composition to M9 medium (Anderson, 1946), M63 medium (Miller, 1992) or a medium such as defined by Schaefer et al. (1999).

The carbon source 'glucose' can be replaced in this medium by any other carbon source, in particular by sucrose or any sucrose-containing carbon source such as sugarcane juice or sugar beet juice.

A "carbon source" or "carbon substrate" means any carbon source capable of being metabolized by a microorganism wherein the substrate contains at least one carbon atom.

Preferably, the carbon source is selected among the group consisting of glucose, sucrose, mono- or oligosaccharides, starch or its derivatives or glycerol and mixtures thereof.

Indeed the microorganisms used in the method of the present invention can be modified to be able to grow on specific carbon sources when the non modified microorganism cannot grow on the same source of carbon, or grow at to low rates. These modifications may be necessary when the source of carbon is a byproduct of biomass degradation such as by-products of sugarcane including; filter cake from clarification of raw juice and different kind of molasses.

FIG. 1 represents the alignment of 23 protein sequences of YqhD or homologous enzymes of various sources. The sequences 4HDB_CLOKL (SEQ ID NO:55); YQHD_E-COLI (SEQ ID NO: 56); ADH3_ENTHI (SEQ ID NO: 57); ADHA_BACSU (SEQ ID NO: 58); ADHB_BACSU (SEQ ID NO: 59); ADHB_CLOAB (SEQ ID NO: 60); ADHA_CLOAB (SEQ ID NO: 61); MACA1_RHOOP (SEQ ID NO: 62); TFDF2_RALEJ (SEQ ID NO: 63); TFDF1_RALEJ (SEQ ID NO: 64); CLCE_PSESB (SEQ ID NO: 65); ADH1_CLOSA (SEQ ID NO: 66); ADH2_ENTHI (SEQ ID NO: 67); ADHE_ECO57 (SEQ ID NO: 68); MEDH_RHOER (SEQ ID NO: 69); EUTG_SALTY (SEQ ID NO: 70); EUTG_ECOLI (SEQ ID NO: 71); GBSB_BACSU (SEQ ID NO: 72); FUCO_ECO57 (SEQ ID NO: 73); MEDH_BACMT (SEQ ID NO: 74); DHAT_CITFR (SEQ ID NO: 75); DHAT_KLEPN (SEQ ID NO: 76); ADH4_YEAST (SEQ ID NO: 77); ADH4_SCHPO (SEQ ID NO: 78); ADH2_ZYMMO (SEQ ID NO: 79); ADH2_ECOLI (SEQ ID NO: 80) were obtained from the UniProt Knowledge Base (The UniProt consortium (2008)) and the alignment made using MUSCLE with default parameters.

FIG. 2 represents the metabolic pathways for the production of lactic acid, acetol and 1,2-propanediol in the microorganisms of the invention.

Figure 3:
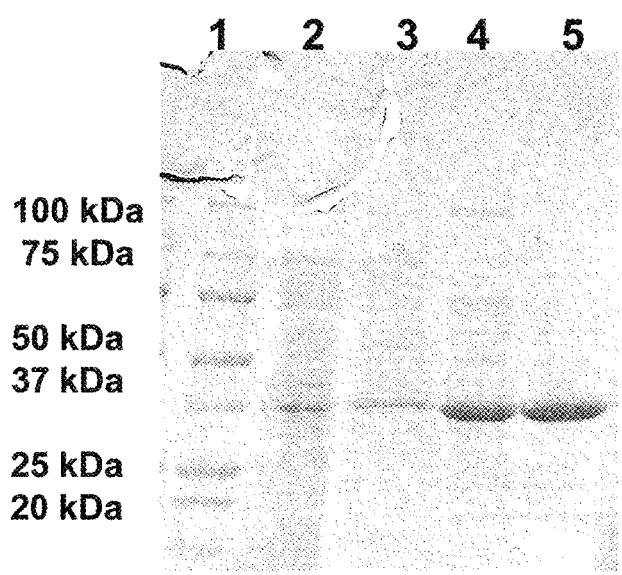

FIG. 3 represents an analysis on SDS 4-15% gradient polyacrylamide gel the different purification steps of the protein yqhD. Lane 1: Molecular weight marker, Lane 2: Crude extract, Lane 3, Ammonium sulphate precipitate dissolved, Lane 4, HiTrap PhenylHP column pool, Lane 5, Superdex 200 pool.

EXAMPLES

Example 1

Evolution of 2 Modified Strains of E. coli MG1655 in Chemostat Culture and Identification of 2 Mutant YqhD Enzymes in the Evolved Clones The construction of the strains E. coli MG1655 lpd* ΔtpiA, ΔpflAB, ΔadhE, ΔldhA::Cm, ΔgloA, ΔaldA, ΔaldB, Δedd (strain 1) and E. coli MG1655 lpd* ΔtpiA, ΔpflAB, ΔadhE, ΔldhA, ΔgloA, ΔaldA, ΔaldB, Δedd, ΔarcA, Δndh::Km (strain 2) were previously described in patent application WO 2008/116852.

To evolve them toward improved 1,2 propanediol production, the 2 strains were cultivated in continuous culture, either under anaerobic conditions, or under microaerobic conditions (1% oxygen) in the culture medium MPG (given in patent application WO 2008/116852) with 0.42 or 0.84 g/l sodium nitrate, with excess glucose (from 20 g/l initially with addition if the glucose becomes exhausted). The temperature was set at 37° C., the pH was regulated at 6.5 by addition of base and the dilution rate of the chemostat was set between 0.04 $h^{-1}$ and 0.08 $h^{-1}$. The evolution of the strain in the chemostats was followed by the increase of the biomass concentration coupled with the increase of the concentrations of the product, 1,2-propanediol and the co-product acetate, over several weeks. This denoted the improvement of the performances of the strains. When the cultures reached a steady state with no further increase of the concentrations under these conditions, the evolution was done.

The characteristics of the strains before and after evolution were assessed. Single colonies representing individual clones were isolated on Petri dishes. These clones were assessed using the initial strain as control in an Erlenmeyer flask assay, using the same medium MPG used in the chemostat culture, but buffered with MOPS. Among these clones, several presented better 1,2-propanediol specific production rates as compared to the control. The results obtained on the best clone for each condition of evolution are reported in Table 1 and 2 below.

TABLE 1

Comparison of the best evolved clone obtained after 66 days of evolution under anaerobic conditions with the initial strain

| Strain *E. coli* MG1655 lpd* ΔtpiA ΔpflAB ΔadhE ΔldhA::Cm ΔgloA Δald, ΔaldB Δedd (Strain 1) | Initial strain before evolution (performances measured after 2 days of culture) | Best evolved clone (performances measured after 2 days of culture) |
|---|---|---|
| Glucose specific consumption rate (g glucose/g biomass/h) | 0.12 | 0.21 (+75%) |
| 1,2-propanediol specific production rate (g 1,2-propanediol/g biomass/h) | 0.02 | 0.07 (+250%) |
| 1,2-propanediol + hydroxyacetone specific production rate (g 1,2-propanediol + hydroxyacetone/g biomass/h) | 0.04 | 0.08 (+100%) |

TABLE 2

Comparison of the best evolved clone obtained after 132 days of evolution under microaerobic conditions with the initial strain

| Strain *E. coli* MG1655 lpd* ΔtpiA ΔpflAB ΔadhE ΔldhA::Cm ΔgloA Δald, ΔaldB, Δedd, ΔarcA Δndh (Strain 2) | Initial strain before evolution (performances measured after 2 days of culture) | Best evolved clone (performances measured after 2 days of culture) |
|---|---|---|
| Glucose specific consumption rate (g glucose/g biomass/h) | 0.15 | 0.28 (+87%) |
| 1,2-propanediol specific production rate (g 1,2-propanediol/g biomass/h) | 0.00 | 0.10 |
| 1,2-propanediol + hydroxyacetone specific production rate (g 1,2-propanediol + hydroxyacetone/g biomass/h) | 0.04 | 0.10 (+150%) |

Specific genes involved in the terminal 1,2-propanediol biosynthetic pathway were sequenced in the 2 best evolved clones of strain 1 and strain 2. For each clone, one mutated yqhD gene was identified resulting in expression of mutated YqhD protein: YqhD*(G149E) for evolved clone of strain 1 and YqhD*(G149S)(A286T) for evolved clone of strain 2.

Example 2

Production and Purification of Native YqhD and 3 Mutant YqhD (G149E, G149S and G149S A286T)

1. Construction of the Strains for Production of YqhD Proteins 1.1. Construction of the Plasmid for the Overexpression of Native yqhD: pTRC99A-yqhD The gene yqhD (sequence 3153377 to 3154540) was PCR amplified from genomic DNA of *E. coli* MG1655 using the following oligonucleotides:

```
yqhD F ptrc99A F, consisting of 43 pb
(SEQ ID NO 4):
cgatgcacgtcatgaacaactttaatctgcacacccaacccg,
``` with:—a region (underlined letters) homologous to the sequence (3153377 to 3153408) of the gene yqhD.

a BspHI restriction site (bold)

```
yqhD F ptrc99A R, consisting of 43 pb (SEQ ID NO 5):
ggcgtaaaaagcttagcgggcggctcgtatatacggcggctgacatccaacgtaatgtcgtgattttcg
``` with:—a region (underlined letters) homologous to the sequence (3154540 to 3154483) of the gene yqhD.

a HindIII restriction site (bold)

The PCR fragment amplified was digested by BspHI-HindIII and ligated in the pTRC99A digestion by NcoI-HindIII. The plasmid obtained was named pTRC99A-yqhD.

1.2. Construction of the Plasmids for the Overexpression of yqhD*

The three mutant YqhD bear the mutation (G149E), (G149S) or (G149S)(A286T). The plasmids for the overexpression of the three mutant proteins were built by site-directed mutagenesis using Quickchange site-directed mutagenesis kit from Stratagene® and the oligonucleotides described in table 3. The double mutant YqhD was built by two successive site-directed mutagenesis, G149S and then A286T.

The plasmids obtained were named pTRC99A-yqhD*(G149E), pTRC99A-yqhD*(G149S), pTRC99A-yqhD*(G149S)(A286T).

TABLE 3

Oligonucleotides used for the site-directed mutagenesis of yqhD

| Mutation | Name of oligonucleotides | Sequence of the oliognucleotide | Modification to create mutation | Homologous to the sequence |
|---|---|---|---|---|
| G149E | yqhD* (G149E) EcoRVF | ggttcagaatccaacgcagAAgcgg tgatAtcccgtaaaacc (SEQ ID NO 6) | Red capital letter: AA instead of GC to create mutation G149E. Green capital letter: A instead of C to create EcoRV restriction site without change in protein sequence | 3153803 to 3153844 |
| | yqhD* (G149E) EcoRVR | ggttttacgggaTatcaccgcTTctg cgttggattctgaacc (SEQ ID NO 7) | Red capital letter: TT instead of CG to create mutation G149E. Green capital letter: T instead of G to create EcoRV restriction site without change in protein sequence | |
| G149S | yqhD G149S MD F | ggttcagaatccaacgcaAgcgcggt gatAtcccgtaaaaccacaggc (SEQ ID NO 8) | Red capital letter: A instead of G to create mutation G149S. Green capital letter: A instead of C to create EcoRV restriction site without change in protein sequence | 3153803 to 3153850 |
| | yqhD G149S MD R | gcctgtggttttacgggaTatcaccgc gcTtgcgttggattctgaacc (SEQ ID NO 9) | Red capital letter: T instead of C to create mutation G149S. Green capital letter: T instead of G to create EcoRV restriction site without change in protein sequence | |
| A286T | yqhD A286T MD R | gatcacgcgcaaacactgActatAgt Actgcctgcactgtggaatgaaaaac gcg (SEQ ID NO 10) | Red capital letter: A instead of G to create mutation A286T. Green capital letter : A instead of C to create ScaI restriction site without change in protein sequence | 3154214 to 3154268 |
| | yqhD A286T MD scaI F | cgcgttttcattccacagtgcaggcag TacTatagTcagtgtttgcgcgtgatc (SEQ ID NO 11) | Red capital letter: T instead of C to create mutation A286T. Green capital letter : T instead of G to create ScaI restriction site without change in protein sequence | |

1.3. Construction of the Strain MG1655 ΔyqhD::Km

The gene yqhD was inactivated in strain *E. coli* MG1655 by inserting a Kanamycin resistance cassette and deleting most of the gene concerned using the technique described in Protocol 1.

Protocol 1: Introduction of a PCR Product for Recombination and Selection of the Recombinants (FRT System).

The oligonucleotides chosen and given in Table 4 for replacement of a gene or an intergenic region were used to amplify either the chloramphenicol resistance cassette from the plasmid pKD3 or the kanamycin resistance cassette from the plasmid pKD4 (Datsenko, K. A. & Wanner, B. L. (2000)). The PCR product obtained was then introduced by electroporation into the recipient strain bearing the plasmid pKD46 in which the system λ Red (γ, β, exo) expressed greatly favours homologous recombination. The antibiotic-resistant transformants were then selected and the insertion of the resistance cassette was checked by PCR analysis with the appropriate oligonucleotides given in Table 5.

If they are other modifications in the strain, they were checked with the oligonucleotides given in Table 5.

The resulting strain was named *E. coli* MG1655 ΔyqhD:: Km.

TABLE 4

Oligonucleotides used for replacement of a chromosomal region by recombination with a PCR product

| Region name | Names of oligos | Homology with chromosomal region |
|---|---|---|
| gldA | DgldA F | 4137058 to 4136979 |
| | DgldA R | 4135955 to 4136034 |
| edd-eda | DedaR | 1930144 to 1930223 |
| | DeddF | 1932501 to 1932582 |
| aldA | DaldAR | 1487615 to 1487695 |
| | DaldAF | 1486256 to 1486336 |
| aldB | DaldBR | 3754534 to 3754455 |
| | DaldBF | 3752996 to 3753075 |
| arcA | DarcAF | 4637868 to 4637791 |
| | DarcAR | 4637167 to 4637245 |
| ndh | DndhF | 1165071 to 1165149 |
| | DndhR | 1166607 to 1166528 |
| Ptrc01-gapA | Ptrc-gapAF | 1860800 to 1860762 |
| | Ptrc-gapAR | 1860478 to 1860536 |
| gloA | DgloA F | 1725861 to 1725940 |
| | DgloA R | 1726268 to 1726189 |
| yqhD | DyqhDF | 3153377 to 3153456 |
| | DyqhDR | 3154540 to 3154460 |

TABLE 5

Oligonucleotides used for checking the insertion of resistance cassette or the loss of resistance cassette

| Region name | Names of oligos | Homology with chromosomal region |
|---|---|---|
| gldA gene | talC F | 4137144 to 4137121 |
|  | yijF R | 4135136 to 4135159 |
| edd-eda genes | edaR | 1929754 to 1929777 |
|  | eddF | 1932996 to 1932968 |
| aldA gene | aldAF | 1485877 to 1485901 |
|  | aldAR | 1487714 to 1487689 |
| aldB gene | aldBF | 3752056 to 3752095 |
|  | aldBR | 3754644 to 3754674 |
| arcA gene | arcAF | 4638292 to 4638273 |
|  | arcAR | 4636854 to 4636874 |
| ndh gene | ndhF | 1164722 to 164742 |
|  | ndhR | 1167197 to 1167177 |
| Ptrc01-gapA | yeaAF | 1860259 to 1860287 |
|  | gapAR | 1861068 to 1861040 |
| gloA | gloAF2 | 1725641 to 1725660 |
|  | gloAR2 | 1726450 to 1726431 |
| yqhD | yqhDF | 3153068 to 3153100 |
|  | yqhDR | 3154825 to 3154797 |
| mgsA::Km | helDF | 1025242 to 1025260 |
|  | mgsA R3 | 1026734 to 1026715 |

1.4. Introduction of the Plasmids Built in the Strain *E. coli* MG1655 ΔyqhD::Km.

The plasmids pTRC99A-yqhD, pTRC99A-yqhD*(G149E), pTRC99A-yqhD*(G149S), pTRC99A-yqhD*(G149S)(A286T) were transformed by electroporation in the strain *E. coli* MG1655 ΔyqhD::Km. The strains obtained were named respectively:

*E. coli* MG1655 ΔyqhD::Km pTRC99A-yqhD
*E. coli* MG1655 ΔyqhD::Km pTRC99A-yqhD*(G149E)
*E. coli* MG1655 ΔyqhD::Km pTRC99A-yqhD*(G149S)
*E. coli* MG1655 ΔyqhD::Km pTRC99A-yqhD*(G149S)(A286T).

2. Production of YqhD Proteins

The four strains previously described were cultivated at 37° C. under aerobic conditions in 2 l baffled Erlenmeyer flasks with 500 ml LB medium with 2.5 g/l glucose. The flasks were agitated at 200 rpm on an orbital shaker. When the optical density measured at 550 nm reached 0.5 units, the flasks were incubated at 25° C. When the optical density reached 1.2 units, the production of YqhD proteins was induced by adding 500 μM IPTG in the cultures. The biomass was harvested by centrifugation when the cultures reached an optical density above 3.5 units. The supernatant was discarded and the pellet was stored at −20° C. before use.

3. Methylglyoxal Reductase Activity Assay

Methylglyoxal reductase activity was assayed by measuring the initial rate of NADPH oxidation with a spectrophotometer at a wavelength of 340 nm and at a constant temperature of 37° C. The reaction mixture using methylglyoxal as substrate was carried out in 20 mM Hepes pH 7.5, 0.1 mM Zinc sulphate, 0.2 mM NADPH, 0.6 μg of purified enzyme in a final volume of 1 ml. The reaction mixture was incubated for 5 min at 37° C. and then the reaction was initiated by the addition of the substrate methylglyoxal at a final concentration of 10 mM. Control assay (blank), lacking the substrate was run in parallel and the value measured for the control was subtracted to the value measured for the assay to take into account non-specific oxidation of NADPH.

One unit of enzyme activity was defined as the amount of enzyme that consumed 1 μmol substrate per minute under the conditions of the assay. Specific enzyme activity was expressed as units per mg of protein.

4. Purification of the YqhD Enzymes 4.1. Step 1: Preparation of Cell-Free Extracts Between 350-400 mg of *E. coli* biomass were resuspended in 70 ml of 50 mM Hepes pH 7.5, and a protease inhibitor cocktail. Cells were sonicated on ice (Branson sonifier, 70 W) in a Rosett cell RZ3 during six cycles of 30 sec with 30 sec intervals. After sonication, cells were incubated for 1 hour at room temperature with 1 mM MgCl2 and 1 UI/ml of DNaseI. Cells debris were removed by centrifugation at 12000 g for 30 min at 4° C. Supernatant was kept as the crude extract.

4.2. Step 2: Ammonium Sulphate Precipitation

The crude extract was precipitated at a concentration of 50% ammonium sulphate: solid ammonium sulphate (300 g/l) was added to the crude extract on ice. After 15 min of incubation at 4° C., the mix was centrifuged at 12000 g for 15 min at 4° C. The supernatant was discarded and the precipitate dissolved in 40 ml of 50 mM Hepes pH 7.5, 1 M ammonium sulphate.

4.3. Step 3: Hydrophobic Chromatography.

Using an Akta Purifier (GE Healthcare), the protein extract from the previous step was loaded onto a 5 ml HiTrap PhenylHP column (GE Healthcare) equilibrated with the same buffer. The column was washed with 10 column volumes of the same buffer. Proteins were eluted with two steps gradient, a gradient of 10 column volumes from 1 M to 0.5 M ammonium sulphate and a gradient of 20 column volumes from 0.5 M to 0 M ammonium sulphate. After elution, the column was washed with 10 column volumes of 50 mM Hepes pH 7.5. The flow rate of the column was 2.5 ml/min and 2.5 ml fractions were collected. The fractions which contain the protein were pooled and concentrated to be loaded on a gel filtration column.

4.4. Step 4: Gel Filtration

The concentrated fractions from the HiTrap PhenylHP column were loaded onto a Superdex 200 10/300 GL column (GE Healthcare) equilibrated with 50 mM Hepes pH 7.5. The flow rate of the column was 0.5 ml/min and 0.5 ml fractions were collected. The protein was eluted with about 13.8 ml of buffer. The expression and purification of the three mutant yqhD was remarkably similar to that of the wild type enzyme. There were no differences in the oligomerisation state between the native yqhD and the mutated yqhD*. All proteins were stored at −20° C.

The pool of each purification step was analysed on a SDS 4-15% gradient polyacrylamide gel (FIG. 3). This gel showed that the purity increased along the purification step. After the superdex 200 column, the protein was almost 90% pure. The final pool showed one major band at about 42 kDa corresponding to the protein yqhD.

Example 3

Characterization of Native YqhD and 3 Mutant YqhD (G149E, G149S and G149S A286T) with the Substrate Methylglyoxal and with the Co-Factor NADPH

1. Characterization of the YqhD Enzymes with the Substrate Methylglyoxal

Kinetic constants (Km, kcat and kcat/Km) for the four purified enzymes (yqhD, yqhD*(G149E), yqhD*(G149S) and yqhD*(G149S A286T)) toward methylglyoxal were determined using the activity assay previously described. In this case the reaction was started by addition of the purified enzyme. Seven methylglyoxal concentrations between 1.3 mM and 30 mM were analysed for each enzyme. For all kinetics, initial velocity was determined in triplicate for all substrate concentrations.

Kinetic constants (Km and Vmax) of each protein were determined with the module enzyme kinetics from the software Sigma Plot (Systat Software Inc, San Jose, Calif.). The data sets exhibiting Michaelis-Menten kinetics were fitted to a Michaelis-Menten equation. The different kinetic parameters of four YqhD enzymes were compiled in Table 6.

TABLE 6 kinetics parameters for the YqhD enzymes toward methylglyoxal

|  | YqhD | YqhD*(G149S A286T) | YqhD* (G149S) | YqhD* (G149E) |
|---|---|---|---|---|
| Km (mM) | 4.81 ± 0.41 | 3.28 ± 0.38 | 3.37 ± 0.34 | 7.80 ± 0.79 |
| Specific activity (μmol/min/mg) | 3.91 ± 0.11 | 2.69 ± 0.10 | 3.80 ± 0.12 | 7.65 ± 0.31 |
| kcat (s−1) | 2.74 ± 0.08 | 1.89 ± 0.07 | 2.67 ± 0.09 | 5.38 ± 0.21 |
| kcat/Km (M−1s−1) | 570 ± 65 | 577 ± 88 | 792 ± 105 | 689 ± 98 |

The kinetics parameters of the four enzymes were very similar. The kinetic parameters, substrate affinity (Km), catalytic (kcat), and catalytic efficiency (kcat/Km) of the proteins yqhD*(G149S A286T)), yqhD*(G149S), were identical to the native protein.

Specific activity for each YqhD is directly calculated from the kcat value. Specific activity of YqhD and YqhD*(G149S) were similar. Specific activity of YqhD*(G149S)(A286T) represented 69% of the specific activity of YqhD. Specific activity of YqhD*(G149E) was almost doubled compared to that of YqhD. The mutations were not detrimental for the activity of the enzyme.

2. Characterization of the YqhD Enzymes with the co-Factor NADPH

Kinetic constants (Km, kcat and kcat/Km) for the four purified enzymes (yqhD, yqhD*(G149E), yqhD*(G149S) and yqhD*(G149S A286T)) toward methylglyoxal were determined using the activity assay previously described. In this case the reaction was started by addition of the purified enzyme. Nine NADPH concentrations between 6 μM and 300 μM were analysed for each enzyme. For all kinetics, initial velocity was determined in triplicate for all co-factor concentrations.

Kinetic constants (Km and Vmax) of each protein were determined with the module enzyme kinetics from the software Sigma Plot (Systat Software Inc, San Jose, Calif.). The data sets exhibiting Michaelis-Menten kinetics were fitted to a Michaelis-Menten equation. The different kinetic parameters of four YqhD enzymes were compiled in Table 7.

TABLE 7 kinetics parameters for the YqhD enzymes toward NADPH

|  | YqhD | YqhD*G149E | YqhD*(G149S A286T) | YqhD*G149S |
|---|---|---|---|---|
| Km (μM) | 32 ± 4.2 | 28 ± 1.8 | 20 ± 2.2 | 22 ± 3.7 |
| Specific activity (μmol/min/mg) | 2.99 ± 0.1 | 4.86 ± 0.08 | 3.17 ± 0.02 | 3.78 ± 0.15 |
| kcat (s−1) | 2.1 ± 0.1 | 3.4 ± 0.1 | 2.2 ± 0.1 | 2.7 ± 0.1 |
| kcat/Km (M−1s−1) | 6.6E+04 ± 1.1E+04 | 1.22E+05 ± 9.8E+03 | 1.13E+05 ± 1.3E+04 | 1.22E+05 ± 2.5E+04 |

The kinetic parameters, substrate affinity (Km) and catalytic constant (kcat) were similar for the native enzyme ant the three mutants. The catalytic efficiency (kcat/Km) of the three mutant proteins was around $1.22 \text{ E+05 M}^{-1} \text{ s}^{-1}$, but two times higher than the native enzyme (kcat/Km $6.6 \text{ E+04 M}^{-1} \text{ s}^{-1}$).

To summarize, the properties of the 3 mutant YqhD were very similar: the mutant YqhD have a better catalytic efficiency toward NADPH, allowing a more efficient use of this co-factor.

3. Characterization of the Inhibition of YqhD Enzymes by NADP+

The NADP+ inhibition constant for three purified enzymes (yqhD, yqhD*(G149E) and yqhD*(G149S A286T)) were determined in the conditions described for the activity assay, excepted for the concentration of methylglyoxal that was increased to 20 mM. Enzyme kinetics with regards to NADPH were realised with increasing concentration of NADPH between 50 and 200 μM. Five concentrations of the inhibitor NADP+ were used (0-0.05-0.1-0.2-0.5 mM) and the kinetics were recorded for each condition of inhibition. The NADP+ inhibition constant (Ki) of each protein was determined with the module enzyme kinetic from the software Sigma Plot (Systat Software Inc, San Jose, Calif.). A model of competitive inhibition was fitted by the software. The kinetic parameters calculated for these three proteins were summarized in Table 8.

TABLE 8

Inhibition of the YqhD enzymes by NADP+

| | YqhD | YqhD*G149E | YqhD*(G149S A286T) |
|---|---|---|---|
| Km (µM) | 51 ± 11 | 24 ± 5.5 | 19 ± 3.5 |
| Specific activity (µmol/min/mg) | 3.63 ± 0.284 | 5.53 ± 0.292 | 5.25 ± 0.183 |
| kcat (s−1) | 2.5 ± 0.2 | 3.9 ± 0.2 | 3.7 ± 0.13 |
| kcat/Km (M−1s−1) | 4.99E+04 ± 1.5E+04 | 1.62E+05 ± 4.5E+04 | 1.94E+05 ± 4.25E+04 |
| Ki NADP+ (µM) | 68 ± 11 | 28 ± 5 | 16 ± 2.5 |

The native YqhD enzyme was highly inhibited by the inhibitor NADP+ (Ki=68 µM). However, the two mutant YqhD enzymes were even more sensitive to the inhibition by NADP+ (Ki lowered by a factor of 2 or 3).

Example 4

Construction of Two E. coli 1,2-Propanediol Producer Strains Expressing Wildtype or Modified YqhD and Assessment of 1,2-Propanediol Production 1. Construction of the Modified Strain E. coli MG1655 mgsA*(H21Q)::Km, Δedd-eda, ΔgloA, ΔaldA, ΔaldB, ΔarcA, Δndh (pME101-VB01-yqhD-gldA*(160T).

1.1. Construction of a Modified Strain E. coli ΔgloA::Cm

The gene gloA was inactivated in strain E. coli MG1655 by inserting a chloramphenicol antibiotic cassette and deleting most of the gene concerned using the technique described in protocol 1 with the oligonucleotides given in Table 4. The deletion was checked by a PCR analysis with the appropriate oligonucleotides given in Table 5. The resulting strain was named E. coli MG1655 ΔgloA::Cm.

1.2. Construction of a Modified Strain E. coli ΔgloA::Cm Δedd-eda::Km 1.2.1. Construction of a Modified Strain E. coli Δedd-eda::Km The genes edd-eda were inactivated in strain E. coli MG1655 by inserting a kanamycin antibiotic cassette and deleting most of the gene concerned using the technique described in Protocol 1 with the oligonucleotides given in Table 4. The deletion was checked by a PCR analysis with the appropriate oligonucleotides given in Table 5.

The resulting strain was named E. coli MG1655 Δedd-eda::Km.

1.2.2. Construction of a Modified Strain E. coli ΔgloA::Cm, Δedd-eda::Km.

The deletion of the genes edd-eda by replacement of the genes by a kanamycin resistance cassette in the strain E. coli Δedd-eda::Km was performed by the technique of transduction with phage P1 according to Protocol 2.

Protocol 2: Transduction with Phage P1 for Deletion of a Gene

The deletion of the chosen gene by replacement of the gene by a resistance cassette (kanamycin or chloramphenicol) in the recipient E. coli strain was performed by the technique of transduction with phage P1. The protocol was in two steps, (i) the preparation of the phage lysate on the strain MG1655 with a single gene deleted and (ii) the transduction of the recipient strain by this phage lysate.

Preparation of the Phage Lysate

Seeding with 100 µl of an overnight culture of the strain MG1655 with a single gene deleted of 10 ml of LB+Cm 30 µg/ml+glucose 0.2%+CaCl₂ 5 mM.

Incubation for 30 min at 37° C. with shaking.

Addition of 100 µl of phage lysate P1 prepared on the wild type strain MG1655 (approx. 1×10⁹ phage/ml).

Shaking at 37° C. for 3 hours until all cells were lysed.

Addition of 200 µl of chloroform, and vortexing.

Centrifugation for 10 min at 4500 g to eliminate cell debris.

Transfer of supernatant in a sterile tube and addition of 200 µl of chloroform.

Storage of the lysate at 4° C.

Transduction

Centrifugation for 10 min at 1500 g of 5 ml of an overnight culture of the E. coli recipient strain in LB medium.

Suspension of the cell pellet in 2.5 ml of MgSO₄ 10 mM, CaCl₂ 5 mM.

Control tubes: 100 µl cells

100 µl phages P1 of the strain MG1655 with a single gene deleted.

Tube test: 100 µl of cells+100 µl phages P1 of strain MG1655 with a single gene deleted.

Incubation for 30 min at 30° C. without shaking.

Addition of 100 µl sodium citrate 1 M in each tube, and vortexing.

Addition of 1 ml of LB.

Incubation for 1 hour at 37° C. with shaking

Plating on dishes LB+Cm 30 µg/ml after centrifugation of tubes for 3 min at 7000 rpm.

Incubation at 37° C. overnight.

The antibiotic-resistant transformants were then selected and the insertion of the deletion was checked by a PCR analysis with the appropriate oligonucleotides given in Table 5.

The deletion was checked by a PCR analysis with the appropriate oligonucleotides given in Table 5 as well as the other deletion already present in the strain.

The resulting strain was named E. coli ΔgloA::Cm, Δedd-eda::Km.

1.3. Construction of a Modified Strain E. coli MG1655 Δedd-eda ΔgloA

The antibiotic resistance cassette were eliminated in the strain E. coli Δedd-eda::Km, ΔgloA::Cm according to Protocol 3.

Protocol 3: Elimination of Resistance Cassettes (FRT System)

The chloramphenicol and/or kanamycin resistance cassettes were eliminated according to the following technique. The plasmid pCP20 carrying the gene coding for FLP recombinase acting at the FRT sites of the chloramphenicol and/or kanamycin resistance cassettes was introduced into the strain by electroporation. After serial culture at 42° C., the loss of the antibiotic resistance cassettes was checked by PCR analysis with the oligonucleotides given in Table 5.

The presence of the modifications previously built in the strain was checked using the oligonucleotides given in Table 5.

The strain obtained was named *E. coli* MG1655 Δedd-eda ΔgloA.

1.4. Construction of the Modified Strain *E. coli* MG1655 Δedd-eda ΔgloA, ΔaldA::Cm 1.4.1. Construction of the Modified Strain *E. coli* MG1655 ΔaldA::Cm The genes aldA was inactivated in strain *E. coli* MG1655 by inserting a chloramphenicol antibiotic cassette and deleting most of the gene concerned using the technique described in protocol 1 with the oligonucleotides given in Table 4. The deletion was checked by a PCR analysis with the appropriate oligonucleotides given in Table 5.

The resulting strain was named *E. coli* MG1655 ΔaldA::Cm.

1.4.2. Construction of the Modified Strain *E. coli* MG1655 Δedd-eda ΔgloA, ΔaldA::Cm The deletion of the gene aldA by replacement of the gene by a chloramphenicol resistance cassette in the strain *E. coli* MG1655 Δedd-eda ΔgloA was performed by the technique of transduction with phage P1 (Protocol 2).

The deletion ΔaldA::Cm and the others modifications were checked using the oligonucleotides described in table 5.

The resulting strain was named *E. coli* ΔgloA::Cm, Δedd-eda::Km, ΔaldA::Cm 1.5. Construction of the Modified Strain *E. coli* MG1655 Δedd-eda, ΔgloA, ΔaldA::Cm, ΔaldB::Km 1.5.1. Construction of the Modified Strain *E. coli* MG1655 ΔaldB::Km The genes aldB was inactivated in strain *E. coli* MG1655 by inserting a Kanamycin antibiotic cassette and deleting most of the gene concerned using the technique described in protocol 1 with the oligonucleotides given in Table 4. The deletion was checked by a PCR analysis with the appropriate oligonucleotides given in Table 5.

The resulting strain is named *E. coli* MG1655 ΔaldB::Km.

1.5.2. Construction of the Modified Strain *E. coli* MG1655 Δedd-eda ΔgloA, ΔaldA::Cm, ΔaldB::Km The deletion of the gene aldA by replacement of the gene by a Kanamycin resistance cassette in the strain *E. coli* MG1655 Δedd-eda ΔgloA, ΔaldA::Cm, was performed by the technique of transduction with phage P1 (Protocol 2).

The deletion ΔaldB::Km and the others modifications were checked using the oligonucleotides described in Table 5.

The resulting strain was named *E. coli* ΔgloA, Δedd-eda, ΔaldA::Cm, ΔaldB::Km.

1.6. Construction of the Modified Strain *E. coli* MG1655 Δedd-eda ΔgloA, ΔaldA, ΔaldB The antibiotic resistance cassette was eliminated in the strain *E. coli* MG1655 Δedd-eda ΔgloA, ΔaldA::Cm, ΔaldB::Km according to Protocol 3.

The loss of the antibiotic resistance cassettes was checked by PCR analysis with the oligonucleotides given in Table 5. The presence of the modifications previously built in the strain was also checked using the oligonucleotides given in Table 5.

The strain obtained was named *E. coli* MG1655 Δedd-eda ΔgloA, ΔaldA, ΔaldB.

1.7. Construction of the Modified Strain *E. coli* MG1655 Δedd-eda ΔgloA, ΔaldA, ΔaldB, ΔarcA::Km 1.7.1. Construction of the Modified Strain *E. coli* MG1655 ΔarcA::Km The genes arcA was inactivated in strain *E. coli* MG1655 by inserting a Kanamycin antibiotic cassette and deleting most of the gene concerned using the technique described in Protocol 1 with the oligonucleotides given in Table 4. The deletion was checked by a PCR analysis with the appropriate oligonucleotides given in Table 5.

The resulting strain was named *E. coli* MG1655 ΔarcA::Km.

1.7.2. Construction of the Modified Strain *E. coli* MG1655 Δedd-eda ΔgloA, ΔaldA, ΔaldB, ΔarcA::Km The deletion of the gene arcA by replacement of the gene by a Kanamycin resistance cassette in the strain *E. coli* Δedd-eda ΔgloA, ΔaldA, ΔaldB, ΔarcA::Km, was performed by the technique of transduction with phage P1 (Protocol 2)

The deletion ΔarcA::Km and the others modifications were checked using the oligonucleotides described in Table 5.

The resulting strain was named *E. coli* MG1655 Δedd-eda ΔgloA, ΔaldA, ΔaldB, ΔarcA::Km.

1.8. Construction of the Modified Strain *E. coli* MG1655 Δedd-eda ΔgloA, ΔaldA, ΔaldB, ΔarcA::Km, Δndh::Cm 1.8.1. Construction of the Modified Strain *E. coli* MG1655 Δndh::Cm The gene ndh was inactivated in strain *E. coli* MG1655 by inserting a chloramphenicol resistance cassette and deleting most of the gene concerned using the technique described in Protocol 1 with the oligonucleotides given in Table 4. The deletion was checked by a PCR analysis with the appropriate oligonucleotides given in Table 5.

The resulting strain was named *E. coli* MG1655 Δndh::Cm.

1.8.2. Construction of the Modified Strain *E. coli* MG1655 Δedd-eda ΔgloA, ΔaldA, ΔaldB, ΔarcA::Km, Δndh::Cm The deletion of the gene ndh by replacement of the gene by a chloramphenicol resistance cassette in the strain *E. coli* Δedd-eda ΔgloA, ΔaldA, ΔaldB, ΔarcA::Km, was performed by the technique of transduction with phage P1 (Protocol 2).

The deletion Δndh::Cm and the others modifications were checked using the oligonucleotides described in Table 5.

The resulting strain was named *E. coli* MG1655 Δedd-eda ΔgloA, ΔaldA, ΔaldB, ΔarcA::Km, Δndh::Cm.

1.9. Construction of the Modified Strain *E. coli* MG1655 Δedd-eda, ΔgloA, ΔaldA, ΔaldB, ΔarcA, Δndh The antibiotic resistance cassette was eliminated in the strain *E. coli* MG1655 Δedd-eda ΔgloA, ΔaldA, ΔaldB, ΔarcA::Km, Δndh::Cm according to Protocol 3.

The loss of the antibiotic resistance cassettes was checked by PCR analysis with the oligonucleotides given in Table 4. The presence of the modifications previously built in the strain was also checked using the oligonucleotides given in Table 5.

The strain obtained was named *E. coli* MG1655 Δedd-eda ΔgloA, ΔaldA, ΔaldB, ΔarcA, Δndh.

1.10. Construction of the Modified Strain *E. coli* MG1655 Δedd-eda, ΔgloA, ΔaldA, ΔaldB, ΔarcA, Δndh (pME101VB01-yqhD-gldA*(A160T))

1.10.1. Construction of the Plasmid pME101-VB01-yqhD-gldA*(A160T)

1.10.1.1. Construction of the Plasmid pME101-VB01

The plasmid pME101VB01 was derived from plasmid pME101 and harbors a multiple cloning site containing recognition site sequences specific for the rare restriction endonucleases NheI, SnaBI, PacI, BglII, AvrII, SacII and AgeI following by the adc transcription terminator of *Clostridium acetobutylicum* ATCC824.

For the expression from a low copy vector the plasmid pME101 was constructed as follows. The plasmid pCL1920 (Lerner & Inouye, 1990, NAR 18, 15 p 4631-GenBank AX085428) was PCR amplified using the oligonucleotides PME101F and PME101R and the BstZ17I-XmnI fragment from the vector pTrc99A (Amersham Pharmacia Biotech, Piscataway, N.J.) harboring the lacI gene and the trc promoter was inserted into the amplified vector.

```
PME101F (SEQ ID NO 12): ccgacagtaagacgggtaagcctg

PME101R (SEQ ID NO 13): agcttagtaaagccctcgctag
```

A synthetic double-stranded nucleic acid linker comprising the multicloning site and adc transcriptional terminator was used to generate pME101VB01. Two 100 bases oligonucleotides that complement flanked by NcoI or HindIII digested restriction sites were annealed. The 100-base pair product was subcloned into NcoI/HindIII digested plasmid pME101 to generate pME101VB01.

```
pME101VB01 1, consisting of 100 bases
(SEQ ID NO 14):
catgggctagctacgtattaattaaagatctcctagggagctcaccggt TAAAAATAAGAGTTACCTTAAATGGTAACTCTTATTTTTTAggcgcgc ca pME101VB01 2, consisting of 100 bases
(SEQ ID NO 15):
agcttggcgcgccTAAAAAAATAAGAGTTACCATTTAAGGTAACTCTTA TTTTTAaccggtgagctccctaggagatctttaattaatacgtagctag cc
``` with:
  a region (underlined lower-case letters) corresponding to the multicloning site
  a region (upper-case letters) corresponding to the adc transcription terminator (sequence 179847 to 179814) of *Clostridium acetobutylicum* ATCC 824 pSOL1 (NC_001988).

1.10.1.2. Construction of the Plasmid pME101-VB01-yqhD-gldA*(A160T)

1.10.1.2.1. Construction of the Plasmid pME101-VB01-yqhD

The gene yqhD was PCR amplified from genomic DNA of *E. coli* MG1655 using the following oligonucleotides

```
yqhD F, consisting of 43 pb, (SEQ ID NO 16)
cgatgcacgtcatgaacaactttaatctgcacacccaacccg
``` with:
  a region (underlined letter) homologous to the sequence (3153377 to 3153408) of the gene yqhD
  a restriction site BspHI (bold face letters)

```
yqhD R, consisting of 29 pb (SEQ ID NO 17)
Ctagctagcttagcgggcggcttcgtata
```

With:
  a region (underlined letter) homologous to the sequence (3154540 to 3154521) the gene yqhD
  a restriction site NheI (bold face letters)

The PCR amplified fragment was cut with the restriction enzymes BspHI and NheI and cloned into the NcoI/NheI sites of the vector pME101VB01. The resulting plasmid was named pME101VB01-yqhD 1.10.1.2.2. Construction of the Plasmid pSCB-gldA*(A160T)

The gene gldA, PCR amplified from genomic DNA of *E. coli* MG1655 using the oligonucleotides gldA F and gldA R was cloned in pSCB (Strataclone®). The resulted plasmid was named pSCB-gldA.

A directed mutagenesis was performed on this plasmid with the following oligonucleotide: gldA*A160TmutDirF (consisting of 45 pb, gacaccaaaatcgtcgctggcacacctgcacgtctgCtagcggcg, SEQ ID NO 18) and gldA*A160TmutDirR (consisting of 45 pb cgccgctaGcagacgtgcaggtgtgccagcgacgattttggtgtc, SEQ ID NO 19). The two oligonucleotides were homologous to the region 4136602 to 4136558. In bold face letter, bases which were changed to create the mutation A160T and underlined letter, the base which were change to create EcoRV restriction site. The resulted plasmid was named pSCB-gldA*(A 160T).

1.10.1.3. Construction of the pME101VB01-yqhD-gldA*(A160T)

The pSCB-gldA*(A160T) was cut with the restriction enzymes avrII and SacI and the fragment containing gldA*(A160T) was cloned into the avrII/SacI sites of the vector pME101VB01-yqhD. The resulted plasmid was named pME101VB01-yqhD-gldA*(A160T).

1.10.2. Construction of the Modified Strain *E. coli* MG1655 Δedd-eda, ΔgloA, ΔaldA, ΔaldB, ΔarcA, Δndh (pME101VB01-yqhD-gldA*(A160T))

The plasmid pME101VB01-yqhD-gldA*(A160T) was introduced by electroporation into the strain *E. coli* MG1655 Ptrc01-gapA::cm, Δedd-eda, ΔgloA, ΔaldA, ΔaldB, ΔarcA, Δndh.

The strain obtained was named *E. coli* MG1655 Δedd-eda, ΔgloA, ΔaldA, ΔaldB, ΔarcA, Δndh (pME101VB 01-yqhD-gldA*(A160T).

1.11. Construction of the Modified Strain *E. coli* MG1655 mgsA*(H21Q)::Km Δedd-eda, ΔgloA, ΔaldA, ΔaldB, ΔarcA, Δndh (pME101VB01-yqhD-gldA*(A160T))

1.11.1. Construction of the Modified Strain *E. coli* MG1655 mgsA*(H21Q)::Km 1.11.1.1. Construction of the Modified Strain *E. coli* MG1655 mgsA*(H21Q)

A mutation was introduced in the mgsA gene in order to obtain the mutant protein MgsA*(H21Q). The technique used to build this modification was described by Heermann et al. (2008), Microbial Cell Factories. 7(14): 1-8.

The following oligonucleotides were used to amplify the rpsL-Neo cassette:

```
1. mgsA*(H21Q)::rpsL-Neo F, consisting in 105 pb,
(SEQ ID NO 20)
gttaactacggatgtacattatggaactgacgactcgcactttacctgc gcggaaacatattgcgctggtggcacacgatcaggcctggtgatgatgg cgggatc
``` with,
  a region (underlined letter) homologous to the sequence of the gene mgsA.
  a region (bold face letter) to amplified rpsL-Neo cassette.

```
2. mgsA*(H21Q)::rpsL-Neo R (SEQ ID NO 21)
gggaaattaagttaccggtagtgcctgttgcatacagtacgtgttgttc cagtaacggttgatgccgttccacccagctcatcagcatctgtttgcat tcagaagaactcgtcaagaagg
``` with,
    a region (underlined letter) homologous to the sequence of the gene mgsA with to mutation, the first one (in red) to create the mutation H21Q and the second one (in yellow) to create the restriction site AlwN1.
    a region (bold face letter) to amplified rpsL-Neo cassette.

The fragment obtained was introduced into the strain MG1655 rpsL* (built as described in Heermann et al.) according to Protocol 1. The strain obtained was checked by PCR and sequence analysis. The strain obtained was named E. coli mgsA*(H21Q)::rpsL-Neo.

The deletion of the cassette rpsL-Neo was performed according to Protocol 1. The fragment transformed was obtained by the restriction with NcoI and SacI of the plasmid pETTOPO-mgsA*(H21Q).

The modification was checked by PCR using oligonucleotides described in Table 5.

The strain obtained was named strain E. coli MG1655 mgsA*(H21Q).

1.11.1.2. Construction of the Modified Strain E. coli MG1655 mgsA*(H21Q)::Km

A kanamycin resistance cassette was introduced in 3' of mgsA*(H21Q) open reading frame using the following primers:

```
mgsA::Km F consisting of 100 bp: (SEQ ID NO 22)
tccagtcgccgcatttcaacgacgcggtcgatattctgatccccgatta tcagcgttatctcgcggaccgtctgaagtaatgtaggctggagctgctt cg
``` with:
    a region (underlined letters) homologous to the end of mgsA*(H21Q) ORF,
    a region (Bold letter) to amplified Kanamycin cassette.

```
mgsA::Km R consisting of 100 bp: (SEQ ID NO 23)
Tgtggaaatactgaaaaatctggatgtgccggtggcgagaaaaccgtaa gaaacaggtggcgtttgccacctgtgcaatacatatgaatatcctcctt ag
``` a region (underlined letters) homologous to the end of helD ORF,
a region (Bold letter) to amplified Kanamycin cassette.

The fragment obtained was introduced into the strain MG1655 mgsA*(H21Q) according to Protocol 1. The strain obtained was checked by PCR. The strain obtained is named E. coli mgsA*(H21Q)::Km 1.11.2. Construction of the Modified Strain E. coliMG1655 mgsA*(H21Q)::Km Δedd-eda, ΔgloA, ΔaldA, ΔaldB, ΔarcA, Δndh (pME101VB01-yqhD-gldA*(A160T))

The replacement of the mgsA with the mgsA*(H21Q)::Km into the strain E. coli Δedd-eda ΔgloA, ΔaldA, ΔaldB, ΔarcA, Δndh (pME101VB01-yqhD-gldA*(A160T)) was performed by the technique of transduction with phage P1. IPTG was added to the culture to promote the expression of the genes borne on the plasmid.

The modifications mgsA*(H21Q)::Km and the others deletions were checked using the oligonucleotides described in Table 5.

The resulting strain was named E. coli MG1655 mgsA*(H21Q)::Km Δedd-eda, ΔgloA, ΔaldA, ΔaldB, ΔarcA, Δndh (pME101VB01-yqhD-gldA*(A160T))

2. Construction of the Modified Strain E. coli MG1655 mgsA*(H21Q)::Km, Ptrc01-gapA::cm, Δedd-eda, ΔgloA, ΔaldA, ΔaldB, ΔarcA, Δndh (pME101-VB01-yqhD*(G149E)-gldA*(A160T))

2.1. Construction of the Plasmid (pME101-VB01-yqhD*(G149E)-gldA*(A160T))

2.1.1. Construction of the Plasmid pSCB-yqhD*(G149E)

The gene yqhD, PCR amplified from genomic DNA of E. coli MG1655 using the oligonucleotides yqhD F and yqhD R was cloned in pSCB (Strataclone®). The resulted plasmid was named pSCB-yqhD. A directed mutagenesis was performed on this plasmid with the following oligonucleotides: yqhD*G149EmutDirF (consisting of 45 pb, ggttcagaatccaacgcagaagcggtgatAtcccgtaaaaccacaggc, SEQ ID NO 24) and yqhD*G149EmutDirR (consisting of 45 pb gcctgtggtttacgggaTatcaccgcttctgcgttggattctgaacc, SEQ ID NO 25). The two oligonucleotides are homologous to the region 3153803 to 3153850. In bold face letter, bases which were changed to create the mutation G149E and capital letter, the base which were changed to create EcoRV restriction site. The resulted plasmid was named pSCB-yqhD*(G149E).

2.1.2. Construction of the Plasmid (pME101VB01-yqhD*(G149E)-gldA*(A160T)

The pSCB-yqhD*(G149E) was cut with the restriction enzymes BspHI and NheI and the fragment containing yqhD*(G149E) was cloned into the NcoI/NheI sites of the vector pME101VB01. The resulting plasmid was named pME101VB01-yqhD*(G149E). The pSCB-gldA*(A160T) was cut with the restriction enzymes avrII and SacI and the fragment containing gldA*(A160T) was cloned into the avrII/SacI sites of the vector pME101VB01-yqhD*(G149E). The resulted plasmid was named pME101VB01-yqhD*(G149S)-gldA*(A160T).

2.2. Construction of the Modified Strain E. coli MG1655 Δedd-eda, ΔgloA, ΔaldA, ΔaldB, ΔarcA, Δndh (pME101-VB01-yqhD*(G149E)-gldA*(A160T))

The plasmid pME101-VB01-yqhD*(G149E)-gldA*(A160T) was introduced by electroporation into the strain E. coli MG1655 Δedd-eda, ΔgloA, ΔaldA, ΔaldB, ΔarcA, Δndh.

The strain obtained was named E. coli MG1655 Δedd-eda, ΔgloA, ΔaldA, ΔaldB, ΔarcA, Δndh (pME101-VB01-yqhD*(G149E)-gldA*(A160T))

2.3. Construction of the Modified Strain E. coli MG1655 mgsA*(H21Q)::Km, Δedd-eda, ΔgloA, ΔaldA, ΔaldB, ΔarcA, Δndh (pME101-VB01-yqhD*(G149E)-gldA*(A160T))

The replacement of the mgsA with the mgsA*(H21Q)::Km into the strain E. coli Δedd-eda ΔgloA, ΔaldA, ΔaldB, ΔarcA, Δndh (pME101VB01-yqhD*(G149E)-gldA*(A160T)) was performed by the technique of transduction with phage P1. IPTG was added to the culture to promote the expression of the genes borne on the plasmid.

The modifications mgsA*(H21Q)::Km and the others deletion were checked using the oligonucleotides described in Table 5.

The resulting strain was named E. coli MG1655 mgsA*(H21Q)::Km, Δedd-eda, ΔgloA, ΔaldA, ΔaldB, ΔarcA, Δndh (pME101-VB01-yqhD*(G149E)-gldA*(A160T).

3. Assessment of 1,2-Propanediol Production in Two E. coli Isogenic Strains Differing Only in the yqhD Alleles The two strains described above were cultivated in an Erlenmeyer flask assay (500 ml flasks with 50 ml of medium) under aerobic conditions in minimal medium MML11PG1_100 (see composition in Table 9) with 20 g/l glucose as sole carbon source. Spectinomycin was added at a concentration of 50 mg/l.

TABLE 9 composition of minimal medium MML11PG1_100.

| Constituent | Concentration (g/l) |
|---|---|
| EDTA | 0.0084 |
| $CoCl_2 \, 6H_2O$ | 0.0025 |
| $MnCl_2 \, 4H_2O$ | 0.0150 |
| $CuCl_2 \, 2H_2O$ | 0.0015 |
| $H_3BO_3$ | 0.0030 |
| $Na_2MoO_4 \, 2H_2O$ | 0.0025 |
| $Zn(CH_3COO)_2 \, 2H_2O$ | 0.0130 |
| Fe(III) citrate $H_2O$ | 0.1064 |
| Citric acid | 1.70 |
| $KH_2PO_4$ | 1.65 |
| $K_2HPO_4 \, 3H_2O$ | 0.92 |
| $(NH_4)_2HPO_4$ | 0.40 |
| $(NH_4)_2SO_4$ | 4.88 |
| $MgSO_4 \, 7H_2O$ | 1.00 |
| $CaCl_2 \, 2H_2O$ | 0.08 |
| Thiamine | 0.01 |
| Glucose or Sucrose | 20.00 |
| MOPS buffer | 40.00 |

The pH of the medium was adjusted to 6.8 with sodium hydroxide

The culture was carried out at 37° C. and the pH was maintained by buffering the culture medium with MOPS.

At the end of the culture, 1,2-propanediol and residual glucose in the fermentation broth were analysed by HPLC using a Biorad HPX 97H column for the separation and a refractometer for the detection. The biomass concentration was recorded as dry cell weight. The 1,2-propanediol specific productions were then calculated.

TABLE 10 production of 1,2-propanediol in minimal medium with glucose as carbon source.

| Strain/ | Carbon source | 1,2-propanediol titer (g/l) | 1,2-propanediol specific production (g/g biomass) |
|---|---|---|---|
| E. coli MG1655 mgsA*(H21Q)::Km ΔgloA Δedd-eda ΔaldA ΔaldB ΔarcA Δndh (pME101VB01-yqhD-gldA*(A160T)) | glucose | 0.813 +/− 0.033 (n = 3) | 0.569 +/− 0.015 (n = 3) |
| E. coli MG1655 mgsA*(H21Q)::Km ΔgloA Δedd-eda ΔaldA ΔaldB ΔarcA Δndh (pME101VB01-yqhD*(G149E)-gldA*(A160T)) | glucose | 0.904 +/− 0.049 (n = 3) | 0.613 +/− 0.017 (n = 3) | n is the number of repetitions of the same experiment - The figures given are the mean and standard deviation of the figures obtained for n repetitions.

The titer and the specific production of 1,2-propanediol in the E. coli strain with a mutant YqhD were improved as compared with the isogenic strain with a native YqhD.

The improved properties of the mutant YqhD enzyme shown in Example 3 will lead to a more significant improvement of the performances of the strain with a mutant YqhD over the isogenic strain when compared in fed-batch culture.

Example 5

Production of 1,2-Propanediol by E. coli with a Mutant MGS, a Mutant YqhD and a Mutant GlyDH on Glucose and Sucrose 1. Construction of the Modified Strain E. coli MG1655 mgsA*(H21Q), Δedd-eda, ΔgloA, ΔaldA, ΔaldB, ΔarcA, Δndh (pME101-VB01-yqhD*(G149E)-gldA*(A160T)))

The construction of this strain was described in example 4.

2. Construction of the Modified Strain E. coli MG1655 mgsA*(H21Q,) Δedd-eda, ΔgloA, ΔaldA, ΔaldB, ΔarcA, Δndh (pME101-VB01-yqhD*(G149E)-gldA*(A160T)) (pBBR1MCS5-cscBKAR)

2.1. Construction of the Plasmid pBBR1MCS5-cscBKAR

The plasmid pKJL101.1 (Jahreis et al. (2002), J. Bacteriol. 184:5307-5316) was digested by EcoRI. The fragment containing the cscBKAR gene was cloned in pBBR1MCS5 (Kovach et al. (1995), Gene, 166 175-176) also digested by EcoRI.

The plasmid obtained was named pBBR1MCS5-cscBKAR.

2.2. Construction of the Modified Strain E. coli MG1655 mgsA*(H21Q), Δedd-eda, ΔgloA, ΔaldA, ΔaldB, ΔarcA, Δndh (pME101-VB01-yqhD*(G149E)-gldA*(A160T)) (pBBR1MCS5-cscBKAR)

The plasmid pBBR1MCS5-cscBKAR was introduced by electroporation in the strain E. coli MG1655 mgsA*(H21Q), Δedd-eda, ΔgloA, ΔaldA, ΔaldB, ΔarcA, Δndh. pME101-VB01-yqhD*(G149E)-gldA*(A160T)).

The strain obtained was named strain E. coli MG1655 mgsA*(H21Q), Δedd-eda, ΔgloA, ΔaldA, ΔaldB, ΔarcA, Δndh (pME101-VB01-yqhD*(G149E)-gldA*(A160T)) (pBBR1MCS5-cscBKAR).

3. Assessment of 1,2-Propanediol Production in Two E. coli with a Mutant MGS, a Mutant YqhD and a Mutant GlyDH on Glucose and Sucrose The two strains described above were cultivated in an Erlenmeyer flask assay (500 ml flasks with 50 ml of medium) under aerobic conditions in minimal medium MML11PG1_ 100 (see composition in Table 9) with 20 g/l glucose or sucrose as sole carbon source. Spectinomycin was added at a concentration of 50 mg/l.

The culture was carried out at 37° C. and the pH was maintained by buffering the culture medium with MOPS.

At the end of the culture, 1,2-propanediol and residual glucose or sucrose in the fermentation broth were analysed by HPLC using a Biorad HPX 97H column for the separation and a refractometer for the detection. The yields of 1,2-propanediol over glucose or sucrose were then calculated.

TABLE 11 production of 1,2-propanediol in minimal medium with glucose or sucrose as carbon source.

| Strain | Carbon source | 1,2-propanediol titer (g/l) | 1,2-propanediol yield (g/g carbon source) |
|---|---|---|---|
| E. coli MG1655 mgsA*(H21Q)::Km ΔgloA Δedd-eda ΔaldA ΔaldB ΔarcA Δndh (pME101VB01-yqhD*(G149E)-gldA*(A160T)) | glucose | 0.904 +/− 0.049 (n = 3) | 0.133 +/− 0.009 (n = 3) |

TABLE 11-continued production of 1,2-propanediol in minimal medium with glucose or sucrose as carbon source.

| Strain | Carbon source | 1,2-propanediol titer (g/l) | 1,2-propanediol yield (g/g carbon source) |
|---|---|---|---|
| E. coli MG1655 mgsA*(H21Q)::Km ΔgloA Δedd-eda ΔaldA ΔaldB ΔarcA Δndh (pME101VB01-yqhD*(G149E)-gldA*(A160T)) (pBBR1MCS5-cscBKAR) | sucrose | 1.823 +/− 0.098 (n = 3) | 0.196 +/− 0.007 (n = 3) | n is the number of repetitions of the same experiment - The figures given are the mean and standard deviation of the figures obtained for n repetitions.

The production of 1,2-propanediol in a E. coli strain with a mutant YqhD was improved on sucrose as sole carbon source as compared with glucose.

Example 6

Construction of Two E. coli Acetol Producer Strains Expressing Wildtype or Modified YqhD and Assessment of Acetol Production 1. Construction of the Modified Strain E. coli MG1655 mgsA*(H21Q)::Km Ptrc01-gapA::cm, Δedd-eda, ΔgloA, ΔaldA, ΔaldB, ΔgldA, (pME101-VB01-yqhD)

1.1. Construction of the Modified Strain E. coli MG1655 Δedd-eda ΔgloA, ΔaldA, ΔaldB, ΔgldA 1.1.1. Construction of the Modified Strain ΔgldA::Km The gene gldA was inactivated in strain E. coli MG1655 by inserting a Kanamycin antibiotic cassette and deleting most of the gene concerned using the technique described in protocol 1 with the oligonucleotides given in Table 4. The deletion was checked by a PCR analysis with the appropriate oligonucleotides given in Table 5. The resulting strain was named E. coli MG1655 ΔgldA::Km.

1.1.2. Construction of the Modified Strain E. coli MG1655 Δedd-eda ΔgloA, ΔaldA, ΔaldB, ΔgldA::Km The deletion of the gene gldA by replacement of the gene by a Kanamycine resistance cassette in the strain E. coli MG1655 Δedd-eda ΔgloA, ΔaldA, ΔaldB, Δedd-eda, ΔgloA, ΔaldA, ΔaldB was performed by the technique of transduction with phage P1 (Protocol 2).

The deletion was checked by a PCR analysis with the appropriate oligonucleotides given in Table 5 as well as the others deletions already present in the strain.

The resulting strain was named E. coli MG1655 Δedd-eda ΔgloA, ΔaldA, ΔaldB, ΔgldA::Km 1.1.3. Construction of the Modified Strain E. coli MG1655 Δedd-eda ΔgloA, ΔaldA, ΔaldB, ΔgldA The antibiotic resistance cassette was eliminated in the strain E. coli MG1655 Δedd-eda ΔgloA, ΔaldA, ΔaldB, ΔgldA::Km according to Protocol 3.

The loss of the antibiotic resistance cassette was checked by PCR analysis with the oligonucleotides given in Table 5. The presence of the modifications previously built in the strain was also checked using the oligonucleotides given in Table 5.

The strain obtained was named E. coli MG1655 Δedd-eda ΔgloA, ΔaldA, ΔaldB, Δedd-eda, ΔgloA, ΔaldA, ΔaldB, ΔgldA.

1.2. Construction of the Modified Strain E. coli MG1655 Ptrc01-gapA::cm Δedd-eda ΔgloA, ΔaldA, ΔaldB, ΔgldA 1.2.1. Construction of the Modified Strain MG1655 Ptrc01-gapA::Cm The replacement of the natural gapA promoter with the synthetic short Ptrc01 promoter (SEQ ID NO 26: gagctgt-tgactattaatcatccggctcgaataatgtgtgg) into the strain E. coli MG1655 was made by replacing 225 pb of upstream gapA sequence with FRT-CmR-FRT and an engineered promoter using the technique described in Protocol 2 with the oligonucleotides given in Table 4.

The deletion was checked by a PCR analysis with the appropriate oligonucleotides given in Table 5. The resulting strain was named E. coli MG1655 Ptrc01-gapA::Cm.

1.2.2. Construction of the Modified Strain E. coli MG1655 Ptrc01-gapA:: cm Δedd-eda ΔgloA, ΔaldA, ΔaldB, ΔgldA The replacement of the natural gapA promoter with the synthetic short Ptrc01 promoter into the strain E. coli MG1655 Δedd-eda ΔgloA, ΔaldA, ΔaldB, Δedd-eda, ΔgloA, ΔaldA, ΔaldB, ΔgldA was performed by the technique of transduction with phage P1.

The modifications Ptrc01-gapA::cm and the others deletion were checked using the oligonucleotides described in Table 5.

The strain obtained was named E. coli MG1655 Ptrc01-gapA::cm Δedd-eda ΔgloA, ΔaldA, ΔaldB, ΔgldA.

1.3. Construction of the Modified Strain E. coli MG1655 Ptrc01-gapA::cm Δedd-eda ΔgloA, ΔaldA, ΔaldB, ΔgldA pME101-VB01-yqhD, The plasmids pME101VB01-yqhD (see Example 4) was introduced by electroporation into the strain E. coli MG1655 Ptrc01-gapA:: cm Δedd-eda ΔgloA, ΔaldA, ΔaldB, ΔgldA.

The strain obtained was named E. coli MG1655 Ptrc01-gapA::cm Δedd-eda ΔgloA, ΔaldA, ΔaldB, ΔgldA (pME101-VB01-yqhD).

1.4. Construction of the Modified Strain E. coli MG1655 mgsA*(H21Q)::Km Ptrc01-gapA::cm Δedd-eda ΔgloA, ΔaldA, ΔaldB, ΔgldA pME101-VB01-yqhD, The replacement of the mgsA with the mgsA*(H21Q)::Km into the strain E. coli Δedd-eda ΔgloA, ΔaldA, ΔgldA (pME101VB01-yqhD) was performed by the technique of transduction with phage P1. IPTG was added to the culture to promote the expression of the gene borne on the plasmid.

The modifications mgsA*(H21Q)::Km and the others deletion were checked using the oligonucleotides described in Table 5.

2. Construction of the Strain E. coli MG1655 Ptrc01-gapA:: cm Δedd-eda ΔgloA, ΔaldA, ΔaldB, Δedd-eda, ΔgloA, ΔaldA, ΔaldB, ΔgldA (pME101-VB01-yqhD*(6149E)

2.1. Construction of the Modified Strain E. coli MG1655 Ptrc01-gapA::cm Δedd-eda ΔgloA, ΔaldA, ΔaldB, ΔgldA pME101-VB01-yqhD*(G149E), The plasmid pME101-VB01-yqhD*(G149E) (see Example 4) was introduced by electroporation in the strain E. coli MG1655 Ptrc01-gapA::cm Δedd-eda ΔgloA, ΔaldA, ΔaldB, Δedd-eda, ΔgloA, ΔaldA, ΔaldB, ΔgldA.

The strain obtained was named E. coli MG1655 Ptrc01-gapA::cm Δedd-eda ΔgloA, ΔaldA, ΔaldB, Δedd-eda, ΔgloA, ΔaldA, ΔaldB, ΔgldA pME101-VB01-yqhD*(G149E).

2.2. Construction of the Modified Strain E. coli MG1655 mgsA*(H21Q)::Km Ptrc01-gapA::cm Δedd-eda ΔgloA, ΔaldA, ΔaldB, ΔgldA pME101-VB01-yqhD*(G149E), The replacement of the mgsA with the mgsA*(H21Q)::Km into the strain E. coli Δedd-eda ΔgloA, ΔaldA, ΔgldA (pME101VB01-yqhD*(G149E), was performed by the technique of transduction with phage P1. IPTG was added to the culture to promote the expression of the gene borne on the plasmid.

The modifications mgsA*(H21Q)::Km and the others deletion were checked using the oligonucleotides described in Table 5.

The strain obtained was named E. coli MG1655 mgsA*(H21Q)::Km Ptrc01-gapA::cm Δedd-eda ΔgloA, ΔaldA, ΔaldB, ΔgldA pME101-VB01-yqhD*(G149E).

3. Assessment of Acetol Production in Two E. coli Isogenic Strains Differing Only in the yqhD Alleles The two strains described above were cultivated in an Erlenmeyer flask assay (500 ml flasks with 50 ml of medium) under aerobic conditions in minimal medium MML11PG1_100 (see composition in Table 9) with 20 g/l glucose as sole carbon source. Spectinomycin was added at a concentration of 50 mg/l.

The culture was carried out at 37° C. and the pH was maintained by buffering the culture medium with MOPS.

At the end of the culture, acetol and residual glucose in the fermentation broth were analysed by HPLC using a Biorad HPX 97H column for the separation and a refractometer for the detection. The biomass concentration was recorded as dry cell weight. The 1,2-propanediol specific productions were then calculated

TABLE 12 production of acetol in minimal medium with glucose as carbon source.

| Strain | Carbon source | acetol titer (g/l) | acetol specific production (g/g biomass) |
|---|---|---|---|
| E. coli MG1655 mgsA*(H21Q)::Km ΔgloA Δedd-eda ΔaldA ΔaldB ΔgldA (pME101VB01-yqhD) | glucose | 1.90 +/− 0.18 (n = 2) | 0.933 +/− 0.043 (n = 2) |
| E. coli MG1655 mgsA*(H21Q)::Km ΔgloA Δedd-eda ΔaldA ΔaldB ΔgldA (pME101VB01-yqhD*(G149E) | glucose | 2.23 +/− 0.23 (n = 2) | 0.968 +/− 0.056 (n = 2) | n is the number of cultures of different clones of the same strain - The figures given are the mean and standard deviation of the figures obtained for n cultures.

The titer and the specific production of acetol in the E. coli strain with a mutant YqhD were improved as compared with the isogenic strain with a native YqhD.

The improved properties of the mutant YqhD enzyme shown in Example 3 will lead to a more significant improvement of the performances of the strain with a mutant YqhD over the isogenic strain when compared in fed-batch culture.

Example 7

Construction of a E. coli Strain with a Mutant MGS and a Mutant YqhD

1. Construction of the Modified Strain E. coli MG1655 Ptrc01-gapA::cm, mgsA*(H21Q), Δedd-eda, ΔgloA, ΔaldA, ΔaldB, ΔgldA, pME101-VB01-yqhD*(G149E), (pJB137-PgapA-ppsA)

The construction of this strain was described in Example 6

2. Construction of the Modified Strain E. coli MG1655 Ptrc01-gapA::cm, mgsA*(H21Q), Δedd-eda ΔgloA, ΔaldA, ΔaldB, ΔgldA pME101-VB01-yqhD*(G149E) pBBR1MCS5-cscBKAR The plasmid pBBR1MCS5-cscBKAR (see Example 5) was introduced by electroporation in the strain E. coli MG1655 Ptrc01-gapA::cm, mgsA*(H21Q), Δedd-eda ΔgloA, ΔaldA, ΔaldB, ΔgldA pME101-VB01-yqhD*(G149E).

The resulting strain was named E. coli MG1655 Ptrc01-gapA::cm, mgsA*(H21Q), Δedd-eda ΔgloA, ΔaldA, ΔaldB, ΔgldA pME101-VB01-yqhD*(G149E) pBBR1MCS5-cscBKAR.

Example 8

Construction of Two E. coli Ethylene Glycol Producing Strains Differing Only in the Overexpression of the Gene Coding for yqhD 1. Construction of the Modified Strain E. coli MG1655 ΔsdaA ΔsdaB ΔpykF Ptrcl8-gpmA Ptrcl8-gpmB (pME101-kivDll-yqhD-TT07)

The construction of the strain E. coli MG1655 ΔsdaA ΔsdaB ΔpykF Ptrcl8-gpmA Ptrcl8-gpmB pME101-kivDll-yqhD*(G149E)-TT07 is already described in patent application WO2010076324.

2. Construction of the Modified Strain E. coli MG1655 ΔsdaA ΔsdaB ΔpykF Ptrcl8-gpmA Ptrcl8-gpmB (pME101-kivDll-yqhD*(G149E)-TT07)

2.1. Construction of the Plasmid pME101-kivDll-yqhD*(G149E)-TT07

The PCR amplified fragment on genomic DNA E. coli MG1655 using the oligonucleotides yqhD Rbis and yqhD Fbis is cloned in pSCB(Strataclone®).

yqhD F bis (SEQ ID NO 27)
T*TACGTA*cccagcaaagggagcaagtaatgaacaac a region for addition of a SnaBI restriction site (italic bold upper case)
a region (lower case) homologous to the E. coli MG1655 yqhD region from 3153357 to 3153385 yqhD R bis (SEQ ID NO 28)
a*tgatct*tcTTAGCGGGCGGCTTCGTATATAC a region (upper case) homologous to the E. coli MG1655 yqhD region from 3154540 to 3154518
a region for addition of a BglII restriction site (italic bold lower case).

The resulted plasmid is named pSCB-rbsyqhD. A directed mutagenesis is performed on this plasmid with the following oligonucleotides: yqhD*G149EmutDirF (SEQ ID NO 24) and yqhD*G149EmutDirR (SEQ ID NO 25). The two oligonucleotides are homologous to the region 3153803 to 3153850. In bold face letter, bases which are changed to create the mutation G149E and capital letter, the base which are change to create EcoRV restriction site. The resulting plasmid is named pSCB-rbsyqhD*(G149E).

The plasmid pSCB-rbsyqhD*(G149E) is cut with the restriction enzymes SnaBI and BglII. the fragment containing yqhD*(G149E) is cloned into the SnaBI-BgkII sites of the vector pME101-kivDll-TT07 (see WO2010076324) giving vector pME101-kivDll-yqhD*(G149E)-TT07.

2.2. Construction of the Modified Strain MG1655 ΔsdaA ΔsdaB ΔpykF Ptrcl8-gpmA Ptrcl8-gpmB (pME101-kivDll-yqhD*(G149E)-TT07)

The pME101-kivDll-yqhD*(G149E)-TT07 plasmid is then introduced into the strain MG1655 ΔsdaA ΔsdaB ΔpykF Ptrc18-gpmA Ptrc18-gpmB.

The strain obtained is named *E. coli* MG1655 ΔsdaA ΔsdaB ΔpykF Ptrc18-gpmA Ptrc18-gpmB pME101-kivDll-yqhD*(G149E)-TT07.

Example 9

Construction of Two *E. coli* 1,4-Butanediol Producing Strains Differing Only in the Overexpression of the Gene Coding for YqhD 1. Construction of the Modified Strain *E. coli* MG1655 ΔsucCD ΔaceBAK ΔarcA ΔgdhA (pUC19-Ptrc01/OP01/RBS01-adhE2ca-prpE-TT02) (pME101-kivDll-yqhD-TT07)

The construction of the strain *E. coli* MG1655 ΔsucCD ΔaceBAK ΔarcA ΔgdhA (pUC19-Ptrc01/OP01/RBS01-adhE2ca-prpE-TT02) (pME101-kivDll-yqhD-TT07) is already described in patent application WO2010076324.

2. Construction of the Modified Strain *E. coli* MG1655 ΔsucCD ΔaceBAK ΔarcA ΔgdhA (pUC19-Ptrc01/OP01/RBS01-adhE2ca-prpE-TT02) (pME101-kivDll-yqhD*(G149E)-TT07)

The pUC19-Ptrc01/OP01/RBS01-adhE2ca-prpE-TT02 (see WO2010076324) and the pME101-kivDll-*(G149E)-TT07 (see Example 8) plasmids are then introduced into the strain MG1655 ΔsucCD ΔaceBAK ΔarcA ΔgdhA.

The strain obtained is named *E. coli* MG1655 ΔsucCD ΔaceBAK ΔarcA ΔgdhA (pUC19-Ptrc01/OP01/RBS01-adhE2ca-prpE-TT02)(pME101-kivDll-yqhD*(G149E)-TT07)

Example 10

Construction of Two *Saccharomyces cerevisiae* 1,2-Propanediol Producer Strains 1—Construction of Two *S. cerevisiae* Strains CENPK Δgpd2, Δtpi1, gldA*(A160T), yqhD, mgsA*(H21Q) and CENPK Δgpd2, Δtpi1, gldA*(A160T), yqhD*(G149E), mgsA*(H21Q)

1-1. Construction of *S. cerevisiae* Strain CENPK Δgpd2, gldA*(A160T).

The *S. cerevisiae* strain used was CEN.PK2-1C (MATa; ura3-52; trp1-289; leu2-3,112; his3 Δ1; MAL2-8C; SUC2) from Euroscarf.

The gene GPD2 was inactivated by transforming the strain CEN.PK2-1C with a PCR fragment corresponding to pTDH3-gldA*(A160T)-CYCt-pTEF1-ble-TEF1t cassette, built using the "short flanking homology" (SFH) method described by Guldener et al. (1996).

The pTDH3-gldA*(A160T)-CYCt-pTEF1-ble-TEF1t cassette was constructed using long PCR-based fusion of several fragments as described by Shevchuk et al. (2004).

pTDH3 and CYCt were amplified from the plasmid p406TDH3 (Addgene) using pTDH3/GPD2 F and pTDH3 R primers and CYCt/gldA F and CYCt/Zeo R primers respectively. gldA*(A160T)—was amplified from pSCB gldA* (A160T)—using primers gldA/TDH3F and gldA/CYCtR.

pTEF1-ble-TEF1t was amplified from the plasmid pUG66 from Euroscarf using Zeo/CYCt F and ZEO/GPD2 R as primers.

All fragments were amplified using primers having overlapping ends as described in Table 13. Each fragment was then purified.

100 ng of each fragment was used in a PCR experiment without primers, using low annealing conditions allowing their simultaneous fusion.

The unpurified product obtained in this step was used as a matrix a in a PCR experiment at high Tm, using pTDH3/GPD2 F and ZEO/GPD2 R primers having an extension of 40 bp homologous to the 40 first and 40 last by of the GPD2 locus (Table 13).

This fragments was integrated in the GPD2 locus, replacing the GPD2 open reading frame. The transformation method used was the lithium acetate method described by Schiestl and Gietz (1989). The strain CENPK, Δgpd2, gldA*(A160T) was selected on YEPD rich medium (1% bacto yeast extract, 2% bactopeptone, 2% glucose) supplemented with 75 µg/ml of phleomycin (Cayla, France). The integration of gldA*(A160T) and the deletion of GPD2 gene were confirmed by PCR on genomic DNA extracted, using GPD2 ver F and GPD2 ver R primers (Table 13).

This resulted in the heterologous expression of gldA* (A160T) and deletion of GPD2. The resulting strain was named CENPK Δgpd2, gldA*(A160T).

TABLE 13

| Primer Name | Sequence | Description |
| --- | --- | --- |
| pTDH3/GPD2 F | ATG CTT GCT GTC AGA AGA TTA ACA AGA TAC ACA TTC CTT AGT TTA TCA TTA TCA ATA CTC G (SEQ ID NO 29) | The underlined 40 nucleotides correspond to the 40 first bp of GPD2 gene 21 nucleotides in bold are homologous to the 21 first bp of pTDH3 |
| pTDH3 R | ATCCTCGAAACTAAGTTCTTGGT (SEQ ID NO 30) | 23 nucleotides homologous to the 23 last bp of pTDH3 |
| gldA/TDH3F | AAA CAC CAG AAC TTA GTT TCG AAC TAG TTT ATT CCC ACT CTT (SEQ ID NO 31) | The underlined 22 nucleotides underlined correspond to the last bp of pTDH3 20 nucleotides in bold are homologous to the 20 first bp of gldA* (A160T) |

TABLE 13-continued

| Primer Name | Sequence | Description |
| --- | --- | --- |
| gldA/CYCtR | TGA AAT ATA AAT AAC GTT CTT AAT ACT AAC ATA ACT ATA AAC TAG TAT GGA CCG CAT TAT TC (SEQ ID NO 32) | The underlined 42 nucleotides correspond to the 42 first bp of CYCt 20 nucleotides in bold are homologous to the 20 last bp of gldA*(A160T) |
| CYCt/gldA F | CCT GGA TGT ATT TAC CCG GTG ATT GAA TAA TGC GGT CCA TAC TAG TTT ATA GTT ATG TTA GTA TTA (SEQ ID NO 33) | The underlined 46 nucleotides correspond to the 46 last bp of gldA or gldA 20 nucleotides in bold are homologous to the 20 first bp of CYCt |
| CYCt/Zeo R | GAG GCA AGC TAA ACA GAT CTC TAG ACC TAG GTA CCC GCC GGC AAA TTA AAG CCT TCG AGC (SEQ ID NO 34) | The underlined 40 nucleotides correspondto the 40 first bp of ble gene 20 nucleotides in bold are homologous to the 20 last bp of CYCt |
| Zeo/CYCt F | GCT TGA GAA GGT TTT GGG ACG CTC GAA GGC TTT AAT TTG CTA GGT CTA GAG ATC TGT TTA GC (SEQ ID NO 35) | The underlined 40 nucleotides correspond to the 40 last bp of CYCt 22 nucleotides in bold are homologous to the 22 first bp of TEF1p |
| ZEO/GPD2 R | CTA TTC GTC ATC GAT GTC TAG CTC TTC AAT CAT CTC CGG TCC ACT AGT GGA TCT GAT ATC ACC T (SEQ ID NO 36) | The underlined 40 nucleotides correspond to the 40 last bp of GPD2 gene 24 nucleotides in bold are homologous to the 24 last bp of TEF1t |
| GPD2 ver F | ATG CTT GCT GTC AGA AGA TT (SEQ ID NO 37) | 20 nucleotides homologous to the 20 first bp of GPD2 gene |
| GPD2 ver R | TAG TAT GGA CCG CAT TAT TC (SEQ ID NO 38) | 20 nucleotides homologous to the 20 last nucleotides of gldA*(A160T) |

1-2. Construction of Two *S. cerevisiae* Strains CENPK Δgpd2, gldA*(A160T), yqhD and CENPK Δgpd2, gldA* (A160T), yqhD*(G149E)

The strain used was CENPK, Δgpd2, gldA*(A160T), previously built. The expression of yqhD or yqhD* (G149E) was realised by transforming the strains with a PCR fragment corresponding to a pTEF1-yqhD-CYCt-pTEF1-nat1-TEF1t cassette or pTEF1-yqhD* (G149E)-CYCt-pTEF1-nat1-TEF1t cassette using the "short flanking homology" (SFH) method.

The pTEF1-yqhD-CYCt-pTEF1-nat1-TEF1t cassette or pTEF1-yqhD* (G149E)-CYCt-pTEF1-nat1-TEF1t cassette were constructed using long PCR-based fusion of several fragments.

pTEF1 and CYCt were amplified from the plasmid p405TEF1 (Addgene) using pTEF1/URA3 F and pTEF R primers and CYCt/yqhD F and CYCt/Nat1R primers respectively. yqhD and yqhD* were amplified respectively from pSCB-yqhD and pSCB yqhD* (G149E) using primers yqhD/TEF-F and yqhD/CYCtR.

pTEF1-nat1-TEF1t was amplified from the plasmid pAG35 from Euroscarf using Nat1/CYCt F and Nat1/Leu2 as primers.

All fragments were amplified using primers having overlapping ends as described in Table 14. Each fragment was then purified.

100 ng of each fragment was used in a PCR experiment without primers using low annealing conditions allowing their simultaneous fusion.

The unpurified product obtained in this step was used as a matrix in a PCR experiment with at high Tm, using pTEF1/LEU2 F and Nat1/Leu2 primers having an extension of 40 bp homologous to the 40 first and 40 last bp of the LEU2 locus (Table 14).

These fragments were integrated in the LEU2 locus, replacing the LEU2 open reading frame.

The transformation method used was the lithium acetate method. The strain CENPK, Δgpd2, gldA*(A160T) was transformed either by pTEF1-yqhD-CYCt-pTEF1-nat1-TEF1t cassette or by pTEF1-yqhD* (G149E)-CYCt-pTEF1-nat1-TEF1t to obtained CENPK, Δgpd2, gldA* (A160T), yqhD and CENPK, Δgpd2, gldA* (A160T), yqhD* (G149E). Transformants were selected on YEPD rich medium (1% bacto yeast extract, 2% bactopeptone, 2% glucose) supplemented with 50 μg/ml of nourseothricine (Weber bioagents, Germany). The integration of yqhD or yqhD* (G149E) were confirmed by PCR on genomic DNA extracted, using YQHD ver F and YQHD ver R primers (Table 14). This resulted in the heterologous expression of yqhD and yqhD* (G149E). The resulting strains were named CENPK Δgpd2, gldA* (A160T), yqhD and CENPK Δgpd2, gldA*(A160T), yqhD* (G149E).

TABLE 14

| Primer Name | Sequence | Description |
| --- | --- | --- |
| pTEF1/URA3 F | ATG TCT GCC CCT AAG AAG ATC GTC GTT TTG CCA GGT GAC CAG CTG GAG CTC ATA GCT TCA (SEQ ID NO 39) | The underlined 40 nucleotides correspond to the 40 first bp of LEU2 gene 20 nucleotides in bold are homologous to the 20 first bp pTEF1 |
| pTEF R | TCC GGG TTG GGG TGT GCA GAT TAA AGT TGT TCA TAC TAG TGG ATC CAC TAG TTC TAG AAA (SEQ ID NO 40) | The underlined 40 nucleotides correspond to the 40 first bp of yqhD or yqhD*(G419E) 20 nucleotides bold are homologous to the 20 last bp of pTEF1 |
| yqhD/TEF-F | CAT AGC AAT CTA ATC TAA GTT TTC TAG AAC TAG TGG ATC CAC TAG TAT GAA CAA CTT TAA (SEQ ID NO 41) | The underlined 40 nucleotides correspond to the 40 last bp of pTEF1 20 nucleotides in bold are homologous to the 20 first bp of yqhD or yqhD*(G419E) |
| yqhD/CYCtR | TGA AAT ATA AAT AAC GTT CTT AAT ACT AAC ATA ACT ATA AAC TAG TTT AGC GGG CGG CTT (SEQ ID NO 42) | The underlined 40 nucleotides correspond to the 40 first bp of CYCt 20 nucleotides in bold are homologous to the 20 last bp of yqhD or yqhD*(G419E) |
| CYCt/yqhD F | TGT CAG CCG CCG TAT ATA CGA AGC CGC CCG CTA AAC TAG TTT ATA GTT ATG TTA GTA TTA (SEQ ID NO 43) | The underlined 40 nucleotides correspond to the 40 last bp of yqhD or yqhD*(G419E) 20 nucleotides in bold are homologous to the 20 first bp of CYCt |
| CYCt/Nat1R | CTCCATGTCGCTGGCCGGGTGACCCGG CGGGGACGAGGCAGCAAATTAAA GCCTTCGAGC (SEQ ID NO 44) | The underlined 40 nucleotides correspond to the 40 first bp of pTEF1 20 nucleotides in bold are homologous to the 20 last bp of CYCt |
| Nat1/CYCt F | GCT TGA GAA GGT TTT GGG ACG CTC GAA GGC TTT AAT TTG CTG CCT CGT CCC CGC CGG GTC (SEQ ID NO 45) | The underlined 40 nucleotides correspond to the 40 last bp of CYCt 20 nucleotides in bold are homologous to the 20 first bp of pTEF1 |
| Nat1/Leu2 | TTA AGC AAG GAT TTT CTT AAC TTC TTC GGC GAC AGC ATC ACA GTA TAG CGA CCA GCA TTC (SEQ ID NO 46) | The underlined 40 nucleotides correspond to the 40 last bp of LEU2 gene 20 nucleotides in bold are homologous to the 20 last bp of TEF1t |
| YQHD ver F | ATG TCT GCC CCT AAG AAG ATC (SEQ ID NO 47) | 20 nucleotides homologous to the 20 first bp of LEU2 gene |
| YQHD ver R | AC TAG TTT AGC GGG CGG CTT (SEQ ID NO 48) | 20 nucleotides homologous to the 20 last bp of yqhD or yqhD* (G149E) |

1-3. Construction of Two S. cerevisiae Strain CENPK Δgpd2, Δtpi1, gldA*(A160T), yqhD, mgsA*(H21Q) and CENPK Δgpd2, Δtpi1, gldA*(A160T), yqhD*(G149E), mgsA*(H21Q)

The two strains used was CENPK, Δgpd2, gldA*(A160T), yqhD or CENPK, Δgpd2, gldA*(A160T), yqhD*, previously built.

The gene TPI1 was inactivated by transforming the strains with a PCR fragment corresponding to a pTEF1-hph-TEF1t-pPGK1-msgA*(H21Q) cassette using the "short flanking homology" (SFH) method.

The pTEF1-hph-TEF1t-pPGK1-msgA*(H21Q) cassette was constructed using long PCR-based fusion of several fragments.

The pTEF1-hph-TEF1t-pPGK1 were amplified from the plasmid pAG35pPGK1 constructed from pAG35 (Euroscarf) using PGK1/TPI1F and PGK1/mgsAR mgsA*(H21Q) was amplified from pETTOPO mgsA*(H21Q) using the primers mgsA/PGK1F and mgsA/TPI R as primers.

All fragments were amplified using primers having overlapping ends as described in Table 15. Each fragment was then purified.

100 ng of each fragment was used in a PCR experiment without primers and using low annealing conditions, allowing their simultaneous fusion.

The unpurified product obtained in this step was used as a matrix in a PCR experiment at high Tm, using PGK1/TPI1F and mgsA/TPI R primers having an extension of 40 bp homologous to the 40 first and 40 last by of the TPI1 locus (Table 15).

This fragment was integrated in the TPI1 locus, replacing TPI1 open reading frame.

The transformation method used is the lithium acetate method. The strain CENPK, Δgpd2, gldA*(A160T), yqhD and the strain CENPK, Δgpd2, gldA*(A160T), yqhD* (G149E) was transformed by pTEF1-hph-TEF1t-pPGK1-msgA*(H21Q) cassette to obtained CENPK, Δgpd2, Δtpi1, gldA*(A160T), yqhD* (G419E), msgA*(H21Q), CENPK, Δgpd2, Δtpi1, gldA*(A16 Transformants were selected on YEPD rich medium (1% bacto yeast extract, 2% bactopeptone, 2% glucose) supplemented with 250 μg/ml of hygromycin (Sigma-Aldrich).

The integration of msgA*(H21Q) was confirmed by PCR on genomic DNA extracted, using mgsA ver F and mgsA ver R primers (Table 15).

This resulted in the heterologous expression of mgsA* (H21Q) and deletion of TPI1. The resulting strains were named CENPK Δgpd2, Δtpi1, gldA*(A160T), yqhD, mgsA* (H21Q) and CENPK Δgpd2, Δtpi1, gldA*(A160T), yqhD* (G149E), mgsA*(H21Q).

Tang X, Tan Y, Zhu H, Zhao K, Shen W (2009), *Appl. Environ. Microbiol.* 75: 1628-1634

Nakamura C E and Whited G M (2003), *Curr. Opin. Biotechnol.* 14: 454-459

Li H, Chen J, Li Y (2008), *Progress in Natural Science* 18: 1519-1524

Perez J M, Arenas F A, Pradenas G A, Sandoval J M, Vasquez C C (2008), *J. Biol. Chem.* 283: 7346-7353

Sulzenbacher G, Alvarez K, Van den Heuvel R H H, Versluis C, Spinelli S, Campanacci V, Valencia C, Cambillau C, Eklund H, Tegoni M (2004), *J. Mol. Biol.* 342: 489-502

Miller E N, Jarboe L R, Yomano L P, York S W, Shanmugan K T, Ingram L O (2009), *Appl. Environ. Microbiol.* In press Cameron D C, Altaras N E, Hoffman M L, Shaw A J (1998), *Biotechnol. Prog.* 14: 116-125

Altaras N E and Cameron D C (2000), *Biotechnol. Prog.* 16: 940-946

Bennett G N and San K Y, (2001), *Appl. Microbiol. Biotechnol.* 55: 1-9

TABLE 15

| Primer Name | Sequence | Description |
|---|---|---|
| PG1/TPI1F | ATG TCG AAA GCT ACA TAT AAG GAA CGT GCT GCT ACT CAT CGC CAG ATC TGT TTA GCT TGC (SEQ ID NO 49) | The underlined 40 nucleotides correspond to the 40 first bp of TPI1 gene. 20 nucleotides in bold are homologous to 20 the first bp pTEF1 |
| PGK1/mgsAR | GTG CGA GTC GTC AGT TCC ATA ATA CGC AAA CCG CCT CTC C (SEQ ID NO 50) | The underlined 21 nucleotides correspond to the 40 first bp of mgsA or msgA*(H21Q). 19 nucleotides in bold are homologous to 20 the last bp of pPGK1 |
| mgsA/PGK1F | GGA GAG GCG GTT TGC GTA TTA TGG AAC TGA CGA CTC GCA C (SEQ ID NO 51) | The underlined 22 nucleotides correspond to the 40 last bp of pPGK1. 18 nucleotides in bold are homologous to the 20 first bp of mgsA or msgA*(H21Q) |
| mgsA/TPI R | TTA GTT TTG CTG GCC GCA TCT TCT CAA ATA TGC TTC CCT TTA CTT CAG ACG GTC CGC GAG (SEQ ID NO 52) | The underlined 40 nucleotides correspond to the 40 last bp of TPI1. 20 nucleotides in bold are homologous to the 20 last bp of mgsA or msgA*(H21Q) |
| mgsA ver F | GG AAC TGA CGA CTC GCA C (SEQ ID NO 53) | 20 nucleotides homologous to the 20 first bp of TPI1 gene |
| mgsA ver R | TTAGTTTCTAGAGTTGATGA (SEQ ID NO 54) | 20 nucleotides homologous to the 20 last bp of msgA*(H21Q) |

REFERENCES

Wang F, Qu H, Zhang D, Tian P, Tan T (2007), *Mol. Biotechnol.* 37: 112-119

Rao Z, Ma Z, Shen W, Fang H, Zhuge J, Wang X (2008), *J. Appl. Microbiol.* 105: 1768-1776

Ko J, Kim I, Yoo S, Min B, Kim K, Park C (2005), *J. Bacteriol.* 187: 5782-5789

Guldener, U., et al., (1996), *Nucleic Acids Res.* 24: 2519-24

Schiestl, R. H. and Gietz, R. D., (1989), *Curr Genet.* 16: 339-46.

Shevchuk, N. A., et al., (2004), *Nucleic Acids Res.* 32: e19

The invention claimed is:

1. A method for production of a biochemical selected from the group consisting of acetol; 1,2-propanediol; ethylene glycol; and 1,4-butanediol, said method comprising
culturing a microorganism modified for an improved production of the biochemical selected from the group consisting of acetol; 1,2-propanediol; ethylene glycol; and 1,4-butanediol in an appropriate culture medium, and recovering said biochemical,
wherein said microorganism expresses a mutant YqhD enzyme (1,3-propanediol oxidoreductase), wherein said mutant YqhD enzyme is selected from the group consisting of: the polypeptide set forth in SEQ ID NO 1; the polypeptide set forth in SEQ ID NO 2; and the polypeptide set forth in SEQ ID NO 3,
and wherein the catalytic efficiency of the mutant YqhD enzyme toward NADPH and methylglyoxal is increased compared to the unmutated parent YqhD enzyme.

2. The method of claim 1 for production of acetol wherein said microorganism comprises a gene coding for a mutant methylglyoxal synthase.

3. The method of claim 1 for production of 1,2-propanediol wherein said microorganism comprises a gene coding for a mutant methylglyoxal synthase or a gene coding for a mutant glycerol dehydrogenase.

4. The method of claim 1, wherein the microorganism is selected from the group consisting of Enterobacteriaceae; Bacillaceae; Clostridiaceae; Streptomycetaceae; Corynebacteriaceae; and yeasts.

5. The method of claim 4, wherein said microorganism is selected from the group consisting of Escherichia coli; Klebsiella pneumonia; Thermoanaerobacterium thermosaccharolyticum; Clostridium sphenoides; and Saccharomyces cerevisiae.

6. The method of claim 1, wherein said microorganism is E. coli.

7. The method of claim 1, wherein said recovered biochemical comprises acetol and/or 1,2-propanediol and/or ethylene glycol and/or 1,4-butanediol and said biochemical is purified.

8. The method of claim 1, wherein said appropriate culture medium comprises at least one carbon source selected from the group consisting of glucose; sucrose; mono- or disaccharides; starch; and derivatives thereof.

9. The method of claim 8, wherein said carbon source is selected from the group consisting of glucose and sucrose.

10. The method of claim 1, wherein said production comprises a batch, fed-batch or continuous process.

11. An isolated mutant YqhD enzyme (1,3-propanediol oxidoreductase), wherein said mutant YqhD enzyme is selected from the group consisting of: the polypeptide set forth in SEQ ID NO 1; the polypeptide set forth in SEQ ID NO 2; and the polypeptide set forth in SEQ ID NO 3,
and wherein the catalytic efficiency of the mutant YqhD enzyme toward NADPH and methylglyoxal is increased compared to the unmutated parent YqhD enzyme.

12. The isolated mutant YqhD enzyme of claim 11, wherein the catalytic efficiency toward NADPH is at least 80,000 $M^{-1} s^{-1}$.

13. The isolated mutant YqhD enzyme of claim 11, wherein the mutant of YqhD enzyme is more sensitive to inhibition by $NADP^{+}$ than a native YqhD enzyme from Escherichia coli.

14. The isolated mutant YqhD enzyme of claim 1, wherein the $NADP^{+}$ inhibition constant (Ki) of the mutant of YqhD enzyme is 2 or 3 factors lower than the $NADP^{+}$ inhibition constant (Ki) of a native YqhD enzyme from Escherichia coli.

15. The isolated mutant YqhD enzyme of claim 11, wherein the mutant of YqhD enzyme is recombinantly produced by a microorganism.

* * * * *